United States Patent
Wong et al.

(10) Patent No.: US 7,846,915 B2
(45) Date of Patent: Dec. 7, 2010

(54) STILBENES AND CHALCONES FOR THE PREVENTION AND TREATMENT OF CARDIOVASCULAR DISEASES

(75) Inventors: Norman C. W. Wong, Calgary (CA); Joseph E. L. Tucker, Calgary (CA); Henrik C. Hansen, Calgary (CA); Fabrizio S. Chiacchia, Calgary (CA); David McCaffrey, Lethbridge (CA)

(73) Assignee: Resverlogix Corporation, Calgary, Alberta (CA)

( * ) Notice: Subject to any disclaimer, the term of this patent is extended or adjusted under 35 U.S.C. 154(b) by 728 days.

(21) Appl. No.: 11/254,420

(22) Filed: Oct. 20, 2005

(65) Prior Publication Data

US 2006/0205792 A1    Sep. 14, 2006

Related U.S. Application Data

(60) Provisional application No. 60/620,888, filed on Oct. 20, 2004, provisional application No. 60/626,819, filed on Nov. 10, 2004, provisional application No. 60/665,859, filed on Mar. 29, 2005.

(51) Int. Cl.
| | |
|---|---|
| A01N 57/00 | (2006.01) |
| A01N 43/00 | (2006.01) |
| A01N 43/16 | (2006.01) |
| A01N 43/40 | (2006.01) |
| A61K 31/67 | (2006.01) |
| A61K 31/33 | (2006.01) |
| A61K 31/35 | (2006.01) |
| A61K 31/44 | (2006.01) |

(52) U.S. Cl. .................. 514/96; 514/183; 514/456; 514/352

(58) Field of Classification Search ............. 514/183, 514/96, 456, 352
See application file for complete search history.

(56) References Cited

U.S. PATENT DOCUMENTS

| | | |
|---|---|---|
| 2,065,593 A | 12/1936 | Lubs |
| 2,065,900 A | 12/1936 | Laska et al. |
| 2,071,329 A | 2/1937 | Brown |
| 3,251,837 A | 5/1966 | Holland |
| 3,600,394 A | 8/1971 | Coyne et al. |
| 3,773,946 A | 11/1973 | Creger |
| 3,930,024 A | 12/1975 | Creger |
| 3,965,128 A | 6/1976 | Fürst et al. |
| 4,613,593 A | 9/1986 | Yamatsu et al. |
| 4,689,344 A | 8/1987 | Bar-Tana |
| 4,711,896 A | 12/1987 | Bar-Tana et al. |
| 5,124,337 A | 6/1992 | Dugar et al. |
| 5,126,351 A | 6/1992 | Luzzio et al. |
| 5,244,904 A | 9/1993 | Nagase et al. |
| 5,354,749 A | 10/1994 | Dressel et al. |
| 5,407,942 A | 4/1995 | Dressel et al. |
| 5,446,071 A | 8/1995 | Grese |
| 5,480,883 A | 1/1996 | Spada et al. |
| 5,539,119 A | 7/1996 | Nagase et al. |
| 5,576,322 A | 11/1996 | Takase et al. |
| 5,595,974 A | 1/1997 | Tomaru |
| 5,693,652 A | 12/1997 | Takase et al. |
| 5,707,987 A | 1/1998 | Nakagawa et al. |
| 5,733,913 A | 3/1998 | Blankley |
| 5,756,344 A | 5/1998 | Onda et al. |
| 5,756,544 A | 5/1998 | Bisgaier et al. |
| 5,756,736 A | 5/1998 | Arzeno et al. |
| 5,756,763 A | 5/1998 | Takeuchi et al. |
| 5,763,414 A | 6/1998 | Bok et al. |
| 5,783,577 A | 7/1998 | Houghten et al. |
| 5,792,461 A | 8/1998 | Bok et al. |
| 5,792,902 A | 8/1998 | Benoit et al. |
| 5,801,180 A | 9/1998 | Takase et al. |
| 5,854,264 A | 12/1998 | Anthony et al. |
| 5,877,208 A | 3/1999 | Bok et al. |
| 5,922,866 A | 7/1999 | Miyata et al. |
| 5,965,556 A | 10/1999 | Takeuchi et al. |
| 6,022,901 A | 2/2000 | Goodman |
| 6,048,903 A | 4/2000 | Toppo |
| 6,054,435 A | 4/2000 | Or et al. |
| 6,133,241 A | 10/2000 | Bok et al. |
| 6,165,984 A | 12/2000 | Bok et al. |
| 6,168,776 B1 | 1/2001 | Klunk et al. |
| 6,239,114 B1 | 5/2001 | Guthrie et al. |
| 6,291,456 B1 | 9/2001 | Stein et al. |

(Continued)

FOREIGN PATENT DOCUMENTS

AU    719140    7/1998

(Continued)

OTHER PUBLICATIONS

Vippagunta et al. Advanced Drug Delivery Reviews. 2001, vol. 48, pp. 3-26.*

(Continued)

*Primary Examiner*—Sreeni Padmanabhan
*Assistant Examiner*—Samira Jean-Louis
(74) *Attorney, Agent, or Firm*—Finnegan, Henderson, Farabow, Garrett & Dunner, LLP

(57) ABSTRACT

The present disclosure provides non-naturally occurring polyphenol compounds that upregulate the expression of Apolipoprotein A-I (ApoA-I). The disclosed compositions and methods can be used for treatment and prevention of cardiovascular disease and related disease states, including cholesterol or lipid related disorders, such as, e.g., atherosclerosis.

13 Claims, No Drawings

U.S. PATENT DOCUMENTS

| | | |
|---|---|---|
| 6,303,629 B1 | 10/2001 | Kun |
| 6,414,037 B1 | 7/2002 | Pezzuto et al. |
| 6,455,577 B2 | 9/2002 | Bok et al. |
| 6,482,479 B1 | 11/2002 | Dubal et al. |
| 6,512,161 B1 | 1/2003 | Rouy et al. |
| 6,541,045 B1 | 4/2003 | Charters et al. |
| 6,541,522 B2 * | 4/2003 | Inman et al. ............... 514/568 |
| 6,548,548 B2 | 4/2003 | Campbell et al. |
| 6,613,772 B1 | 9/2003 | Schindler et al. |
| 6,635,642 B1 | 10/2003 | Jackson et al. |
| 6,673,780 B2 | 1/2004 | Dasseux et al. |
| 6,703,422 B2 | 3/2004 | Dasseux et al. |
| 7,173,128 B2 | 2/2007 | Ravichandran et al. |
| 7,244,776 B2 | 7/2007 | Ravichandran et al. |
| 2002/0091263 A1 | 7/2002 | Trova |
| 2003/0064967 A1 | 4/2003 | Luchoomun et al. |
| 2003/0068526 A1 | 4/2003 | Kamatani et al. |
| 2003/0072964 A1 | 4/2003 | Kwong et al. |
| 2003/0171429 A1 | 9/2003 | Chen et al. |
| 2004/0001834 A1 | 1/2004 | Kim et al. |
| 2004/0033480 A1 | 2/2004 | Wong et al. |
| 2004/0058903 A1 | 3/2004 | Takasugi et al. |
| 2004/0097493 A1 | 5/2004 | Chen |
| 2004/0198750 A1 | 10/2004 | Green et al. |
| 2004/0235888 A1 * | 11/2004 | Yamamori et al. .......... 514/309 |
| 2004/0242615 A1 | 12/2004 | Yamamori et al. |
| 2005/0043300 A1 | 2/2005 | Middleton et al. |
| 2005/0080021 A1 | 4/2005 | Tucker et al. |
| 2005/0080024 A1 * | 4/2005 | Tucker et al. ................ 514/27 |
| 2005/0261319 A1 | 11/2005 | Deuschle et al. |
| 2006/0116364 A1 | 6/2006 | Hamaoka et al. |
| 2007/0185160 A1 | 8/2007 | Hattori et al. |
| 2007/0218155 A1 * | 9/2007 | Kuhrts ...................... 424/778 |

FOREIGN PATENT DOCUMENTS

| | | |
|---|---|---|
| CA | 2104981 | 3/1994 |
| CA | 2345406 | 4/2000 |
| CN | 1067070 | 2/1997 |
| DE | 637259 | 10/1936 |
| DE | 652772 | 11/1937 |
| DE | 36 01 417 | 7/1987 |
| DE | 42 15 588 | 11/1993 |
| DE | 196 51 099 | 6/1998 |
| DE | 19756388 A1 | 6/1999 |
| DE | 199 34 799 | 2/2002 |
| EP | 0 210 342 | 4/1986 |
| EP | 0 258 190 B1 | 3/1988 |
| EP | 182 213 | 9/1990 |
| EP | 0 407 217 A1 | 1/1991 |
| EP | 488 602 | 6/1992 |
| EP | 272 455 | 2/1993 |
| EP | 0 564 350 | 10/1993 |
| EP | 375 404 | 2/1994 |
| EP | 333 175 | 6/1994 |
| EP | 0 607 439 B1 | 7/1994 |
| EP | 343 499 | 7/1994 |
| EP | 409 413 | 8/1994 |
| EP | 420 511 | 8/1994 |
| EP | 0 633 022 | 1/1995 |
| EP | 569 795 | 4/1995 |
| EP | 330 108 | 12/1995 |
| EP | 0 747 051 | 12/1996 |
| EP | 643 119 | 4/2000 |
| EP | 1 125 908 A1 | 8/2001 |
| EP | 0 498 723 B1 | 9/2001 |
| EP | 776 893 | 2/2002 |
| EP | 1 195 378 | 4/2002 |
| EP | 1 277 738 A1 | 1/2003 |
| EP | 1 398 032 A1 | 3/2004 |
| EP | 1 418 164 | 5/2004 |
| EP | 1 426 046 | 6/2004 |
| EP | 1 477 481 A1 | 11/2004 |
| EP | 1 637 523 A1 | 3/2006 |
| EP | 2 005 941 A2 | 12/2008 |
| FR | 803201 | 9/1936 |
| FR | 803619 | 10/1936 |
| FR | 2 244 492 | 4/1975 |
| FR | 2 244 493 | 4/1975 |
| GB | 472489 | 3/1936 |
| GB | 1 175 808 | 12/1969 |
| GB | 1 179 019 | 1/1970 |
| GB | 2 292 149 | 2/1996 |
| JP | 6-80656 | 3/1994 |
| JP | 7-41442 | 2/1995 |
| JP | 7-61942 | 3/1995 |
| JP | 7-118241 | 5/1995 |
| JP | 7-179380 | 7/1995 |
| JP | 7-233109 | 9/1995 |
| JP | 7-247289 | 9/1995 |
| JP | 7-247289 A | 9/1995 |
| JP | 10-287678 A | 10/1998 |
| JP | 2001/131151 | 5/2001 |
| JP | 2001/139550 | 5/2001 |
| JP | 2001/335476 | 12/2001 |
| JP | 2002/249483 | 6/2002 |
| JP | 2004/307440 | 4/2004 |
| JP | 2004-203751 A | 7/2004 |
| WO | WO 91/18901 | 12/1991 |
| WO | WO 92/09374 | 6/1992 |
| WO | WO 92/18123 | 10/1992 |
| WO | WO 92/20642 A1 | 11/1992 |
| WO | WO 92/21661 | 12/1992 |
| WO | WO 93/07124 A1 | 4/1993 |
| WO | WO 93/08174 | 4/1993 |
| WO | WO 94/14763 | 7/1994 |
| WO | WO 95/03277 | 2/1995 |
| WO | WO 95/23150 | 8/1995 |
| WO | WO 96/15128 | 5/1996 |
| WO | WO 96/31206 | 10/1996 |
| WO | WO 97/10221 A1 | 3/1997 |
| WO | WO 97/15308 | 5/1997 |
| WO | WO 97/28118 A1 | 8/1997 |
| WO | WO 97/28132 A1 | 8/1997 |
| WO | WO 97/28134 A1 | 8/1997 |
| WO | WO 97/29106 | 8/1997 |
| WO | WO 97/48694 | 12/1997 |
| WO | WO 98/11438 A1 | 3/1998 |
| WO | WO 98/26127 | 6/1998 |
| WO | WO 98/30530 | 7/1998 |
| WO | WO 98/50370 A1 | 11/1998 |
| WO | WO 98/51307 | 11/1998 |
| WO | WO 98/51308 | 11/1998 |
| WO | WO 98/55124 | 12/1998 |
| WO | WO 99/00116 | 1/1999 |
| WO | WO 99/11634 | 3/1999 |
| WO | WO 99/18077 | 4/1999 |
| WO | WO 99/29667 | 6/1999 |
| WO | WO 00/23075 | 4/2000 |
| WO | WO 00/35865 | 6/2000 |
| WO | WO 00/44362 | 8/2000 |
| WO | WO 00/55168 | 9/2000 |
| WO | WO 00/64888 | 11/2000 |
| WO | WO 01/00554 | 1/2001 |
| WO | WO 01/60775 A1 | 8/2001 |
| WO | WO 01/82916 | 11/2001 |
| WO | WO 01/83456 A1 | 11/2001 |
| WO | WO 02/44189 | 6/2002 |
| WO | WO 02/074307 | 9/2002 |
| WO | WO 02/087556 | 11/2002 |
| WO | WO 02/096426 | 12/2002 |
| WO | WO 03/007959 | 1/2003 |
| WO | WO 03/016292 A1 | 2/2003 |
| WO | WO 03/018008 | 3/2003 |

| | | |
|---|---|---|
| WO | WO 03/040256 | 5/2003 |
| WO | WO 03/040257 | 5/2003 |
| WO | WO 2003/070236 | 8/2003 |
| WO | WO 03/099274 A1 | 12/2003 |
| WO | WO 03/106435 A1 | 12/2003 |
| WO | WO 2004/017920 | 3/2004 |
| WO | WO 2004/032846 | 4/2004 |
| WO | WO 2004/039795 | 5/2004 |
| WO | WO 2004/047755 | 6/2004 |
| WO | WO 2004/056355 | 7/2004 |
| WO | WO 2004/058717 | 7/2004 |
| WO | WO 2004/065392 A1 | 8/2004 |
| WO | WO 2004/072042 | 8/2004 |
| WO | WO 2004/092196 A2 | 10/2004 |
| WO | WO 2004/094452 A2 | 11/2004 |
| WO | WO 2004/112710 | 12/2004 |
| WO | WO 2005/034960 | 4/2005 |
| WO | WO 2005/065183 A2 | 7/2005 |
| WO | WO 2005/066162 A1 | 7/2005 |
| WO | WO 2005/075431 A1 | 8/2005 |
| WO | WO 2006/071095 A1 | 7/2006 |
| WO | WO 2006/105081 A2 | 10/2006 |
| WO | WO 2007/071055 A1 | 6/2007 |

OTHER PUBLICATIONS

Webster Ninth New Collegiate Dictionarry, 2000, Definition of Prevent, p. 1.*
Clarkson et al. Journal of Clinical Endocrinology & Metabolism, 2001, vol. 86, No. 1, pp. 41-47.*
Ohtomo et al. European Journal of Nutrition, 2008 vol. 47, pp. 273-279.*
Hakamata et al. FEBS letters, 1995, vol. 363, pp. 29-32.*
"trans-Resveratrol [501-36-0]. Review of Toxicological Literature." Mar. 2002.
Acton et al., "Identification of Scavenger Receptor SR-BI as a High Density Lipoprotein Receptor," Science 271:518-520 (1996).
Asztalos, "High-Density Lipoprotein Metabolism and Progression of Atherosclerosis: New Insights from the HDL Atherosclerosis Treatment Study," Curr Opin Cardiol 19:385-391 (2004).
Badimon et al., "Role of High Density Lipoproteins in the Regression of Atherosclerosis," Circulation 86(Suppl. III):86-94 (1992).
Barrans et al., "Pre-β HDL: Structure and Metabolism," Biochem Biophys Acta 1300:73-85 (1996).
Barter et al., "High Density Lipoproteins and Coronary Heart Disease," Atherosclerosis 121:1-12 (1996).
Bertele et al., "Platelet Thromboxane Synthetase Inhibitors with Low Doses of Aspirin: Possible Resolution of the 'Aspirin Dilemma,'" Science 220:517-519 (1983).
Beugelmans et al., "Synthesis Via SRN1 Reactions: Part IV. One-pot Synthesis of 1-oxi-1,2-Dihydroisoquinolines (Isocarbostyrils) Via SRN1 (Ar) Reactions," Synthesis 9:729-731 (1981).
Bisagni et al., "A Convenient Way to Dibenzo[c,h]-1,5-Naphthyridines (11-Aza-Benzo[c]phenanthridines)," Tetrahedron 52:10427-10440 (1996).
Bisgaier et al., "A Novel Compound that Elevates High Density Lipoprotein and Activates the Peroxisome Proliferator Activated Receptor," J Lipid Res 39:17-30 (1998).
Boyce et al., "Acylation and Alkylation of O-Tolunitrile. A New Route to 3-Substituted Isocarbostyrils," J Org Chem 31:3807-3809 (1966).
Bradsher et al., "A New Isoquinoline Synthesis Via O-Substituted Benzylamines," Tetrahedron Lett 31:3149-3150 (1972).
Bradsher et al., "α-Acyl-o-Tolunitriles As Intermediates in the Preparation of 3-Substituted Isoquinolines and 1-Amino-2-Benzopyrylium Derivatives," J Org Chem 43:3817-3820 (1978).
Cherubini et al., "Role of antioxidants in Atherosclerosis: Epidemiological and Clinical Update," Curr Pharm Des 11:2017-2032 (2005).
Cho et al., "Molecular Modeling of 3-Arylisoquinoline Antitumor Agents Active Against A-549. A Comparative Molecular Field Analysis Study," Bioorg Med Chem 10:2953-2961 (2002).
Cho et al., "Synthesis and Biological Evaluation of 3-Arylisoquinolines As Antitumor Agents," Bioorg Med Chem Lett 8:41-46 (1998).
Cho et al., "Synthesis and Antitumor Activity of 3-Arylisoquinoline Derivatives," Arch Pharm Res 20:264-268 (1997).
Cho et al., "Synthesis and Comparative Molecular Field Analysis (CoMFA) of Antitumor 3-Arylisoquinoline. Derivatives," Bioorg Med Chem 6(12):2449-2458 (1998).
Chyu et al., "Differential Effects of Green Tea-Derived Catechin on Developing Versus Established Atherosclerosis in Apolipoprotein E-Null Mice," Circulation 109:2448-2453 (2004).
Cramer et al., "New Syntheses of Aryl Fluorides and Aryl Fluorosulfonates from Oxyflourides of Sulfur," J Org Chem 26:4164-4165 (1961).
Dai et al., "Synthesis of 3,4-disubstitute Isoquinolines Via Palladium-Catalyzed Cross-Coupling of 2-(1-alkynyl)benzaldimines and Organic Halides," Journal of Organic Chemistry 68:920-928 (2003).
Dai et al., "Synthesis of 3-Substituted 4-Aroylisoquinolines Via Pd-Catalyzed Carbonylative Cyclization of 2-(1-Alkynyl)benzaldimines," J Org Chem 67:7042-7047 (2002).
Dansky et al., "High-Density Lipoprotein and Plaque Regression The Good Cholesterol Gets Even Better," Circulation 100:1762-1763 (1999).
Decossin et al., "Subclasses of LpA-I in Coronary Artery Disease: Distribution and Cholesterol Efflux Ability," Eur J Clin Invest 27:299-307 (1997).
Esterbauer et al., "Continuous Monitoring of in Vitro Oxidation of Human Low Density Lipoprotein," Free Radical Res Commun 6:67-75 (1989).
Ferreira et al., "Diversity of Structure and Function in Oligomeric Flavanoids," Tetrahedron 48:1743-1803 (1992).
Fielding et al., "Molecular Physiology of Reverse Cholesterol Transport," J Lipid Res 36:211-228 (1995).
Flammang et al., "2,3-Benzodiazepines: 2-Aminoisoquinolinones From Ring Contraction of 1-oxo-2,3-Benzodiazepines," C R Acad Sci Paris, Series C 290:361-363 (1980).
Fokialakis et al., "A New Class of Phytoestrogens: Evaluation of the Estrogenic Activity of Deoxybenzoins," Chem Biol 11:397-406 (2004).
Gidez et al., "Separation and Quantitation of Subclasses of Human Plasma High Density Lipoproteins by a Simple Precipitation Procedure," J Lipid Res 23:1206-1223 (1982).
Gordon et al., "High Density Lipoprotein As a Protective Factor Against Coronary Heart Disease," Am J Med 62(5):707-714 (1977).
Gugler et al., "Disposition of Quercetin in Man After Single Oral and Intravenous Doses," Eur J Clin Pharmacol 9:229-234 (1975).
Heeg et al., "Plasma Levels of Probucol in Man After Single and Repeated Oral Doses," La Nouvelle Presse Medicale 9:2990-2994 (1980).
Hertog et al., "Dietary Antioxidant Flavonoids and Risk of Coronary Heart Disease: One Zutphen Elderly Study," Lancet 342:1007-1011 (1993).
Hidaka et al., "Affinity Purification of the Hepatic High-Density Lipoprotein Receptor Identifies Two Acidic Glycoproteins and Enables Further Characterization of Their Binding Properties," Biochem J 15:161-167 (1992).
Hirano et al., "Genetic Cholesteryl Ester Transfer Protein Deficiency Is Extremely Frequent in the Omagari Area of Japan. Marked Hyperalphalipoproteinemia Caused by CETP Gene Mutation Is Not Associated With Longevity," Arterioscler Thromb Vasc Biol 17:1053-1059 (1997).
Huang et al., "Synthesis of Isoquinolines by Palladium-Catalyzed Cyclization, Followed by a Heck Reaction," Tetrahedron Lett 43:3557-3560 (2002).
Ishibashi et al., "Hypercholesterolemia in Low Density Lipoprotein Receptor Knockout Mice and its Reversal by Adenovirus-Mediated Gene Delivery," J Clin Invest 92:883-893 (1993).
Ishibashi et al., "Massive Xanthomatosis and Atherosclerosis in Cholesterol-Fed Low Density Lipoprotein Receptor-Negative Mice," J Clin Invest 93:1885-1893 (1994).
Jayatilake et al., "Kinase Inhibitors From Polygonum Cuspidatum," J Nat Prod 56:1805-1810 (1993).

Kilbourne et al., "Involvement of Early Growth Response Factor Egr-1 in Apolipoprotein Al Gene Transcription," *J Biol Chem* 270:7004-7010 (1995).

Kim et al., "Hypothetical Drug Binding Receptor Site Analysis Using CoMFA Method for 3-Arylisoquinolines Active Against SK-OV-3 Tumor Cell Line," *Yakhak Hoechi* 46(4):219-225 (2002).

Kulkarni et al., "Quantification of $HDL_2$ and $HDL_3$ Cholesterol by the Profile-II (VAP-II) Methodology," *J Lipid Res* 38:2353-2364 (1997).

Kurata et al., "A Candidate High Density Lipoprotein (HDL) Receptor, $HB_2$, With Possible Multiple Functions Shows Sequence Homology with Adhesion Molecules," *J Atheroscler Thromb* 4:112-117 (1998).

Kurowska, "Essential Amino Acids in Relation to Hypercholesterolemia Induced in Rabbits by Dietary Casein," *J Nutr* 120:831-836 (1990).

Kuzuyza et al., "Probucol Prevents Oxidative Injury to Endothelial Cells," *J Lipid Res* 32:197-204 (1991).

Lagrost et al., "Opposite Effects of Cholesteryl Ester Transfer Protein and Phospholipid Transfer Protein on the Size Distribution of Plasma High Density Lipoproteins," *J Biol Chem* 271:19058-19065 (1996).

Landshulz et al., "Regulation of Scavenger Receptor, Class B, Type I, a High Density Lipoprotein Receptor, in Liver and Steroidogenic Tissues of the Rat," *J Clin Invest* 98:984-995 (1996).

Lin et al., "Chemoprevention of Cancer and Cardiovascular Disease by Resveratrol," *Proc. Natl. Sci. Counc. ROC* (B) 23:99-106 (1999).

Lin et al., "Solvent Effects on Aza-Anionic Cycloaromatization of 2-(2-Substituted-Ethynyl)Benzonitriles," *J Chinese Chem Soc* 48:211-214 (2001).

Lin et al., "The Role of Absorption, Distribution, Metabolism, Excretion and Toxicity in Drug Recovery," *Curr Top Med Chem* 3:1125-1154 (2003).

Manach et al., "Polyphenols and prevention of cardiovascular diseases," *Curr Opin Lipidol* 1:77-84 (2005).

Marks, "Epidermal Growth Control Mechanisms, Hyperplasia, and Tumor Promotion in the Skin," *Cancer Res* 36:2636-2343 (1976).

Mondal et al., "Two-Stage Chemical Oncogenesis in Cultures of C3H/10T1/2 Cells," *Cancer Res* 36:2254-2260 (1976).

Nourooz-Zadeh, "Ferrous Ion Oxidation in Presence of Xylenol Orange for Detection of Lipid Hydroperoxides in Plasma," *Methods Enzymol* 300:58-62 (1999).

Parra et al., "A Case-Control Study of Lipoprotein Particles in Two Populations at Contrasting Risk for Coronary Heart Disease," *Arterioscler Thromb* 12:701-707 (1992).

Pearson et al., "The Ortho Bromination of Phenols," *J Org Chem* 32:2358-2360 (1967).

Pettit et al., "Antineoplastic Agents. 465. Structural Modification of Resveratrol: Sodium Resverastatin Phosphate," *J Med Chem* 45:2534-2542 (2002).

Rice-Evans, "Flavonoids and Isoflavones: Absorption, Metabolism, and Bioactivity," *Free Radical Biol Med* 36:827-828 (2004).

Rigotti et al., "Regulation by Adrenocorticotropic Hormone of the in Vivo Expression of Scavenger Receptor Class B Type I (SR-BI), a High Density Lipoprotein Receptor, in Steroidogenic Cells of the Murine Adrenal Gland," *J Biol Chem* 271:33545-33549 (1996).

Rose et al., "Oxygen Heterocycles. XIII. From 3-Arylisocoumarins to 3-Arylisoquinolines and 4-Aryl-5H-2,3-Benzodiazepines," *J Chem Soc [Section] C: Organic* 17:2205-2208 (1968).

Rubin et al., "Expression of Human Apolipoprotein A-1 in Transgenic Mice Results in Reduced Plasma Levels of Murine Apolipoprotein A-1 and the Appearance of Two New High Density Lipoprotein Size Subclasses.," *Proc Natl Acad Sci USA* 88:434-438 (1991).

Rubin et al., "Inhibition of Early Atherogenesis in Transgenic Mice by Human Apolipoprotein Al.," *Nature* 353:265-267 (1991).

Sarkhel et al., "3-Arylisocoumarin: Synthesis of 3-(4-Methoxyphenyl)Isocoumarin," *J Indian Chem Soc* 53:915-916 (1976).

Schiess et al., "Thermolytic Ring Opening of Acyloxybenzocyclobuteness: An Efficient Route to 3-Substitute Isoquinolines," *Tetrahedron Lett* 26:3959-3962 (1985).

Shapiro et al., "Micro Assay for 3-Hydroxy-3-Methylglutaryl-CoA Reductase in Rat Liver and L-Cell Fibroblasts", *Biochem Biophys Acta* 370:369-377 (1974).

Slowing et al., "Anti-Inflammatory Activity of Leaf Extracts of Eugenia Jambos in Rats", *J Ethnopharmacol* 43:9-11 (1994).

Sun et al., "In Vitro Testing of Drug Absorption for Drug 'Developability' Assessment: Forming an Interface Between in Vitro Preclinical Data and Clinical Outcome," *Curr Opin Drug Discov Devel* 7:75-85 (2004).

Suryadevara et al., "Association of Abnormal Serum Liquids in Elderly Persons with Artherosclerotic Vascular Disease and Demetia. Artheroslerotic Vascular Disease Without Demetia, Demetia Without Artherosclerotic Vascular Disease, and No Dementia or Artherosclerotic Vascular Disease," *J Gerontol Med Sci* 58(9):M859-861 (2003).

Talbert, "Current Recommendations for the Treatment of Dyslipidemia," *Pharm. Ther.* 29:104 (2004).

Tardiff et al., "Probucol and Multivitamins in the Prevention of Restenosis After Coronary Angioplasty," *N Engl J Med* 337:365-367 (1997).

Toth et al., "Therapeutic Interventions Targeted at the Augmentation of Reserve Cholesterol Transport," *Curr Opin Cardiol* 19:374-379 (2004).

Tovar et al., "Pyrylium Salts Via Electrophilic Cyclization: Applications for Novel 3-Arylisoquinoline Syntheses," *J Org Chem* 64:6499-6504 (1999).

Tudan, "Selective Inhibition of Protein Kinase C, Mitogen-Activated Protein Kinase, and Neutrophil Activation in Response to Calcium Pyrophosphate Dihydrate Crystals, Formyl-Methionyl-Leucyl-Phenylalanine, and Phorbol Ester by O-(Chloroacetyl-carbamoyl) Fumagillol (AGM-01470; TNP-470)," *Biochem Pharmacol* 58:1869-1880 (1999).

Van Der Goot et al., "The Growth-Inhibitory Action of Some 1-Aminoisoquinolines and Related Compounds on Mycoplasma Gallisepticum," *Eur J Med Chem* 10:603-606 (1975).

Varin et al., "Enzymatic Assay for Flavonoid Sulfotransferase," *Anal Biochem* 161:176-180 (1987).

Walle, "Absorption and Metabolism of Flavonoids," *Free Radical Biol Med.* 36(7):829-837 (2004).

English language Derwent abstract for CN 1067070.
English language Derwent abstract for JP 6080656.
English language Derwent abstract for JP 7041442.
English language Derwent abstract for JP 7061942.
English language Derwent abstract for JP 7118241.
English language Derwent abstract for JP 7179380.
English language Derwent abstract for JP 7233109.
English language Derwent abstract for JP 7247289.
English language Derwent abstract for JP 2002/249483.
English language Derwent abstract for JP 2004/307440.

Co-pending U.S. Appl. No. 11/255,103, filed Oct. 20, 2005, Inventors: Norman C.W. Wong et al.

Kawamatsu et al., "2-Amino-4-phenylthiazole derivatives as anti-atherogenic agents" *Eur. J. Med. Chem.* 16(4): 355-362 (1981).

Maher et al., "Lipoprotein (a) and coronary heart disease" *Curr. Opin. Lipidol.* 6:229-235 (1995).

Tait et al., "Synthesis and Free Radical Scavenging Activity of 4-(2H-1,2,4-Benzothiadiazine-1,1-dioxide-3-yl)-2,6-bis(1,1-dimethylethyl)phenols" *Tetrahedron* 52(38):12587-12596 (1996).

Utermann, "The Mysteries of Lipoprotein(a)" *Science* 246:904-910 (1999).

Abdel-Jalil, R.J. et al. "Synthesis and Antitumor Activity of 2-Aryl-7-fluoro-6-(4-methyl-1-piperazinyl)-4(3H)-quinazolinones" *Heterocycles* 65(9):2061-2070 (2005).

Abdul-Rahman, A. et al. "Dinuclear molybdenum complexes derived from diphenols: electrochemical interactions and reduced species" *Polyhedron* 16(24):4353-4362 (1997).

Baba, S. et al. "Continuous intake of polyphenolic compounds containing cocoa powder reduces LDL oxidative susceptibility and has beneficial effects on plasma HDL-cholesterol concentrations in humans" *Am. J. Clin. Nutr.* 85:709-717 (2007).

Bayly, S.R. et al. "Electronic and magnetic metal-metal interactions in dinuclear oxomolybdenum(V) complexes across bis-phenolate bridging ligands with different spacers between the pholate termini:

ligand-centered vs. metal-centered redox activity" *J. Chem. Soc., Dalton Transactions* 9:1401-1414 (2001).
Bhilare, S.V. et al. "Ionic-Liquid-Influenced Expeditious and Stereoselective Synthesis of Olefins" *Synthetic Communications* 37(18):3111-3117 (2007).
Buhle, E.L. et al. "Trivalent carbon. II. Unsymmetrical hexaaryldimethylperoxides" *J. Am. Chem. Soc.* 65:584-586 (1943).
Cooper, K.A. et al. "Wine polyphenols and promotion of cardiac health" *Nutr. Res. Rev.* 17:111-129 (2004).
Co-pending U.S. Appl. No. 10/575,406, filed Nov. 1, 2006, entitled "Treatment of Diseases Associated With the Egr-1 Enhancer Element" Inventors: Norman C.W. Wong et al.
Co-pending U.S. Appl. No. 11/670,238, filed Feb. 1, 2007, entitled "Compounds for the Prevention and Treatment of Cardiovascular Diseases" Inventors: Norman C.W. Wong et al.
Co-pending U.S. Appl. No. 11/990,162, filed Feb. 7, 2008, entitled "Pharmaceutical Compositions for the Prevention and Treatment of Complex Diseases and Their Delivery By Insertable Medical Devices" Inventors: Norman C.W. Wong et al.
Eiden, F. et al. "1,2-Bisbenzopyranyl-ethane" *Archiv der Pharmazie* 313(2):120-128 (1980) (German).
English language Derwent abstract for EP 20005941, 4 pages (2009).
English language Derwent abstract for JP 7-247289, 1 page (1995).
English language Derwent abstract for JP 10-287678, 1 page (1999).
English language Derwent abstract for JP 2004-203751, 3 pages (no date).
Fieser, L.F. "Potentials of some unstable oxidation-reduction systems" *J. Am. Chem. Soc.* 52:4915-4940 (1930).
Guillory, J.K. "Generation of Polymorphs, Hydrates, Solvates, and Amorphous Solids" Brittain, Harry G. (ed.) *Polymorphism in Pharmaceutical Solids* vol. 95, Marcel Dekker, Inc., New York; pp. 202-208 (1999).
Hemingway, R.W. et al. "A Gas-liquid chromatographic examination of stilbene derivatives" *J. Chromatography* 50(3):391-399 (1970).
Linnell, W.H. "Isomers of stilboestrol. Part II." *Q. J. Pharm. Pharmacol.* 15:384-388 (1942).
Lopez, S.E. et al. "The Synthesis of Substituted 2-Aryl-4(3H)-quinazolinones Using NaHSO$_3$/DMA. Steric Effect Upon the Cyclisation-Dehydrogenation Step" *J. Chem. Research (S)* pp. 258-259 (2000).
Mahto, R.P. et al. "Synthesis of 3-Aryl-7-hydroxy Isochromenes" *Asian J. Chem.* 11(2):431-435 (1999).
Mckee et al. "Some Basically Substituted Quinazolines" *J. Am. Chem. Soc.* 68(10):1902-1903 (1946).
Melani, F. et al. "Tricyclic heterocyclic systems: pyrazolo[5',4':4,5]- and pyrazolo-[3',4':4,5]pyrano[2,3-b]pyridine derivatives" *J. Heterocyclic Chem.* 25:1367 (1988).
Ordovas, J.M. "Gene-diet interaction and plasma lipid responses to dietary intervention" *Biochemical Society Transactions* 30(2):68-73 (2002).
Quinones, A. et al. "The *egr*-1 gene is induced by DNA-damaging agents and non-genotoxic drugs in both normal and neoplastic human cells" *Life Sciences* 72(26):2975-2992 (2003).
Ragione, F.D. et al. "Antioxidants induce different phenotypes by a distinct modulation of signal transduction" *FEBS Letters* 523:289-294 (2002).
Ragione, F.D. et al. "p21$^{Cip1}$ Gene Expression Is Modulated by Egr1: A Novel Regulatory Mechanism Involved in the Resveratrol Antiproliferative Effect" *J. Biol. Chem.* 278:23360-23368 (2003).
Rajakumar, P. et al. "TiCl$_4$-dioxane—A facile and efficient system for de-*O*-benzylation, de-*O*-allylation, and de-*O*-xylylation of phenolic ethers" *Synthetic Communications* 33(22):3891-3896 (2003).
Richtzenhain, H. "Estrogenic stilbene and diphenylethane derivatives. II." *Chemische Berichte* 82:405-407 (1949) (German).
Schultz, T.P. et al. "Role of stilbenes in the natural durability of wood: fungicidal structure-activity relationships" *Phytochemistry* 29(5):1501-1507 (1990).
Sieber, R.H. "Reactions of chloroacetaldehyde with aromatic hydrocarbons, phenols, and phenol ethers" *Justus Liebigs Annalen der Chemie* 730:31-46 (1969) (German).

Sliwa, H. et al. "Tautomerie entre structures a-enaminocetone et b-ceto iminoether presentee par les piperidines resultant de la semihydrogenation d'alcoxy-2-acyl-3 pyridines" *J. Heterocyclic Chem.* 16:969 (1979) (French).
Smyth, M.S. et al. "Non-amine based analogs of lavendustin A as protein-tyrosine kinase inhibitors" *J. Med. Chem.* 36(20):3010-3014 (1993).
Yamakoshi, J. et al. "Isoflavone aglycone-rich extract without soy protein attenuates atherosclerosis development in cholesterol-fed rabbits" *J Nutr* 130(8):1887-1893 (2000).
Yoshioka, N. et al. "Semiempirical Investigation of Stilbene-Linked Diradicals and Magnetic Study of Their Bis(N-tert-butylnitroxide) Variants" *J. Org. Chem.* 59(15):4272-4280 (1994).
Laarhoven, W.H. et al. "Influence of non-planarity in styrene and stilbene derivatives. IV. Syntheses, infrared spectra, and molecular refractions of some sterically hindered p,p'-dimethoxystilbenes" *Recueil des Travaux Chimiques des Pays-Bas* 80:775-791 (1961).
Kawamatsu et al., "2-Amino-4-Phenylthiazole Derivatives as Anti-Atherogenic Agents," *Eur. J. Med. Chem.*, 16(4):355-362 (1981).
Patent Abstracts of Japan English language abstract of JP 2001/131151.
Patent Abstracts of Japan English language abstract of JP 2001/335476.
Patent Abstracts of Japan English language abstract of JP 2001/139550.
Rimando et al., "Pterostilbene, a New Agonist for the Peroxisome Proliferator-Activated Receptor Alpha-Isoform, Lowers Plasma Lipoproteins and Cholesterol in Hypocholesterolemic Hamsters," *Journal of Agricultural and Food Chemistry*, 53(9):3403-3407 (2005).
International Search Report for priority application PCT/US2005/037719, dated Feb. 2, 2007.
Chakrabarty et al., "Induction of apoptosis in human cancer cell lines by diospyrin, a plant-derived bisnaphthoquinonoid, and its synthetic derivatives," *Cancer Letters* 188(1-2):85-93 (2002).
English language Derwent Abstract of DE 36 01 417.
English language Derwent Abstract of EP 0 210 342.
English language Derwent Abstract of EP 0 564 350.
English language Derwent Abstract of FR 2 244 493.
Gerritsen et al., "Flavenoids inhibit cytokine-induced endothelial cell adhesion protein gene expression," *Am. J. Pathol.* 147(2):278-292 (1995).
Hazra et al., "New diospyrin derivatives with improved tumour inhibitory activity towards ehrlich ascites carcinoma," *Medical Science Research* 22(5):351-353 (1994).
Hazra et al., "Synthesis of an antitumor derivative of diospyrin," *IRCS Medical Science* 14(1):35-36 (1986).
International Search Report and Written Opinion as issued in International Application No. PCT/CA2007/000146 mailed on Oct. 29, 2007.
International Search Report and Written Opinion as issued in International Application No. PCT/US2006/029827 mailed on Apr. 16, 2007.
International Search Report and Written Opinion as issued in International Application No. PCT/US2005/038048 mailed on Mar. 7, 2007.
Jeong et al., "Hypocholesterolemic activity of hesperetin derivatives," *Bioorg. Med. Chem. Lett.* 13:2663-2665 (2003).
Jin et al., "Antiplatelet and antithrombotic activities of CP201, a newly synthesized 1,4-naphthoquinone derivative," *Vasc. Pharmacol.* 41(1):35-41 (2004).
Kublak et al., "The preparation of the azaspirobicyclic system of discorhabdin c via an Intramolecular phenolate alkylation," *Tetrahedron Lett.* 31(27):3845-3848 (1990).
Lamon-Fava, "Genistein activates apolipoprotein A-I gene expression in the human hepatoma cell line Hep G2," J. Nutrition 130:2489-2492 (2000).
Lin et al. "Potential bioreductive alkylating agents. 7. Antitumor effects of phenyl-substituted 2-chloromethyl-3-phenyl-1,4-naphthoquinones," *J. Med. Chem.* 19(11):1336-1338 (1976).
Meckes et al., "The effects of chrysin and pinostrobin, 2 flavonoids isolated from teloxys graveolens leaves, on isolated guinea-pig ileum," *Phytomedicine* 5(6):459-463 (1998).

Middleton et al., "Quercetin inhibits lipopolysaccharide-induced expression of endothelial cell intracellular adhesion molecule-1," *Int. Archives of Allergy and Immunology* 107(1/3):435-436 (1995).

Theriault et al., "Modulation of hepatic lipoprotein synthesis and secretion by taxifolin, a plant flavonoid," *J. Lipid Res.* 41:1969-1979 (2000).

U.S. Appl. No. 11/670,238, entitled Compounds for the Prevention and Treatment of Cardiovascular Diseases, filed Feb. 1, 2007.

U.S. Appl. No. 11/990,162, entitled Pharmaceutical Compositions for the Prevention and Treatment of Complex Diseases and Delivery by Insertable Medical Devices, filed Feb. 7, 2008.

Woelle et al., Selective inhibition of tumor necrosis factor-induced vascular cell adhesion molecule-1 gene expression by a novel flavonoid: lack of effect on transcription factor NF-kappa-B, *Arterioscler. Thromb. Vasc. Biol.* 16(12):1501-1508 (1996).

Wurm et al., "1,4-Naphthoquinones, XXVI: Phenyl-1,4-naphthoquinone derivatives with the hydroxylation patterns of bioflavonoids," *Pharmazie* 52(10):739 (1997).

Wurm, "1 4 naphthoquinones XXI. 2-3 5 di-tert-butyl-4-hydroxyphenyl-1 4-naphtoquinones as 5 lipozxygenase inhibitors," *Archiv der Pharmazie* 324(8):491-495 (1991).

Yardley et al., "In vitro activity of diospyrin and derivatives against leishmania donovani, trypanosoma cruzi and trypanosoma brucei brucei," *Phytotherapy Research* 10(7):559-562 (1996).

\* cited by examiner

STILBENES AND CHALCONES FOR THE PREVENTION AND TREATMENT OF CARDIOVASCULAR DISEASES

CROSS-REFERENCE TO RELATED APPLICATIONS

This application claims the benefit of U.S. provisional application Ser. No. 60/620,888, filed Oct. 20, 2004; U.S. provisional application Ser. No. 60/626,819, filed Nov. 10, 2004; and U.S. provisional application Ser. No. 60/665,859, filed Mar. 29, 2005, each of which is incorporated herein by reference in its entirety.

TECHNICAL FIELD

The present disclosure relates to polyphenol compounds, which are useful for regulating the expression of apolipoprotein A-I (ApoA-l), and their use for treatment and prevention of cardiovascular disease and related disease states, including cholesterol or lipid related disorders, such as, e.g., atherosclerosis.

BACKGROUND

Epidemiologic data demonstrate an inverse relationship between circulating levels of high density lipoprotein cholesterol (HDL-C) and the incidence of clinically significant atherosclerosis. Each 1 mg/dl increment in the HDL-C serum level is associated with a 2-3% decrement in cardiovascular risk; a 1% reduction in LDL-C reduces coronary heart disease (CHD) risk by 2%. Gordon et al., *Am. J. Med.* 62(5):707-14 (1997). Experimental evidence further supports the protective effect of HDL against cardiovascular disease. For example, in subjects with low HDL-C, administration of gemfibrozil results in a 6% increase in the HDL-C level and a corresponding 22% reduction of the CHD risk Rubins et al., *N. Engl. J. Med.* 341(6):410-8 (1999). Observations in genetic disorders associated with low HDL due to reduced ApoA-I expression, also indicate the link between elevated risk of CHD and low HDL-C.

HDL appears to exert its antiatherogenic effect by mediating reverse cholesterol transport (RCT), in which cholesterol is recruited from peripheral tissues and transported to the liver. In addition, HDL also exerts anti-inflammatory, antioxidant effects and promotes fibrinolysis. HDL paticles protect against oxidation of LDL, an important initial step in promoting cholseteol uptake by arterial macrophages. HDL exists in two main forms, one containing both apolipoprotein A-I (ApoA-II) and apolipoprotein A-II (ApoA-II), and the other containing ApoA-I without ApoA-II. Schultz et al., *Nature* 365(6448):762-4 (1993). The cardioprotective effect of HDL is mostly, but not exclusively, attributable to ApoA-I.

Clinical and experimental data suggest that the production of ApoA-I is a critical determinant of circulating HDL. For example, persons with familial hyperalphalipoproteinemia (elevated ApoA-I) appear to be protected from atherosclerosis, while those deficient in ApoA-I (hypoalphalipoproteinemia) show accelerated cardiovascular disease. In addition, various experimental manipulations to increase production of ApoA-I are associated with reduced atherogenicity. For example, human ApoA-I is protective in transgenic animal models (Shah et al., *Circulation* 97(8):780-5 (1998); Rubin et al., *Nature* 353(6341):265-7 (1991)), and treatment with ApoA-I$_{Milano}$ prevents atherosclerotic lesions and leads to regression of atherosclerotic plaques in human patients (Nissen et al., *JAMA* 290(17):2292-300 (2003)). Further lines of research supporting an antiatherogenic role of ApoA-I, include: enhancement of reverse cholesterol transport, attenuation of oxidative stress, increased peroxonase activity, enhanced anticoagulant activity, and anti-inflammatory activity. Accordingly, ApoA-I is an attractive target for therapeutic intervention.

Currently available therapeutic agents that increase the plasma concentration of ApoA-I, for example, recombinant ApoA-I or peptides that mimic ApoA-I, have potential drawbacks related to manufacturing and reproducibility, e.g., stability during storage, delivery of an active product, and in vivo half-life. Therefore, small molecule compounds that upregulate the production of endogenous ApoA-I, such as, e.g., transcriptional upregulators of ApoA-I expression, are very attractive as new therapeutic agents for cardiovascular disease.

One class of compounds that are thought to contribute to the prevention of various diseases, including cancer and cardiovascular diseases, is polyphenols. Polyphenols are common constituents of the human diet, present in most food and beverages of plant origin, and are the most abundant dietary antioxidants. However, polyphenols protective properties are often minimized due to poor bioavailability, lack of clinical significance, and deleterious effects at high concentrations. For example, the most abundant and available source of resveratrol for consumers, red wine, cannot be consumed in therapeutically efficacious quantities on a daily basis due to the numerous well documented deleterious effects of excessive alcohol consumption. The actions of resveratrol may be better or safer in the absence of alcohol.

Several human clinical studies, involving foods or beverages, have yet to demonstrate an unequivocal benefit on primary clinical endpoints, such as oxidative stress, lipemia and inflammation. For example, out of 12 recent intervention studies with differing polyphenol sources; 6 showed no effect on lipid parameters and the other 6 showed an improvement in the lipid parameters. Manach, *Curr. Opin. Lipidol.* 16(1):77-84 (2005). Such contradictory data has limited the potential use of polyphenols, despite their many beneficial properties.

The use of naturally occurring polyphenols as a potential therapy has also been impeded by the inability to achieve efficacious levels of bioavailability. The bioavailability of polyphenols in humans range from 1% to 26% and has a large inter-individual variability as well as variability between different polyphenols. Polyphenols differ in how they are absorbed, metabolized, and excreted. For example, polyphenol flavonoids, such as quercetin, have been reported to have less than 1% intestinal absorption following oral administration. Gugler et al., *Eur. J. Clin. Pharm.* 9:223 (1975). In addition, metabolites are known to negatively influence the biological activity of the parent compounds. Such metabolites often differ from the parent compound in terms of toxicity, efficacy and length of residence in the plasma. Another limiting factor may be polyphenols' poor solubility in water which limits the routes of administration. These and other factors have made it difficult to determine appropriate dosages of the naturally occurring polyphenols, naringenin or resveratrol, for use in humans.

Thus, there exists a need for synthetic polyphenols to be developed as therapeutic agents for the treatment and prevention of cardiovascular and related diseases, particularly, cholesterol or lipid related disorders, such as, e.g., atherosclerosis. It is therefore one of the objects of the present invention to provide compounds that upregulate the expression of ApoA-I, while having more favorable pharmacological properties than naturally occurring polyphenols.

SUMMARY

The methods of invention include administering to a mammal (e.g., a human) in need thereof a therapeutically effective amount of a stilbene compound of Formula I:

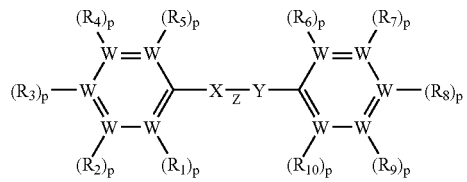

Formula I wherein:

X is selected from C, $CR_{11}$, $CR_{11}R_{13}$, CO, CS, O, S, SO, $SO_2$, N and $NR_{11}$, wherein $R_{11}$ may be the same or different than $R_{13}$;

Y is selected from C, $CR_{12}$, $CR_{12}R_{14}$, CO, CS, O, S, SO, $SO_2$, N and $NR_{12}$, wherein $R_{12}$ may be the same or different than $R_{14}$;

$R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ are each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone, or two adjacent substituents selected from $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ are connected in a 5 or 6-membered ring to form a bicyclic aryl or bicyclic heteroaryl;

each W is independently selected from C and N, wherein if W is N, then p is 0 and if W is C, then p is 1;

Z is selected from a single bond, a double bond and a triple bond;

and pharmaceutically acceptable salts and hydrates thereof;

wherein if $R_3$ and $R_8$ are each hydroxyl, then at least one of $R_{11}$ and $R_{12}$ is not alkyl;

wherein if Z is a double bond, then $R_2$, $R_4$ and $R_8$ are not each hydroxyl; and wherein if Formula 1 has the structure:

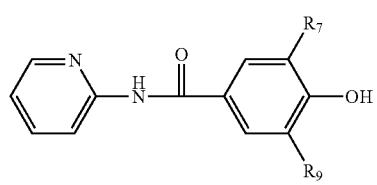

then at least one of $R_7$ and $R_9$ is not alkyl.

Methods of invention also include administering to a mammal (e.g., a human) in need thereof a therapeutically effective amount of a chalcone compound of Formula IV:

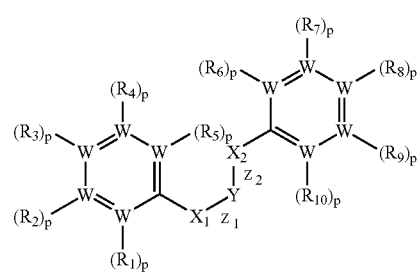

Formula IV wherein:

$X_1$ is selected from C, $CR_{11}$, $CR_{11}R_{13}$, CO, CS, O, S, SO, $SO_2$, N and $NR_{11}$, wherein $R_{11}$ may be the same or different than $R_{13}$;

$X_2$ is selected from C, $CR_{17}$, $CR_{17}R_{18}$, CO, CS, O, S, SO, $SO_2$, N and $NR_{17}$, wherein $R_{17}$ may be the same or different than $R_{18}$;

Y is selected from C, $CR_{12}$, $CR_{12}R_{14}$, CO, CS, S, SO, $SO_2$, N and $NR_{12}$, wherein $R_{12}$ may be the same or different than $R_{14}$;

$R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{17}$ and $R_{18}$ are each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone, or two adjacent substituents selected from $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{17}$ and $R_{18}$ are connected in a 5 or 6-membered ring to form a bicyclic aryl or bicyclic heteroaryl;

each W is independently selected from C and N, wherein if W is N, then p is 0 and if W is C, then p is 1;

$Z_1$ and $Z_2$ are each independently selected from a single bond, a double bond, and a triple bond;

and pharmaceutically acceptable salts and hydrates thereof.

In certain embodiments, the methods and compositions of the invention are useful for treatment of diseases characterized by reduced ApoA-I and/or HDL. The compounds and compositions of the invention can be used to increase expression of ApoA-I. Increasing expression of ApoA-I refers to transcriptionally modulating the expression of the ApoA-I gene thereby affecting the level of the ApoA-I protein expressed, i.e., synthesized and secreted, by the cell. An increase in ApoA-I protein expression leads to an increase in blood levels of HDL. Thus, the methods and compounds of the invention may further be used to reduce plasma cholesterol levels. Accordingly, the methods and compositions of the invention can be used for treatment and prevention of cardiovascular disease and related disease states, particularly, cholesterol or lipid related disorders, such as, atherosclerosis, dyslipidemias, dyslipoproteinemias, hypertension, coronary artery disease, cerebrovascular disease, and the like.

In one aspect, the invention provides a method for prevention of arteriosclerosis lesion development in a mammal, including the development of new arteriosclerotic lesions. In another aspect, the present invention provides a method regressing arteriosclerosis lesions.

The methods and compounds of the invention may further be used to lower blood levels of LDL and triglycerides and/or to increase free radical scavenging. In addition, these methods and compositions may also be used to inhibit HMG-CoA reductase, inhibit ACAT, and/or increase ABCA-I activity.

In a further aspect, the invention provides methods and compositions for effecting an increase of HDL in a mammal comprising, wherein the compound is a stilbene or a chalcone, each derivatized with covalently bonded niacin. In certain embodiments, the covalent bond comprises a reverse ester linkage.

DETAILED DESCRIPTION

Definitions

The term "aldehyde" or "formyl" as used herein refers to the radical —CHO.

The term "alkenyl" as used herein refers to an unsaturated straight or branched hydrocarbon having at least one carbon-carbon double bond, such as a straight or branched group of 2-22, 2-8, or 2-6 carbon atoms, referred to herein as $(C_2-C_{22})$ alkenyl, $(C_2-C_8)$alkenyl, and $(C_2-C_6)$alkenyl, respectively. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, etc.

The term "alkoxy" as used herein refers to an alkyl group attached to an oxygen (—O-alkyl-). "Alkoxy" groups also include an alkenyl group attached to an oxygen ("alkenoxy") or an alkynyl group attached to an oxygen ("alkynoxy") groups. Exemplary alkoxy groups include, but are not limited to, groups with an alkyl, alkenyl or alkynyl group of 1-22, 1-8, or 1-6 carbon atoms, referred to herein as $(C_1-C_{22})$alkoxy, $(C_1-C_8)$alkoxy, and $(C_1-C_6)$alkoxy, respectively. Exemplary alkoxy groups include, but are not limited to methoxy, ethoxy, etc.

The term "alkyl" as used herein refers to a saturated straight or branched hydrocarbon, such as a straight or branched group of 1-22, 1-8, or 1-6 carbon atoms, referred to herein as $(C_1-C_{22})$alkyl, $(C_1-C_8)$alkyl, and $(C_1-C_6)$alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "alkynyl" as used herein refers to an unsaturated straight or branched hydrocarbon having at least one carbon-carbon triple bond, such as a straight or branched group of 2-22, 2-8, or 2-6 carbon atoms, referred to herein as $(C_2-C_{22})$alkynyl, $(C_2-C_8)$alkynyl, and $(C_2-C_6)$alkynyl, respectively. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl, etc.

The term "amide" as used herein refers to a radical of the form —$R_aC(O)N(R_b)$—, —$R_aC(O)N(R_b)R_c$—, or —C(O)$NR_bR_c$, wherein $R_b$ and $R_c$ are each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone. The amide can be attached to another group through the carbon, the nitrogen, $R_b$, $R_c$, or $R_a$. The amide also may be cyclic, for example $R_b$ and $R_c$, $R_a$ and $R_b$, or $R_a$ and $R_c$ may be joined to form a 3- to 12-membered ring, such as a 3- to 10-membered ring or a 5- to 6-membered ring. The term "amide" encompasses groups such as sulfonamide, urea, carbamate, carbamic acid, and cyclic versions thereof. The term "amide" also encompasses an amide group attached to a carboxy group, e.g., -amide-COOH or salts such as -amide-COONa, etc., an amino group attached to a carboxy group, e.g., -amino-COOH or salts such as -amino-COONa, etc.

The term "amine" or "amino" as used herein refers to a radical of the form —$NR_dR_e$, —$N(R_d)R_e$—, or —$R_eN(R_d)R_f$— where $R_d$, $R_e$, and $R_f$ are independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone. The amino can be attached to the parent molecular group through the nitrogen, $R_d$, $R_e$ or $R_f$. The amino also may be cyclic, for example any two of $R_a$, $R_b$, and $R_c$ may be joined together or with the N to form a 3- to 12-membered ring, e.g., morpholino or piperidinyl. The term amino also includes the corresponding quaternary ammonium salt of any amino group, e.g., —[$N(R_d)(R_e)(R_f)$]$^+$. Exemplary amino groups include aminoalkyl groups, wherein at least one of $R_d$, $R_e$, or $R_f$ is an alkyl group.

The term "aryl" as used herein refers to a mono-, bi-, or other multi-carbocyclic, aromatic ring system. The aryl group can optionally be fused to one or more rings selected from aryls, cycloalkyls, and heterocyclyls. The aryl groups of this invention can be substituted with groups selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Exemplary aryl groups also include, but are not limited to a monocyclic aromatic ring system, wherein the ring comprises 6 carbon atoms, referred to herein as "$(C_6)$ aryl."

The term "arylalkyl" as used herein refers to an aryl group having at least one alkyl substituent, e.g. -aryl-alkyl-. Exemplary arylalkyl groups include, but are not limited to, arylalkyls having a monocyclic aromatic ring system, wherein the ring comprises 6 carbon atoms, referred to herein as "$(C_6)$ arylalkyl."

The term "aryloxy" as used herein refers to an aryl group attached to an oxygen atom. Exemplary aryloxy groups include, but are not limited to, aryloxys having a monocyclic aromatic ring system, wherein the ring comprises 6 carbon atoms, referred to herein as "$(C_6)$aryloxy."

The term "arylthio" as used herein refers to an aryl group attached to an sulfur atom. Exemplary arylthio groups include, but are not limited to, arylthios having a monocyclic aromatic ring system, wherein the ring comprises 6 carbon atoms, referred to herein as "$(C_6)$arylthio."

The term "arylsulfonyl" as used herein refers to an aryl group attached to a sulfonyl group, e.g., —$S(O)_2$-aryl-. Exemplary arylsulfonyl groups include, but are not limited to, arylsulfonyls having a monocyclic aromatic ring system, wherein the ring comprises 6 carbon atoms, referred to herein as "$(C_6)$arylsulfonyl."

The term "benzyl" as used herein refers to the group —$CH_2$-phenyl.

The term "bicyclic aryl" as used herein refers to an aryl group fused to another aromatic or non-aromatic carbocyclic or heterocyclic ring. Exemplary bicyclic aryl groups include, but are not limited to, naphthyl or partly reduced forms thereof, such as di-, tetra-, or hexahydronaphthyl.

The term "bicyclic heteroaryl" as used herein refers to a heteroaryl group fused to another aromatic or non-aromatic carbocylic or heterocyclic ring. Exemplary bicyclic heteroaryls include, but are not limited to, 5,6 or 6,6-fused systems wherein one or both rings contain heteroatoms. The term "bicyclic heteroaryl" also encompasses reduced or partly reduced forms of fused aromatic system wherein one or both rings contain ring heteroatoms. The ring system may contain up to three heteroatoms, independently selected from oxygen, nitrogen, or sulfur. The bicyclic system may be optionally substituted with one or more groups selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Exemplary bicyclic heteroaryl's include, but are not limited to, quinazolinyl, benzothiophenyl, benzoxazolyl, benzimidazolyl, benzothiazolyl, benzofuranyl, indolyl, quinolinyl, isoquinolinyl, phthalazinyl, benzotriazolyl, benzopyridinyl, and benzofuranyl.

The term "carbamate" as used herein refers to a radical of the form —$R_g$OC(O)N($R_h$)—, —$R_g$OC(O)N($R_h$)$R_i$—, or —OC(O)N$R_h R_i$, wherein $R_g$, $R_h$ and $R_i$ are each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone. Exemplary carbamates include, but are not limited to, arylcarbamates or heteroaryl carbamates, e.g. wherein at least one of $R_g$ $R_h$ and $R_i$ are independently selected from aryl or heteroaryl, such as pyridine, pyridazine, pyrimidine, and pyrazine.

The term "carbonyl" as used herein refers to the radical —C(O)—.

The term "carboxy" as used herein refers to the radical —COOH or its corresponding salts, e.g. —COONa, etc. The term carboxy also includes "carboxycarbonyl," e.g. a carboxy group attached to a carbonyl group, e.g., —C(O)—COOH or salts such as —C(O)—COONa, etc.

The term "cyano" as used herein refers to the radical —CN.

The term "cycloalkoxy" as used herein refers to a cycloalkyl group attached to an oxygen.

The term "cycloalkyl" as used herein refers to a monovalent saturated or unsaturated cyclic, bicyclic, or bridged bicyclic hydrocarbon group of 3-12 carbons, or 3-8 carbons, referred to herein as "($C_3$-$C_8$)cycloalkyl," derived from a cycloalkane. Exemplary cycloalkyl groups include, but are not limited to, cyclohexanes, cyclohexenes, cyclopentanes, and cyclopentenes. Cycloalkyl groups may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Cycloalkyl groups can be fused to other cycloalkyl, aryl, or heterocyclyl groups.

The term "dicarboxylic acid" as used herein refers to a group containing at least two carboxylic acid groups such as saturated and unsaturated hydrocarbon dicarboxylic acids and salts thereof. Exemplary dicarboxylic acids include alkyl dicarboxylic acids. Dicarboxylic acids may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone. Dicarboxylic acids include, but are not limited to succinic acid, glutaric acid, adipic acid, suberic acid, sebacic acid, azelaic acid, maleic acid, phthalic acid, aspartic acid, glutamic acid, malonic acid, fumaric acid, (+)/(−)-malic acid, (+)/(−) tartaric acid, isophthalic acid, and terephthalic acid. Dicarboxylic acids further include carboxylic acid derivatives thereof, such as anhydrides, imides, hydrazides, etc., for example, succinic anhydride, succinimide, etc.

The term ("ester" refers to a radical having the structure —C(O)O—, —C(O)O—$R_j$, —$R_k$C(O)O—$R_j$—, or —$R_k$C(O)O—, where O is not bound to hydrogen, and $R_j$ and $R_k$ can independently be selected from alkoxy, aryloxy, alkyl, alkenyl, alkynyl, amide, amino, aryl, arylalkyl, cycloalkyl, ether, formyl, haloalkyl, halogen, heteroaryl, heterocyclyl, ketone, phosphate, sulfide, sulfinyl, sulfonyl, sulfonic acid and thioketone. $R_k$ can be a hydrogen, but $R_j$ cannot be hydrogen. The ester may be cyclic, for example the carbon atom and $R_j$, the oxygen atom and $R_k$, or $R_j$ and $R_k$ may be joined to form a 3- to 1 2-membered ring. Exemplary esters include, but are not limited to, alkyl esters wherein at least one of $R_j$ or $R_k$ is alkyl, such as -alkyl-C(O)—O—, —C(O)—O-alkyl-, -alkyl-C(O)—O-alkyl-, etc. Exemplary esters also include aryl or heteoraryl esters, e.g. wherein at least one of $R_j$ or $R_k$ is a heteroaryl group such as pyridine, pyridazine, pyrmidine and pyrazine, such as a nicotinate ester. Exemplary esters also include reverse esters having the structure —$R_k$C(O)O—, where the oxygen is bound to the parent molecular group. Exemplary reverse esters include succinate, D-argininate, L-argininate, L-lysinate and D-lysinate. Esters also include carboxylic acid anhydrides and acid halides.

The term ("ether" refers to a radical having the structure —$R_l$O—$R_m$—, where $R_l$ and $R_m$ can independently be alkyl, alkenyl, alkynyl, aryl, cycloalkyl, heterocyclyl, or ether. The ether can be attached to the parent molecular group through $R_l$ or $R_m$. Exemplary ethers include, but are not limited to, alkoxyalkyl and alkoxyaryl groups. Ethers also includes polyethers, e.g., where one or both of $R_l$ and $R_m$ are ethers.

The terms "halo" or "halogen" or "Hal" as used herein refer to F, Cl, Br, or I.

The term "haloalkyl" as used herein refers to an alkyl group substituted with one or more halogen atoms. "Haloalkyls" also encompass alkenyl or alkynyl groups substituted with one or more halogen atoms.

The term "heteroaryl" as used herein refers to a mono-, bi-, or multi-cyclic, aromatic ring system containing one or more heteroatoms, for example 1 to 3 heteroatoms, such as nitrogen, oxygen, and sulfur. Heteroaryls can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heteroaryls can also be fused to non-aromatic rings. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidilyl, tetrazolyl, furyl, thienyl, isoxazolyl, thiazolyl, furyl, phenyl, isoxazolyl, and oxazolyl. Exemplary heteroaryl groups include, but are not limited to, a monocyclic aromatic ring, wherein the ring comprises 2 to 5 carbon atoms and 1 to 3 heteroatoms, referred to herein as "($C_2$-$C_5$)heteroaryl."

The terms "heterocycle," "heterocyclyl," or "heterocyclic" as used herein refer to a saturated or unsaturated 3-, 4-, 5-, 6- or 7-membered ring containing one, two, or three heteroatoms independently selected from nitrogen, oxygen, and sulfur. Heterocycles can be aromatic (heteroaryls) or non-aromatic. Heterocycles can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone.

Heterocycles also include bicyclic, tricyclic, and tetracyclic groups in which any of the above heterocyclic rings is fused to one or two rings independently selected from aryls, cycloalkyls, and heterocycles. Exemplary heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolidin-2-onyl, pyrrolinyl, pyrrolyl, quinolinyl, quinoxaloyl, tetrahydrofuryl, tetrahydroisoquinolyl, tetrahydropyranyl, tetrahydroquinolyl, tetrazolyl, thiadiazolyl, thiazolidinyl, thiazolyl, thienyl, thiomorpholinyl, thiopyranyl, and triazolyl.

The terms "hydroxy" and "hydroxyl" as used herein refers to the radical —OH.

The term "hydroxyalkyl" as used herein refers to a hydroxy radical attached to an alkyl group.

The term "hydroxyaryl" as used herein refers to a hydroxy radical attached to an aryl group.

The term "ketone" as used herein refers to a radical having the structure —C(O)—Rn (such as acetyl, —C(O)CH$_3$) or —R$_n$—C(O)—R$_o$—. The ketone can be attached to another group through R$_n$ or R$_o$. R$_n$ or R$_o$ can be alkyl, alkenyl, alkynyl, cycloalkyl, heterocyclyl or aryl, or R$_n$ or R$_o$ can be joined to form a 3- to 12-membered ring.

The term "monoester" as used herein refers to an analogue of a dicarboxylic acid wherein one of the carboxylic acids is functionalized as an ester and the other carboxylic acid is a free carboxylic acid or salt of a carboxylic acid. Examples of monoesters include, but are not limited to, to monoesters of succinic acid, glutaric acid, adipic acid, suberic acid, sebacic acid, azelaic acid, oxalic and maleic acid.

The term "nitro" as used herein refers to the radical —NO$_2$.

The term "perfluoroalkoxy" as used herein refers to an alkoxy group in which all of the hydrogen atoms have been replaced by fluorine atoms.

The term "perfluoroalkyl" as used herein refers to an alkyl group in which all of the hydrogen atoms have been replaced by fluorine atoms. Exemplary perfluroalkyl groups include, but are not limited to, C$_{1-5}$ perfluoroalkyl, such as trifluoromethyl, etc.

The term "perfluorocycloalkyl" as used herein refers to a cycloalkyl group in which all of the hydrogen atoms have been replaced by fluorine atoms.

The term "phenyl" as used herein refers to a 6-membered carbocyclic aromatic ring. The phenyl group can also be fused to a cyclohexane or cyclopentane ring. Phenyl can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone.

The term "phosphate" as used herein refers to a radical having the structure —OP(O)O$_2$—, —R$_x$OP(O)O$_2$—, —OP(O)O$_2$R$_y$—, or —R$_x$OP(O)O$_2$R$_y$—, wherein Rx and R$_y$ can be alkyl, alkenyl, alkynyl, alkoxy, amide, amino, aryl, aryloxy, carboxy, cyano, cycloalkyl, ester, ether, halogen, heterocyclyl, hydrogen, hydroxy, ketone, nitro, sulfonate, sulfonyl, and thio.

The term "sulfide" as used herein refers to the radical having the structure R$_z$S—, where R$_z$ can be alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, and ketone. The term "alkylsulfide" as used herein refers to an alkyl group attached to a sulfur atom.

The term "sulfinyl" as used herein refers to a radical having the structure —S(O)O—, —R$_p$S(O)O—, —R$_p$S(O)OR$_q$—, or —S(O)OR$_q$—, wherein R$_p$ and R$_s$ can be alkoxy, aryloxy, alkyl, alkenyl, alkynyl, amide, amino, aryl, arylalkyl, cycloalkyl, ester, ether, formyl, halogen, haloalkyl, heteroaryl, heterocyclyl, hydroxyl, ketone, nitro, phosphate, sulfide, sulfonyl, sulfonic acid, sulfonamide and thioketone. Exemplary sulfinyl groups include, but are not limited to, alkylsulfinyls wherein at least one of R$_p$ or R$_q$ is alkyl, alkenyl or alkynyl.

The term "sulfonamide" as used herein refers to a radical having the structure —(R$_r$)—N—S(O)$_2$—R$_s$— or —R$_t$(R$_r$)—N—S(O)$_2$—R$_s$, where R$_t$, R$_r$, and R$_s$ can be, for example, hydrogen, alkyl, alkenyl, alkynyl, aryl, cycloalkyl, and heterocyclyl. Exemplary sulfonamides include alkylsulfonamides (e.g., where R$_s$ is alkyl), arylsulfonamides (e.g., where R$_s$ is aryl), cycloalkyl sulfonamides (e.g., where R$_s$ is cycloalkyl), and heterocyclyl sulfonamides (e.g., where R$_s$ is heterocyclyl), etc.

The term "sulfonate" as used herein refers to the radical —OSO$_3$—. Sulfonate includes salts such as —OSO$_3$Na, —OSO$_3$K, etc. and the acid —OSO$_3$H The term "sulfonic acid" refers to the radical —SO$_3$H— and its corresponding salts, e.g. —SO$_3$K—, —SO$_3$Na—.

The term "sulfonyl" as used herein refers to a radical having the structure R$_u$SO$_2$—, where R$_u$ can be alkyl, alkenyl, alkynyl, amino, amide, aryl, cycloalkyl, and heterocyclyl, e.g., alkylsulfonyl. The term "alkylsulfonyl" as used herein refers to an alkyl group attached to a sulfonyl group. "Alkylsulfonyl" groups can optionally contain alkenyl or alkynyl groups.

The term "thioketone" refers to a radical having the structure —R$_v$—C(S)—R$_w$—. The ketone can be attached to another group through R$_v$ or R$_w$. R$_v$ or R$_w$ can be alkyl, alkenyl, alkynyl, cycloalkyl, heterocyclyl or aryl, or R$_v$ or R$_w$ can be joined to form a 3- to 12-membered ring.

"Alkyl," "alkenyl," and "alkynyl" groups, collectively referred to as "saturated and unsaturated hydrocarbons," can be substituted with or interrupted by at least one group selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, thioketone, and N.

As used herein, a "suitable substituent" refers to a group that does not nullify the synthetic or pharmaceutical utility of the compounds of the invention or the intermediates useful for preparing them. Examples of suitable substituents include, but are not limited to: C$_{1-22}$, C$_{1-8}$, and C$_{1-6}$ alkyl, alkenyl or alkynyl; C$_{1-6}$ aryl, C$_{2-5}$ heteroaryl; C$_{3-7}$ cycloalkyl;

$C_{1-22}$, $C_{1-8}$, and $C_{1-6}$ alkoxy; $C_6$ aryloxy; —CN —OH; oxo; halo, carboxy; amino, such as —NH($C_{1-22}$, $C_{1-8}$, or $C_{1-6}$ alkyl), —N(($C_{1-22}$, $C_{1-8}$, and $C_{1-6}$ alkyl)$_2$, —NH(($C_6$)aryl), or —N(($C_6$)aryl)$_2$; formyl; ketones, such as —CO($C_{1-22}$, $C_{1-8}$, and $C_{1-6}$ alkyl), —CO(($C_6$aryl) esters, such as —CO$_2$($C_{1-22}$, $C_{1-8}$, and $C_{1-6}$ alkyl) and —CO$_2$ ($C_6$ aryl). One of skill in art can readily choose a suitable substituent based on the stability and pharmacological and synthetic activity of the compound of the invention.

The term "pharmaceutically acceptable carrier" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutically acceptable composition" as used herein refers to a composition comprising at least one compound as disclosed herein formulated together with one or more pharmaceutically acceptable carriers.

The term "pharmaceutically acceptable prodrugs" as used herein represents those prodrugs of the compounds of the present invention that are, within the scope of sound medical judgment, suitable for use in contact with the tissues of humans and lower animals without undue toxicity, irritation, allergic response, commensurate with a reasonable benefit/risk ratio, and effective for their intended use, as well as the zwitterionic forms, where possible, of the compounds of the invention. A discussion is provided in Higuchi et al., "Prodrugs as Novel Delivery Systems," *ACS Symposium Series*, Vol.14, and in Roche, ed. *Bioreversible Carriers in Drug Design*, American Pharmaceutical Association and Pergamon Press, 1987, both of which are incorporated herein by reference.

The term "pharmaceutically acceptable salt(s)" refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, matate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions, that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly.

Individual stereoisomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns. Stereoisomeric mixtures can also be resolved into their component stereoisomers by well known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well known asymmetric synthetic methods.

Geometric isomers can also exist in the compounds of the present invention. The present invention encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the E and Z isomers. For example, the structure below represents a genus of alkenes in which the double bond is either an "E-double bond" or a "Z-double bond."

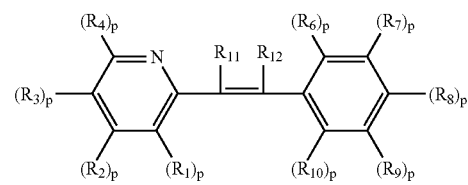

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Embodiments of the Invention

Disclosed herein are methods for increasing expression of ApoA-I in a mammal comprising administering a therapeutically effective amount of a compound of Formula I:

Formula I

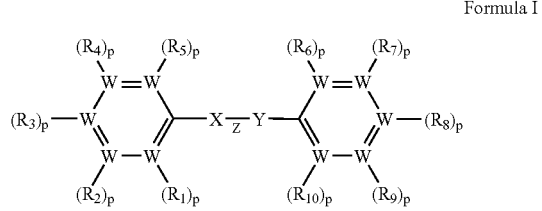

wherein:
X is selected from C, $CR_{11}$, $CR_{11}R_{13}$, CO, CS, O, S, SO, $SO_2$, N and $NR_{11}$, wherein $R_{11}$ may be the same or different than $R_{13}$;
Y is selected from C, $CR_{12}$, $CR_{12}R_{14}$, CO, CS, O, S, SO, $SO_2$, N and $NR_{12}$, wherein $R_{12}$ may be the same or different than $R_{14}$;
$R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ are each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone, or
two adjacent substituents selected from $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ are connected in a 5 or 6-membered ring to form a bicyclic aryl or bicyclic heteroaryl;
each W is independently selected from C and N, wherein if W is N, then p is 0 and if W is C, then p is 1;
Z is selected from a single bond, a double bond and a triple bond;
and pharmaceutically acceptable salts and hydrates thereof;
wherein if $R_3$ and $R_8$ are each hydroxyl, then at least one of $R_{11}$ and $R_{12}$ is not alkyl;
wherein if Z is a double bond, then $R_2$, $R_4$ and $R_8$ are not each hydroxyl; and
wherein if Formula 1 has the structure:

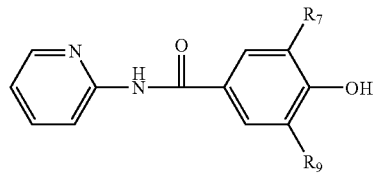

then at least one of $R_7$ and $R_9$ is not alkyl.

An alternative embodiment provides stilbene compounds of Formula 1:

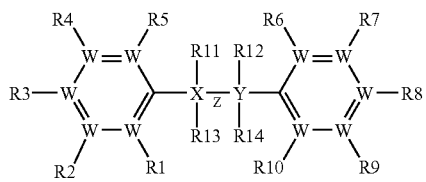

or a pharmaceutically acceptable salt thereof,
wherein
R1, R2, R3, R4, R5, R6, R7, R8, R9, R10, R11, R12, R13, and R14 are independently selected from the group consisting of $(C_1-C_{22})$alkyl, $(C_2-C_{22})$alkenyl, $(C_2-C_{22})$alkynyl, aryl, heteroaryl, alkoxy, aryloxy, benzyl, phenyl, carbonyl, thioketone, hydrogen, hydroxyl [OH], acetyl, hydroxyalkyl, aminoalkyl, amides, carbamates, halogen, bromide [Br], iodide [I], fluoride [F], chloride [Cl], $CF_3$, $CCl_3$, sulfonic acid [—$SO_3H$], phosphate, O-sulfate [the sulfate conjugate], O-glucoronidate [the glucoronic (AKA glucuronic) acid conjugates], monoesters, dicaboxylic acid, #STR55#, #STR66#, #STR77#, #STR88#, #STR99#, #STR100#,
wherein W can be C or N;
wherein when W is an nitrogen atom, the nitrogen atom will only bind to three covalent bonds due to available valence electrons.
The structures below demonstrate a nitrogen arrangement of one embodiment of the compounds of Formula 1:

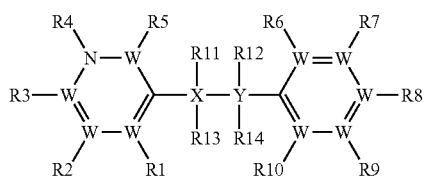

wherein the same applies to any W;
or

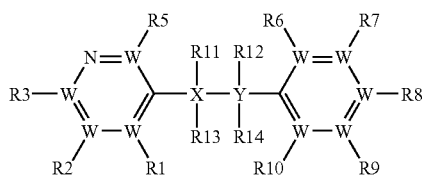

wherein the same applies to any W:
wherein
X can be CH, $CH_2$, CR11, CR13, CHR11, CHR13, CR11R13, CO, CS, O, S, SO, $SO_2$, NH, NR11 with the proviso that X and Y do not exceed the number of valence electrons available as per definitions of X and Y above
Y can be CH, $CH_2$, CR12, CR14, CHR12, CHR14, CR11R14, CO, CS, O, S, SO, $SO_2$, NH, NR11 with the proviso that X and Y do not exceed the number of valence electrons available as per definitions of X and Y above Z can be a single, double bond or triple bond, with the proviso that X and Y do not exceed the number of valence electrons available as per definitions of X and Y above;

wherein

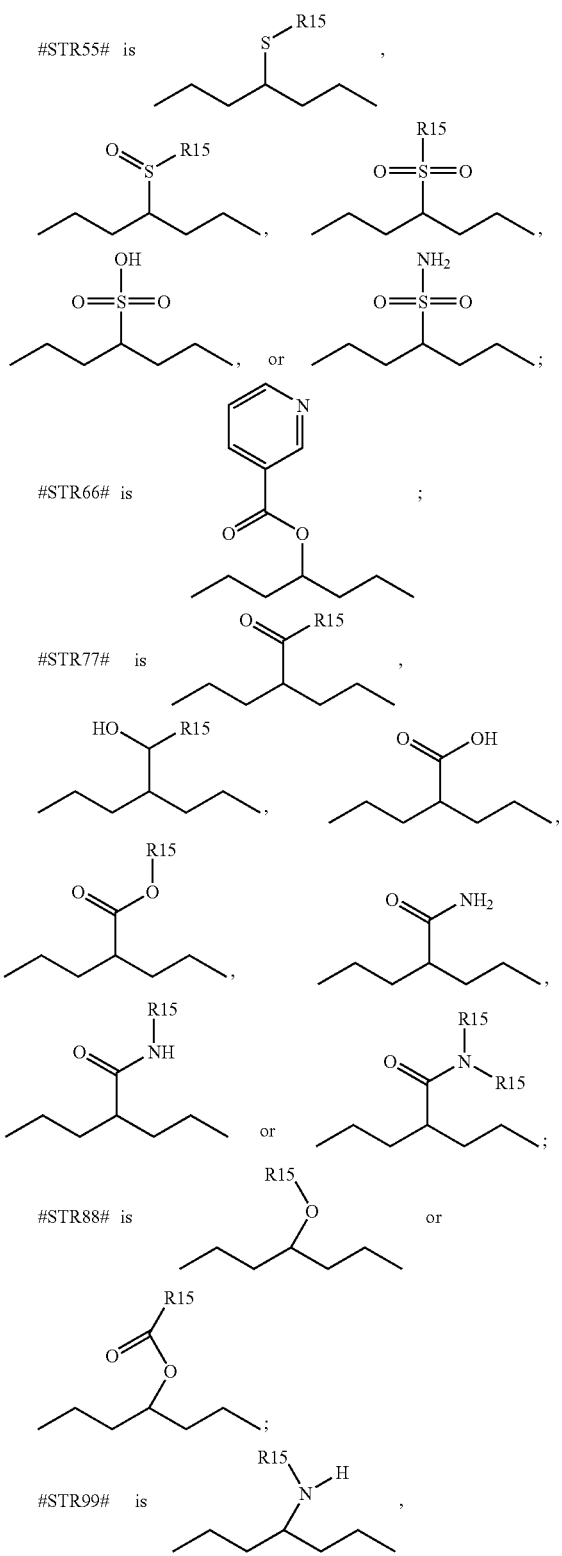

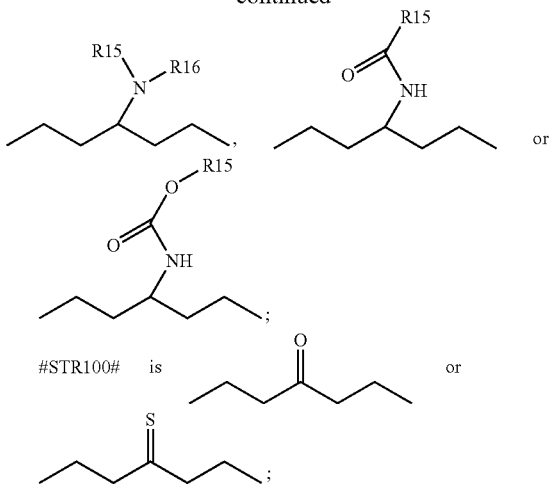

R15 and R16 are substituents independently selected from the group consisting of $(C_1$-$C_{22})$alkyl, $(C_2$-$C_{22})$alkenyl, $(C_2$-$C_{22})$alkynyl, aryl, heteroaryl, alkoxy, aryloxy, benzyl, phenyl, carbonyl, hydrogen, hydroxyl [OH], acetyl, hydroxyalkyl, aminoalkyl, amides, carbamates, halogen, bromide [Br], iodide [I], fluoride [F], chloride [Cl], $CF_3$, $CCl_3$, sulfonic acid (—$SO_3H$), phosphate, or a derivative thereof, wherein said derivative is optionally substituted and optionally branched, and may have one or more of the C atoms replaced by S, N or O;

wherein the compounds of Formula 1 have at least one proviso selected from the following R7 is a hydroxyl;

at least one W is a N;

at least one of R1-R12 is #STR77#, #STR88# or #STR99#;

R8 is #STR66#;

at least one of R1-R12 is #STR66#;

one of R1-R12 is a manoester;

one of R1-R12 is dicarboxylic acid;

one of R1-R12 is succinic acid;

that R8 and R3 are hydroxyls; and that R8 and R3 are #STR55#.

Another embodiment provides for compounds of Formula 1 wherein:

R8 is a hydroxyl and at least one W is a N;

R8 is a hydroxyl and at least one of R1-R7 and R9-R12 is #STR66#;

R8 is a hydroxyl and at least one of R1-R7 and R9-R12 is #STR77#, #STR88# or #STR99#; and R8 is #STR66# and at least one W is a N.

Non-limiting examples of compounds of Formula 1 include:

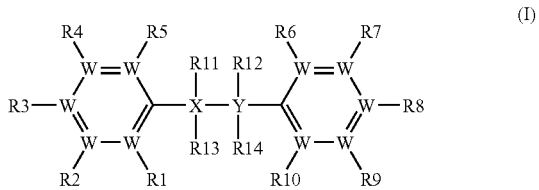

-continued
(II)
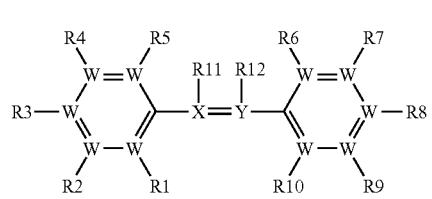
(III)
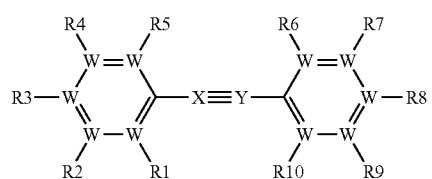
(IV)
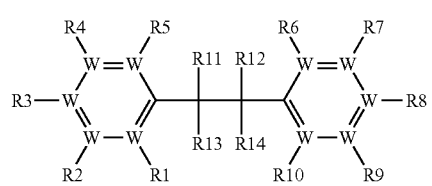
(V)
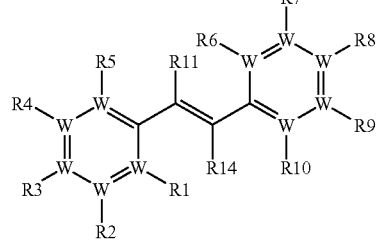
(VI)
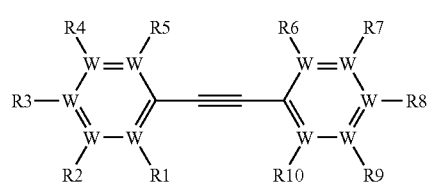
(VII)
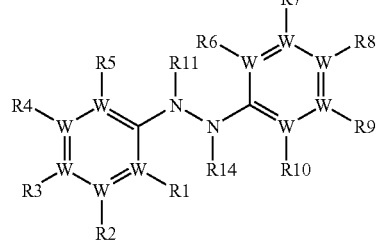
(VIII)
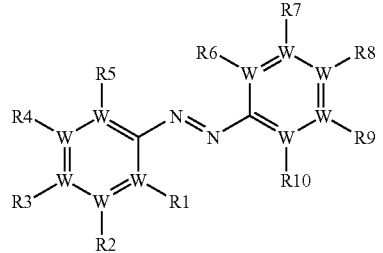
-continued
(IX)
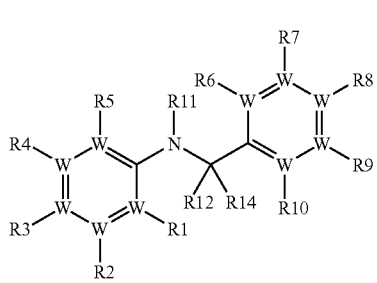
(X)
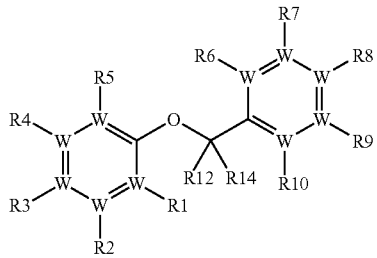
(XI)
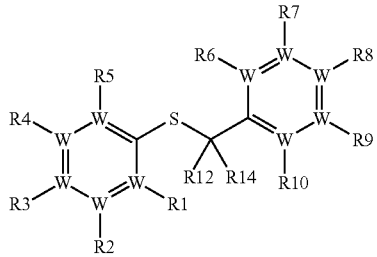
(XII)
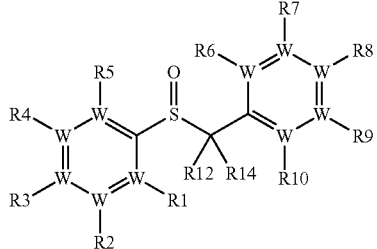
(XIII)
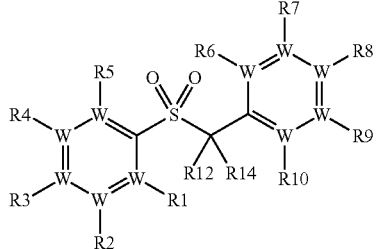
(XIV)
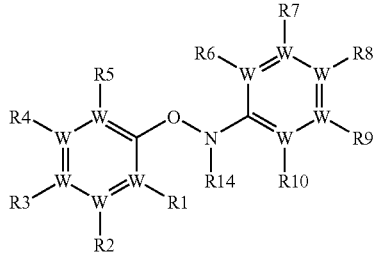

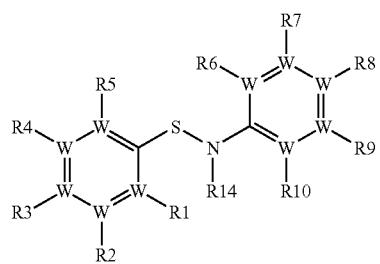 (XV)
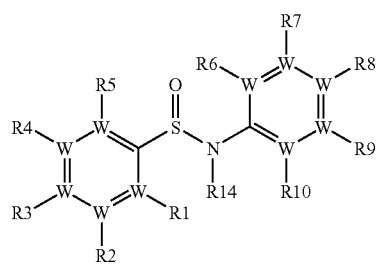 (XVI)
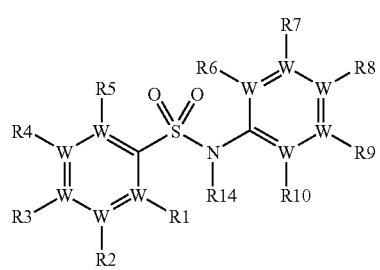 (XVII)
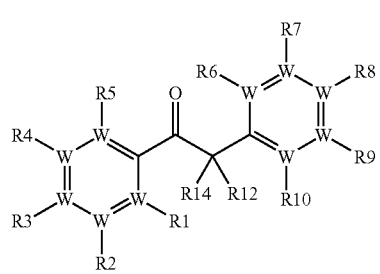 (XVIII)
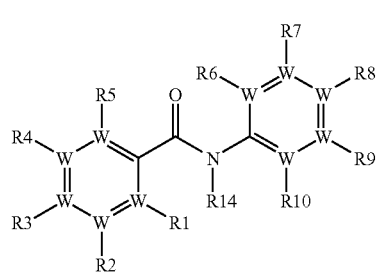 (XIX)
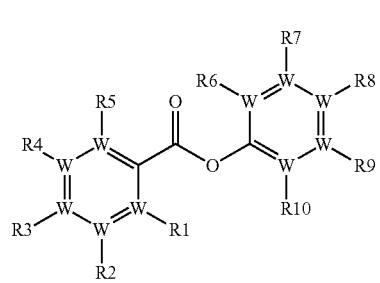 (XX)
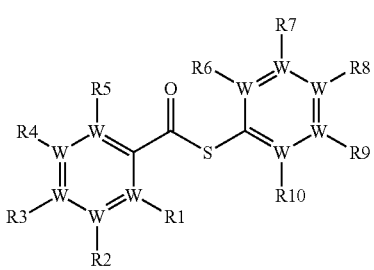 (XXI)
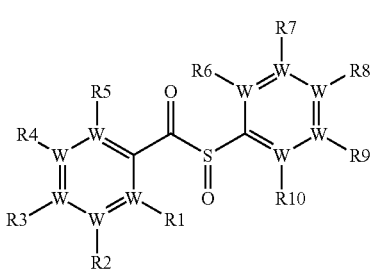 (XXII)
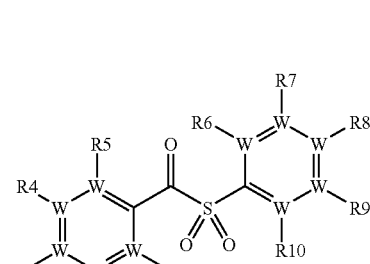 (XXIII)
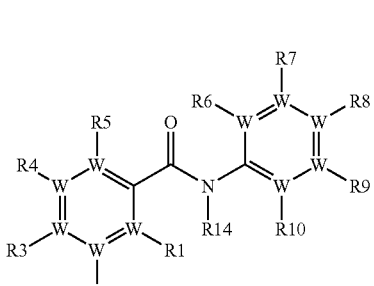 (XXIV)
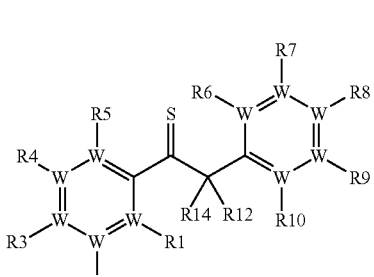 (XXV)

-continued

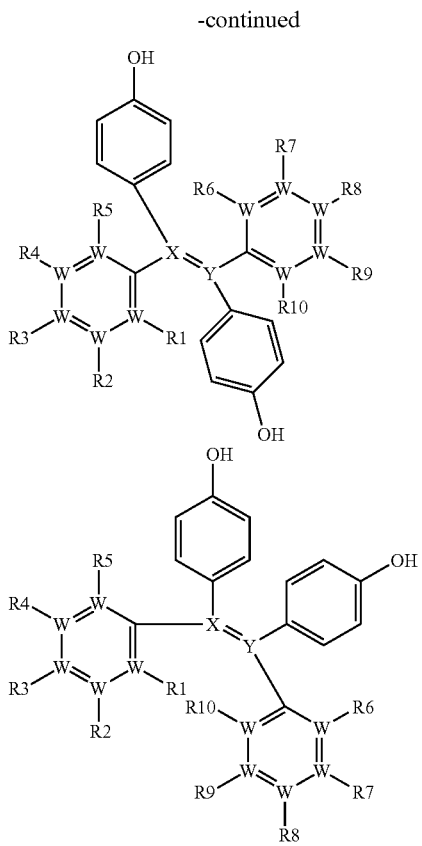

(XXVI)

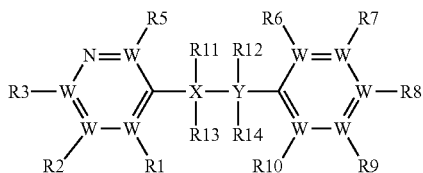

or a pharmaceutically acceptable salt thereof,
wherein
R1, R2, R3, R4, R5, R6, R7, R8, R9, R10, R11, R12, R13, and R14 are independently selected from the group consisting of ($C_1$-$C_{22}$)alkyl, ($C_2$-$C_{22}$)alkenyl, ($C_2$-$C_{22}$)alkynyl, aryl, heteroaryl, alkoxy, aryloxy, benzyl, phenyl, carbonyl, thioketone, hydrogen, hydroxyl [OH], acetyl, hydroxyalkyl, aminoalkyl, amides, carbamates, halogen, bromide [Br], iodide [I], fluoride [F], chloride [Cl], $CF_3$, $CCl_3$, sulfonic acid [—$SO_3H$], phosphate, O-sulfate [the sulfate conjugate], O-glucoronidate [the glucoronic (AKA glucuronic) acid conjugates], monoesters, dicaboxylic acid, #STR55#, #STR66#, #STR77#, #STR88#, #STR99#, #STR100#,
wherein
W can be C or N;
wherein when W is an nitrogen atom, the nitrogen atom will only bind to three covalent bonds due to available valence electrons.

The structures below demonstrate a nitrogen arrangement of one embodiment of the compounds of Formula 1:

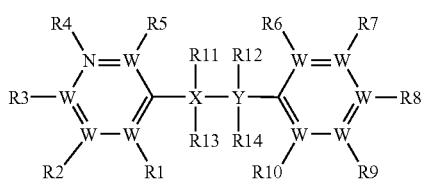

wherein the same applies to any W;

or

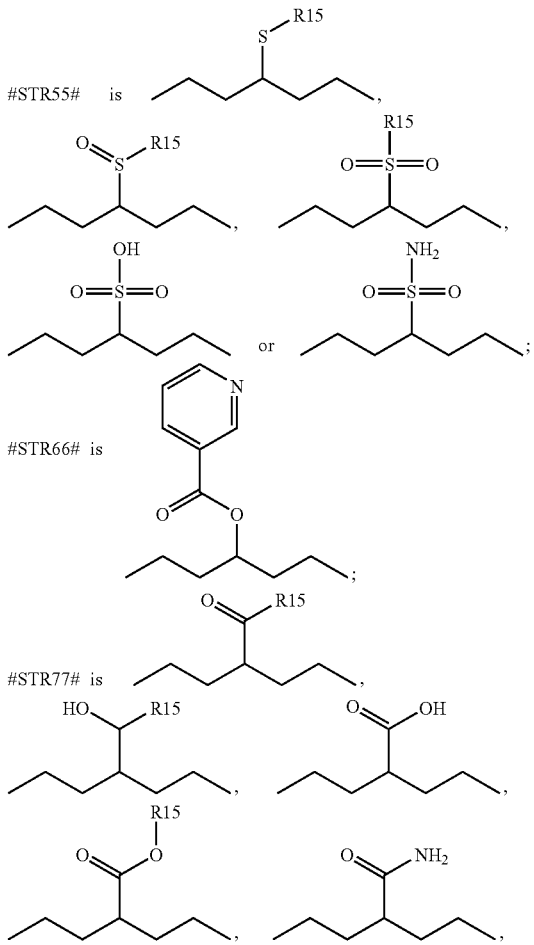

wherein the same applies to any W:
wherein
X can be CH, $CH_2$, CR11, CR13, CHR11, CHR13, CR11R13, CO, CS, O, S, SO, $SO_2$, NH, NR11 with the proviso that X and Y do not exceed the number of valence electrons available as per definitions of X and Y above Y can be CH, $CH_2$, CR12, CR14, CHR12, CHR14, CR11R14, CO, CS, O, S, SO, $SO_2$, NH, NR11 with the proviso that X and Y do not exceed the number of valence electrons available as per definitions of X and Y above Z can be a single, double bond or triple bond, with the proviso that X and Y do not exceed the number of valence electrons available as per definitions of X and Y above wherein

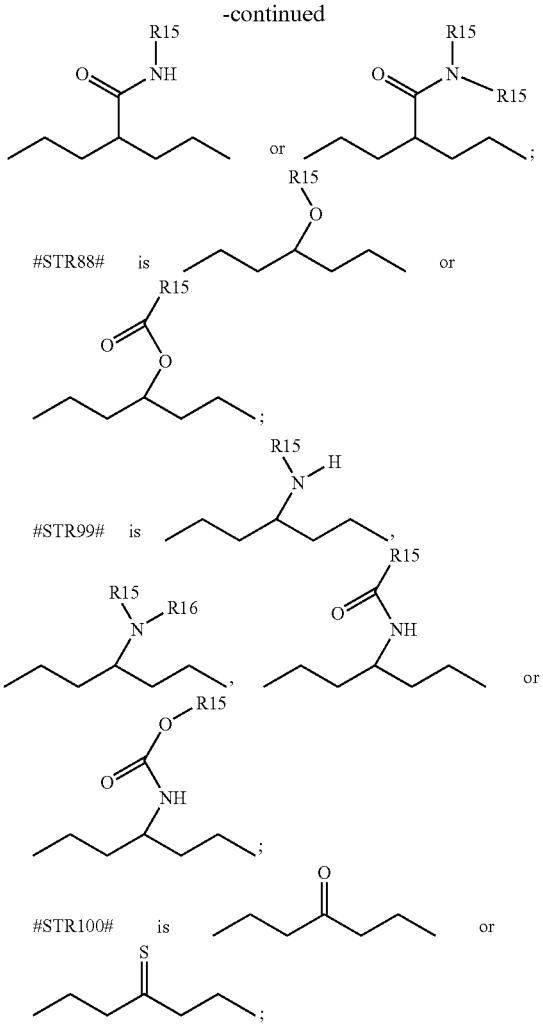

R15 and R16 are substituents independently selected from the group consisting of $(C_1-C_{22})$alkyl, $(C_2-C_{22})$alkenyl, $(C_2-C_{22})$alkynyl, aryl, heteroaryl, alkoxy, aryloxy, benzyl, phenyl, carbonyl, hydrogen, hydroxyl [OH], acetyl, hydroxyalkyl, aminoalkyl, amides, carbamates, halogen, bromide [Br], iodide [I], fluoride [F], chloride [Cl], $CF_3$, $CCl_3$, sulfonic acid ($—SO_3H$), phosphate, or a derivative thereof, wherein said derivative is optionally substituted and optionally branched, and may have one or more of the C atoms replaced by S, N or O;

wherein the compounds of Formula 1 have at least one proviso selected from the following R7 is a hydroxyl;

at least one W is a N;

at least one of R1-R12 is #STR77#, #STR88# or #STR99#;

R8 is #STR66#;

at least one of R1-R12 is #STR66#;

one of R1-R12 is a manoester;

one of R1-R12 is dicarboxylic acid;

one of R1-R12 is succinic acid;

that R8 and R3 are hydroxyls; and that R8 and R3 are #STR55#.

Another alternative embodiment provides for compounds of Formula 1 wherein:

R8 is a hydroxyl and at least one W is a N;

R8 is a hydroxyl and at least one of R1-R7 and R9-R12 is #STR66#;

R8 is a hydroxyl and at least one of R1-R7 and R9-R12 is #STR77#, #STR88# or #STR99#; and R8 is #STR66# and at least one W is a N.

Another alternative embodiment provides stilbene compounds of Formula 2:

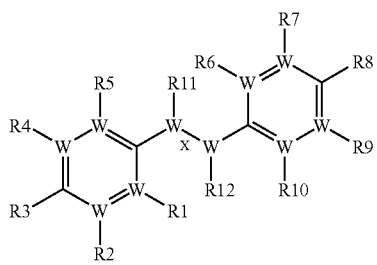

or a pharmaceutically acceptable salt thereof, wherein

R1, R2, R3, R4, R5, R6, R7, R8, R9, R10, R11 and R12 are independently selected from the group consisting of $(C_1-C_{22})$alkyl, $(C_2-C_{22})$alkenyl, aryl, heteroaryl, hydrogen, hydroxyl [OH], acetyl, hydroxyalkyl, aminoalkyl, Bromide [Br], Iodide [I], methoxy [$OCH_3$], ethoxy [$OCH_2CH_3$], fluoride [F], chloride [Cl], $CF_3$, $CCl_3$, phosphate, O-sulfate [the sulfate conjugate], O-glucoronidate [the glucoronic (AKA glucuronic) acid conjugates], #STR66#, #STR100#, #STR77#, #STR99#, #STR88#, wherein W can be C or N;

wherein when W is an nitrogen atom, the nitrogen atom will only bind to three covalent bonds due to available valence electrons.

The structures below demonstrate a nitrogen arrangement of one embodiment of the compounds of Formula 2:

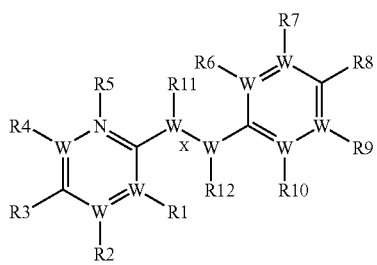

wherein the same applies to any W; or

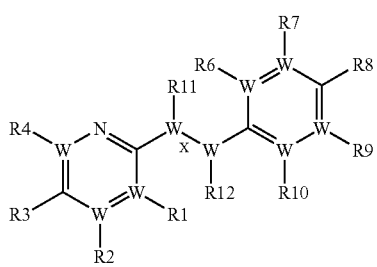

wherein the same applies to any W:
wherein

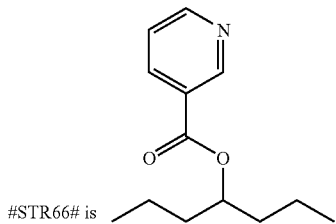

STR66# is wherein
X can be a single, double bond or triple bond, with the proviso that if a triple bond R11 and R12 are not present;
wherein

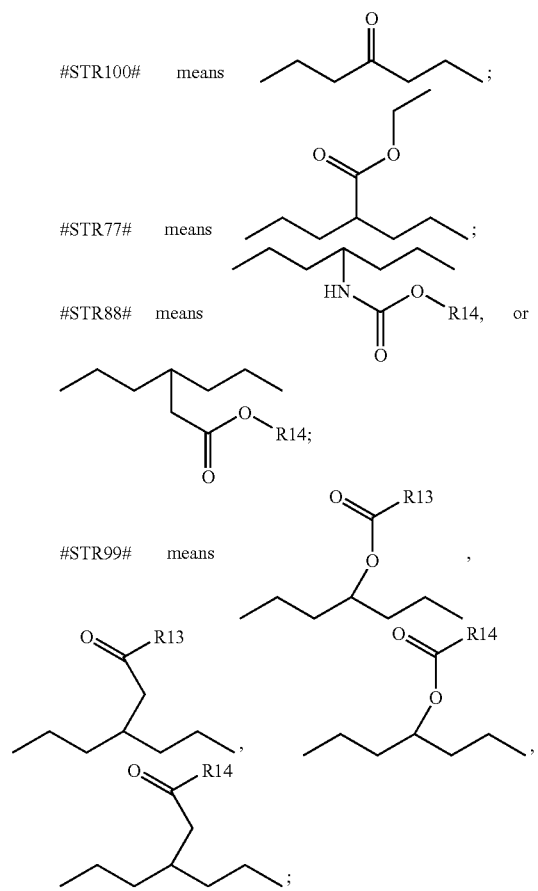

R13 is pyridine, pyridazine, pyrimidine, pyrazine; and
R14 is $(C_1-C_{22})$alkyl, $(C_2-C_{22})$alkenyl, aryl, heteroaryl or a derivative thereof, wherein said derivative is optionally substituted and optionally branched, and may have one or more of the C atoms replaced by S, N or O;
with the proviso that;
a) at least one W is a N and R8 is a hydroxyl; or
b) at least one W is a N and R8 is a hydroxyl, and optionally;
c) at least one of R1-12 is #STR77#, or #STR88#, or #STR99#, and/or;
d) at least one of R1-R12 is #STR66#.

Another alternative embodiment provides compounds comprising the general stilbene structure of Formula 2:

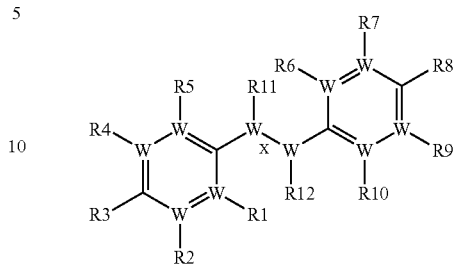

or a pharmaceutically acceptable salt thereof,
wherein
R1, R2, R3, R4, R5, R6, R7, R8, R9, R10, R11 and R12 are independently selected from the group consisting of $(C_1-C_{22})$alkyl, $(C_2-C_{22})$alkenyl, aryl, heteroaryl, hydrogen, hydroxyl [OH], acetyl, hydroxyalkyl, aminoalkyl, Bromide [Br], Iodide [I], methoxy [$OCH_3$], ethoxy [$OCH_2CH_3$], fluoride [F], chloride [Cl], $CF_3$, $CCl_3$, phosphate, O-sulfate [the sulfate conjugate], O-glucoronidate [the glucoronic (AKA glucuronic) acid conjugates], #STR66#, #STR100#, #STR77#, #STR99#, #STR88#,
wherein
W can be C or N;
wherein when W is an nitrogen atom, the nitrogen atom will only bind to three covalent bonds due to available valence electrons.

The structures below demonstrate a nitrogen arrangement of one embodiment of the compounds of Formula 2:

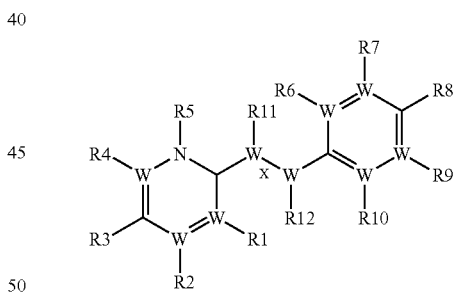

wherein the same applies to any W; or

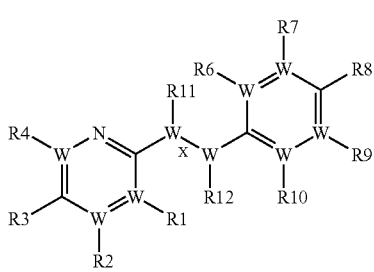

wherein the same applies to any W:
wherein

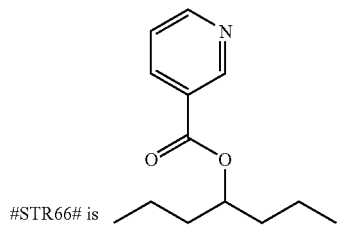

STR66# is wherein
X can be a single, double bond or triple bond, with the proviso that if a triple bond R11 and R12 are not present;
wherein

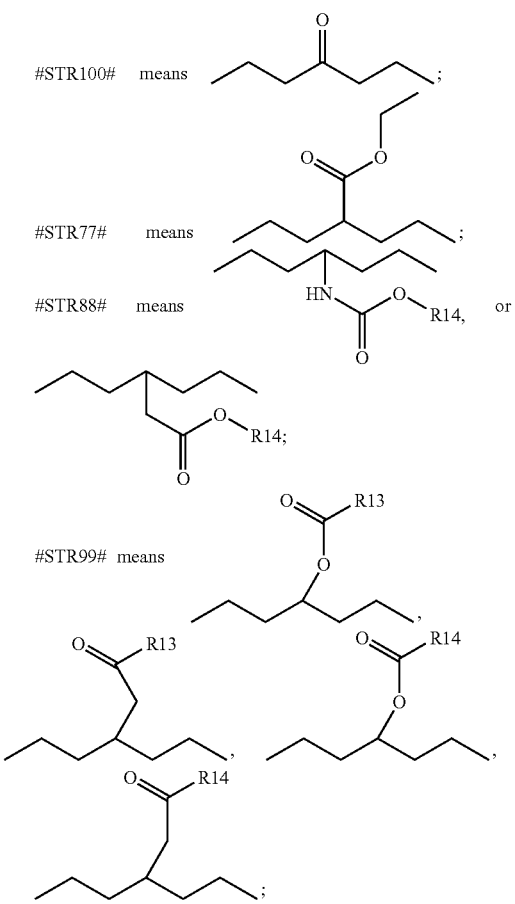

R13 is pyridine, pyridazine, pyrimidine, pyrazine; and
R14 is $(C_1-C_{22})$alkyl, $(C_2-C_{22})$alkenyl, aryl, heteroaryl or a derivative thereof, wherein said derivative is optionally substituted and optionally branched, and may have one or more of the C atoms replaced by S, N or O;
with the proviso that;
a) at least one of R1-12 is selected from #STR77# or #STR88# or #STR99#, and R8 is a hydroxyl; or
b) at least one of R1-12 is selected from #STR77# or #STR88# or #STR99#, and R8 is a hydroxyl, and optionally;
c) at least one W is a N, and/or;
d) at least one of R1-R12 is #STR66#.

Another alternative embodiment provides compounds comprising the general stilbene structure of Formula 2:

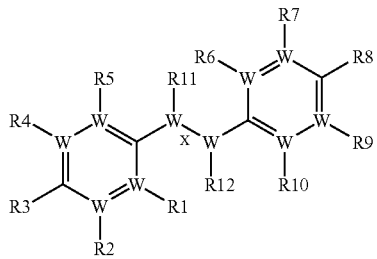

or a pharmaceutically acceptable salt thereof,
wherein
R1, R2, R3, R4, R5, R6, R7, R8, R9, R10, R11 and R12 are independently selected from the group consisting of $(C_1-C_{22})$alkyl, $(C_2-C_{22})$alkenyl, aryl, heteroaryl, hydrogen, hydroxyl [OH], acetyl, hydroxyalkyl, aminoalkyl, Bromide [Br], Iodide [I], methoxy [$OCH_3$], ethoxy [$OCH_2CH_3$], fluoride [F], chloride [Cl], $CF_3$, $CCl_3$, phosphate, O-sulfate [the sulfate conjugate], O-glucoronidate [the glucoronic (AKA glucuronic) acid conjugates], #STR66#, #STR100#, #STR77#, #STR99#, #STR88#,
wherein
W can be C or N;
wherein when W is an nitrogen atom, the nitrogen atom will only bind to three covalent bonds due to available valence electrons.

The structures below demonstrate a nitrogen arrangement of one embodiment of the compounds of Formula 2:

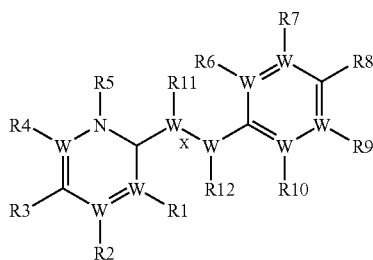

wherein the same applies to any W; or

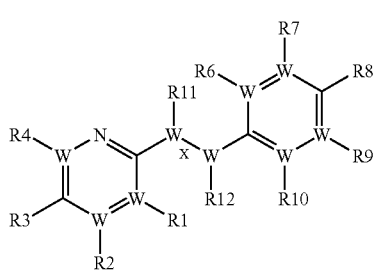

wherein the same applies to any W:
wherein

STR66# is 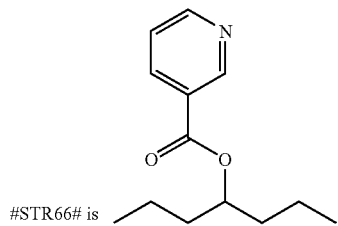

wherein
X can be a single, double bond or triple bond, with the proviso that if a triple bond R11 and R12 are not present;
wherein

STR100# means 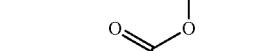;

STR77# means 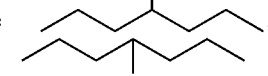;

STR88# means 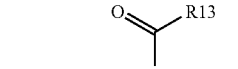 or 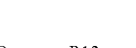;

STR99# means 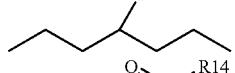, 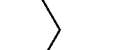, or ;

R13 is pyridine, pyridazine, pyrimidine, pyrazine; and
R14 is $(C_1-C_{22})$alkyl, $(C_2-C_{22})$alkenyl, aryl, heteroaryl or a derivative thereof, wherein said derivative is optionally substituted and optionally branched, and may have one or more of the C atoms replaced by S, N or O;
with the proviso that;
a) R8 is a hydroxyl or #STR66# and if R8 is a hydroxyl then at least one of (R1-R7 and R9-R12) is #STR66#; or
b) R8 is a hydroxyl or #STR66# and if R8 is a hydroxyl then at least one of (R1-R7 and R9-R12) is #STR66# and optionally;

c) at least one W is a N, and/or;
d) at least one of R1-12 is #STR77#, or #STR88#, or #STR99#.

Another alternative embodiment provides compounds comprising the general stilbenes structure of Formula 2:

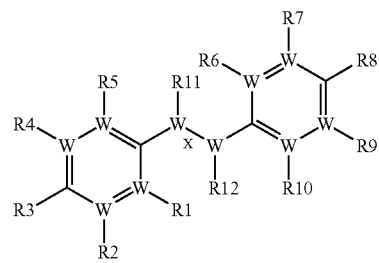

or a pharmaceutically acceptable salt thereof,
wherein
R1, R2, R3, R4, R5, R6, R7, R8, R9, R10, R11 and R12 are independently selected from the group consisting of $(C_1-C_{22})$alkyl, $(C_2-C_{22})$alkenyl, aryl, heteroaryl, hydrogen, hydroxyl [OH], acetyl, hydroxyalkyl, aminoalkyl, Bromide [Br], Iodide [I], methoxy [OCH$_3$], ethoxy [OCH$_2$CH$_3$], fluoride [F], chloride [Cl], CF$_3$, CCl$_3$, phosphate, O-sulfate [the sulfate conjugate], O-glucoronidate [the glucoronic (AKA glucuronic) acid conjugates], #STR66#, #STR100#, #STR77#, #STR99#, #STR88#,
wherein W can be C or N;
wherein when W is an nitrogen atom, the nitrogen atom will only bind to three covalent bonds due to available valence electrons.

The structures below demonstrate a nitrogen arrangement of one embodiment of the compounds of Formula 2:

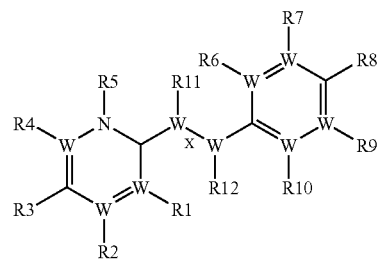

wherein the same applies to any W; or

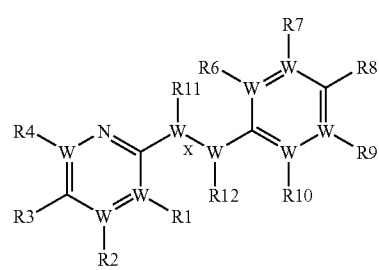

wherein the same applies to any W:
wherein

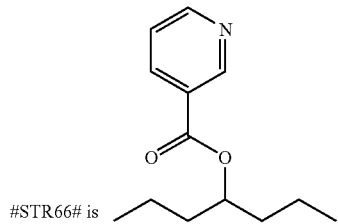

STR66# is wherein

X can be a single, double bond or triple bond, with the proviso that if a triple bond R11 and R12 are not present;
wherein

STR100# means ... ;

STR77# means ... ;

STR88# means ... , or

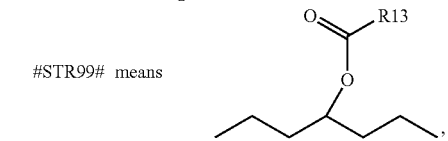

STR99# means ... , ... , or ... ;

R13 is pyridine, pyridazine, pyrimidine, pyrazine; and
R14 is $(C_1-C_{22})$alkyl, $(C_2-C_{22})$alkenyl, aryl, heteroaryl or a derivative thereof, wherein said derivative is optionally substituted and optionally branched, and may have one or more of the C atoms replaced by S, N or O;
with the proviso that:
  a) R8 is a hydroxyl or #STR66#, and
  b) at least one W is a N, and
  c) at least one of R1-12 is #STR77#, or #STR88#, or #STR99#, and
  d) at least one of R1-R12 is #STR66#.

Non-limiting examples of compounds of Formula 2 include:

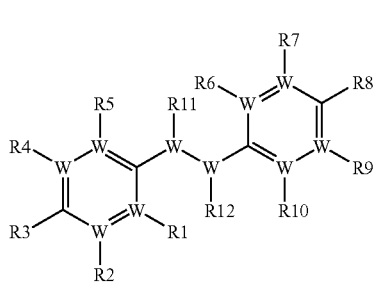
(XXVII)

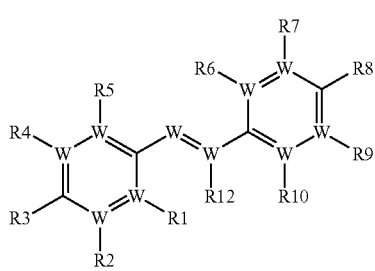
(XXVIII)

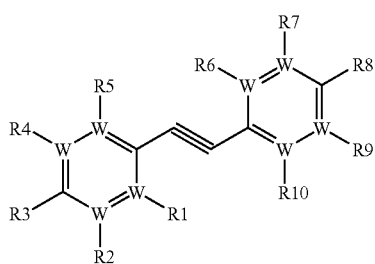
(XXIX)

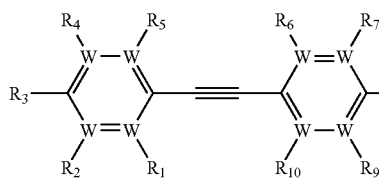
(XXX)

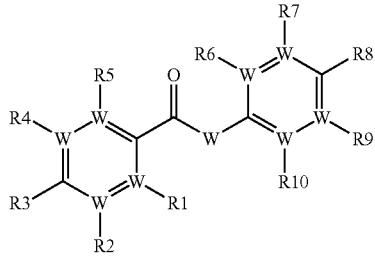
(XXXI)

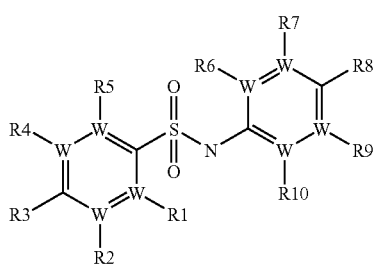
(XXXII)

or a pharmaceutically acceptable salt thereof, wherein

R1, R2, R3, R4, R5, R6, R7, R8, R9, R10, R11 and R12 are independently selected from the group consisting of ($C_1$-$C_{22}$)alkyl, ($C_2$-$C_{22}$)alkenyl, aryl, heteroaryl, hydrogen, hydroxyl [OH], acetyl, hydroxyalkyl, aminoalkyl, Bromide [Br], Iodide [I], methoxy [$OCH_3$], ethoxy [$OCH_2CH_3$], fluoride [F], chloride [Cl], $CF_3$, $CCl_3$, phosphate, O-sulfate [the sulfate conjugate], O-glucoronidate [the glucoronic (AKA glucuronic) acid conjugates], #STR66#, #STR100#, #STR77#, #STR99#, #STR88#, wherein W can be C or N;

wherein when W is an nitrogen atom, the nitrogen atom will only bind to three covalent bonds due to available valence electrons.

The structures below demonstrate a nitrogen arrangement of one embodiment of the compounds of Formula 2:

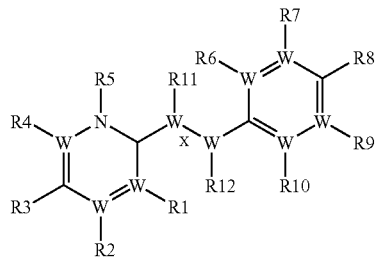

wherein the same applies to any W; or

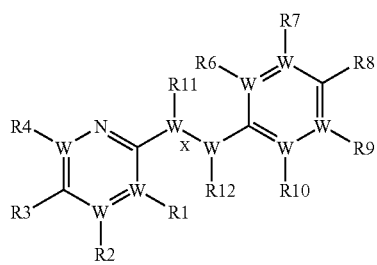

wherein the same applies to any W:

wherein

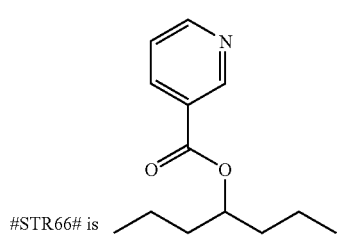

STR66# is wherein

X can be a single, double bond or triple bond, with the proviso that if a triple bond R11 and R12 are not present;

wherein

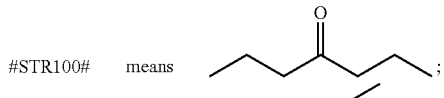

STR100# means

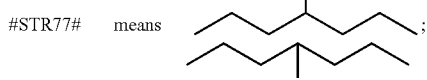

STR77# means

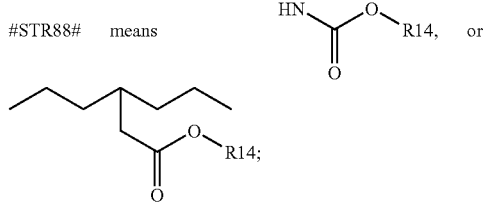

STR88# means

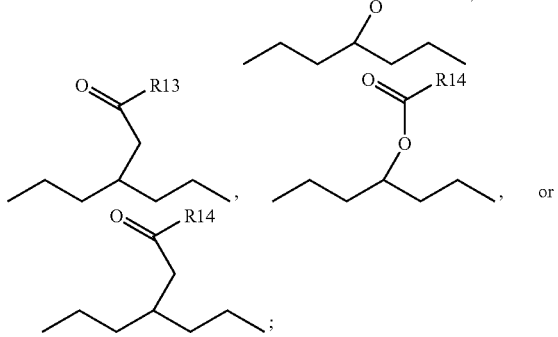

STR99# means

R13 is pyridine, pyridazine, pyrimidine, pyrazine; and

R14 is ($C_1$-$C_{22}$)alkyl, ($C_2$-$C_{22}$)alkenyl, aryl, heteroaryl or a derivative thereof, wherein said derivative is optionally substituted and optionally branched, and may have one or more of the C atoms replaced by S, N or O;

wherein the compounds of Formula 2 have one of the following groups of provisos:

1) with the proviso that:
a) R8 is a hydroxyl; or
b) R8 is a hydroxyl, and optionally;
c) at least one W is a N, and/or;
d) at least one of R1-12 is #STR77#, or #STR88#, or #STR99#, and/or;
e) at least one of R1-R12 is #STR66#.

2) with the proviso that;
a) at least one W is a N and R8 is a hydroxyl; or
b) at least one W is a N and R8 is a hydroxyl, and optionally;
c) at least one of R1-12 is #STR77#, or #STR88#, or #STR99#, and/or;
d) at least one of R1-R12 is #STR66#.

3) with the proviso that:
a) at least one of R1-12 is selected from #STR77# or #STR88# or #STR99#, and R8 is a hydroxyl; or
b) at least one of R1-12 is selected from #STR77# or #STR88# or #STR99#, and R8 is a hydroxyl, and optionally;
c) at least one W is a N, and/or;
d) at least one of R1-R12 is #STR66#.

4) with the proviso that:
a) R8 is a hydroxyl or #STR66# and if R8 is a hydroxyl at least one of (R1-R7 and R8-R12) is #STR66#; or
b) R8 is a hydroxyl or #STR66# and if R8 is a hydroxyl at least one of (R1-R7 and R9-R12) is #STR66# and optionally;
c) at least one W is a N, and/or;
d) at least one of R1-12 is #STR77#, or #STR88#, or #STR99#.
5) with the proviso that;
a) R8 is a hydroxyl or #STR66#, and
b) at least one W is a N, and
c) at least one of R1-12 is #STR77#, or #STR88#, or #STR99#, and
d) at least one of R1-R12 is #STR66#.

Another alternative embodiment provides stilbene compounds of Formula 3:

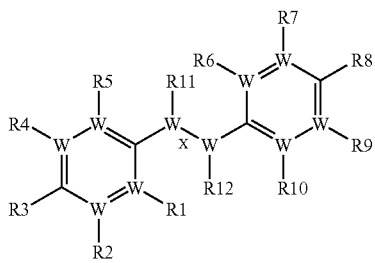

and a pharmaceutically acceptable salt thereof,
wherein
R1, R2, R3, R4, R5, R6, R7, R8, R9, R10, R11 and R12 are independently selected from the group consisting of $(C_1-C_{22})$alkyl, $(C_2-C_{22})$alkenyl, aryl, heteroaryl, hydrogen, hydroxyl [OH], acetyl, hydroxyalkyl, aminoalkyl, Bromide [Br], Iodide [I], methoxy [OCH$_3$], ethoxy [OCH$_2$CH$_3$], fluoride [F], chloride [Cl], CF$_3$, CCl$_3$, phosphate, O-sulfate [the sulfate conjugate], O-glucoronidate [the glucoronic (AKA glucuronic) acid conjugates],
wherein

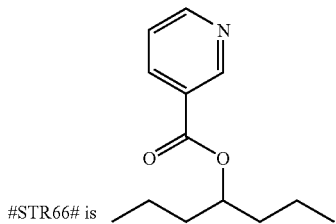

STR66# is wherein
X can be a single, double bond or triple bond, with the proviso that if a triple bond R11 and R12 are not present;
W can be C or N;
with the proviso that
a) R3 and R8 are hydroxyls and at least one W is a N and optionally:
b) at least one of R1-R12 is #STR66#; and/or
c) R8 is #STR66#

Another alternative embodiment provides compounds comprising of the general stilbenes structure of Formula 3:

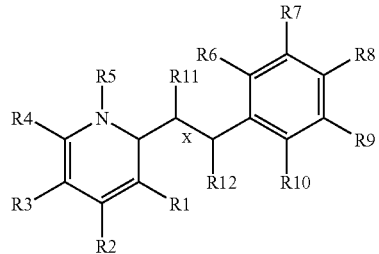

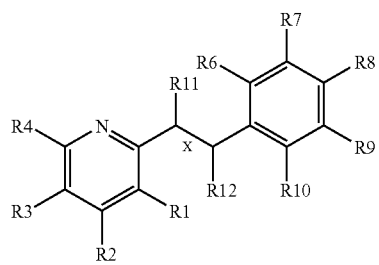

and a pharmaceutically acceptable salt thereof,
wherein
R1, R2, R3, R4, R5, R6, R7, R8, R9, R10, R11 and R12 are independently selected from the group consisting of $(C_1-C_{22})$alkyl, $(C_2-C_{22})$alkenyl, aryl, heteroaryl, hydrogen, hydroxyl [OH], acetyl, hydroxyalkyl, aminoalkyl, Bromide [Br], Iodide [I], methoxy [OCH$_3$], ethoxy [OCH$_2$CH$_3$], fluoride [F], chloride [Cl], CF$_3$, CCl$_3$, phosphate, O-sulfate [the sulfate conjugate], O-glucoronidate [the glucoronic (AKA glucuronic) acid conjugates],
wherein

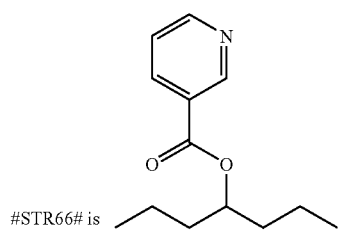

STR66# is wherein
X can be a single, double bond or triple bond, with the proviso that if a triple bond R11 and R12 are not present;
with the proviso that
a) R3 and R8 are hydroxyls, and optionally:
b) at least one of R1-R12 is #STR66#; and/or
c) R8 is #STR66#.

Non-limiting examples of stilbene compounds of Formula 3 include:

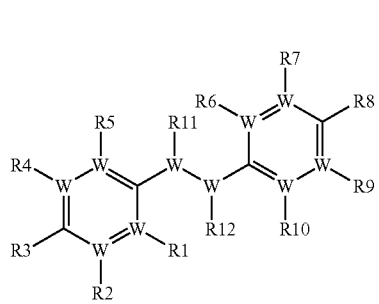
(XXXIII)

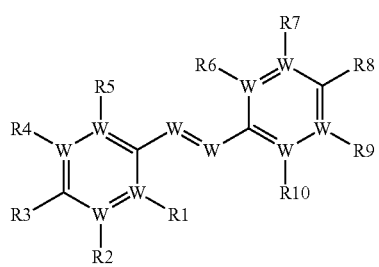
(XXXIV)

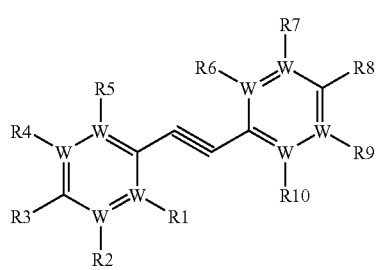
(XXXV)

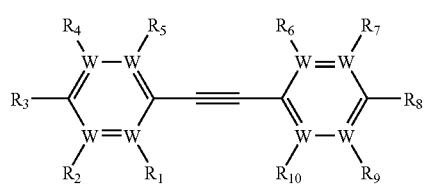
(XXXVI)

and a pharmaceutically acceptable salt thereof,
wherein

R1, R2, R3, R4, R5, R6, R7, R8, R9, R10, R11 and R12 are independently selected from the group consisting of $(C_1-C_{22})$alkyl, $(C_2-C_{22})$alkenyl, aryl, heteroaryl, hydrogen, hydroxyl [OH], acetyl, hydroxyalkyl, aminoalkyl, Bromide [Br], Iodide [I], methoxy [OCH$_3$], ethoxy [OCH$_2$CH$_3$], fluoride [F], chloride [Cl], CF$_3$, CCl$_3$, phosphate, O-sulfate [the sulfate conjugate], O-glucoronidate [the glucoronic (AKA glucuronic) acid conjugates], wherein

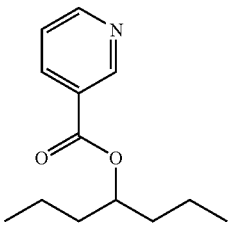
STR66# means wherein

X can be a single, double bond or triple bond, with the proviso that if a triple, bond R11 and R12 are not present;

W can be C or N;

with the proviso that a) R3 and R8 are hydroxyls and at least one W is a N and optionally:

b) at least one of R1-R12 is #STR66#; and/or c) R8 is #STR66#

Another alternative embodiment provides compounds comprising of the general stilbene structure of Formula 3:

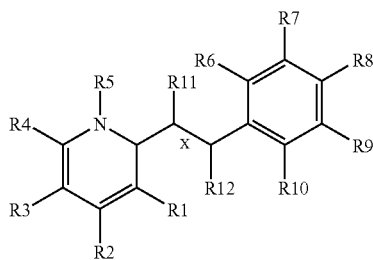

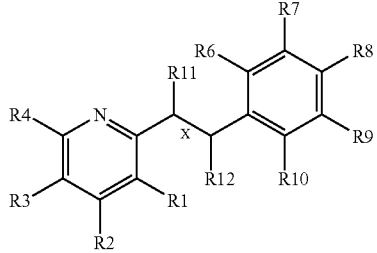

which can be further subdivided into the following structures:

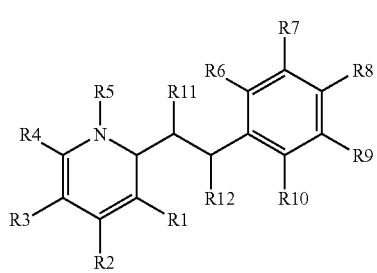
(XXXVII)

-continued (XXXVIII)
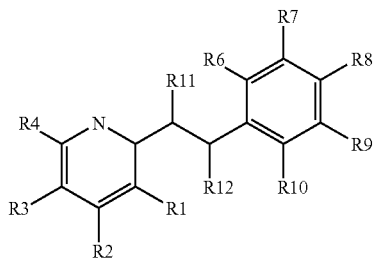

(XXXIX)
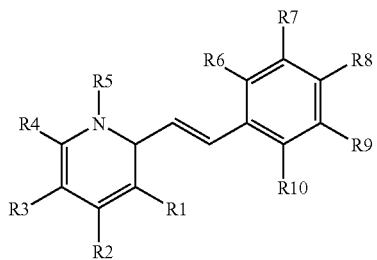

(XL)
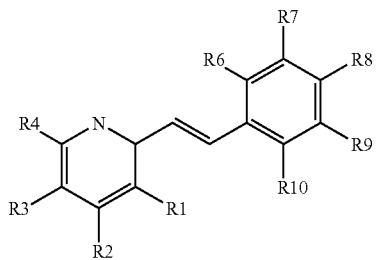

(XLI)
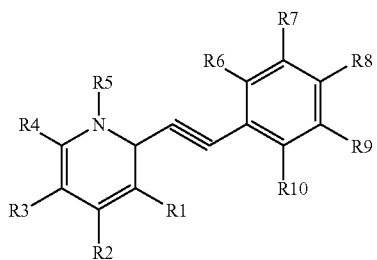

(XLII)

(XLIII)
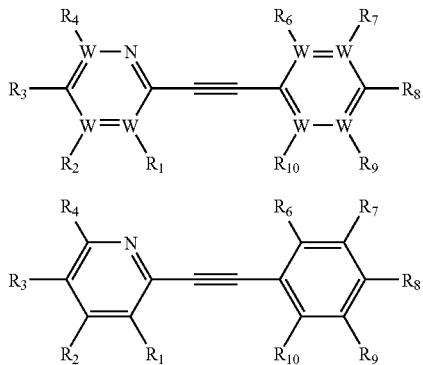

and a pharmaceutically acceptable salt thereof, wherein

R1, R2, R3, R4, R5, R6, R7, R8, R9, R10, R11 and R12 are independently selected from the group consisting of $(C_1-C_{22})$alkyl, $(C_2-C_{22})$alkenyl, aryl, heteroaryl, hydrogen, hydroxyl [OH], acetyl, hydroxyalkyl, aminoalkyl, Bromide [Br], Iodide [I], methoxy [OCH$_3$], ethoxy [OCH$_2$CH$_3$], fluoride [F], chloride [Cl], CF$_3$, CCl$_3$, phosphate, O-sulfate [the sulfate conjugate], O-glucoronidate [the glucoronic (AKA glucuronic) acid conjugates], wherein

STR66# means 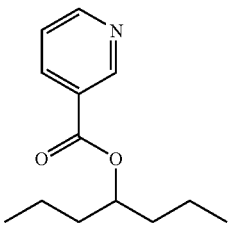

wherein

X can be a single, double bond or triple bond, with the proviso that if a triple bond R11 and R12 are not present;

with the proviso that a) R3 and R8 are hydroxyls, and optionally:
b) at least one of R1-R12 is #STR66#; and/or
c) R8 is #STR66#.

Disclosed herein are methods for increasing expression of ApoA-I in a mammal comprising administering a therapeutically effective amount of a compound of Formula IV:

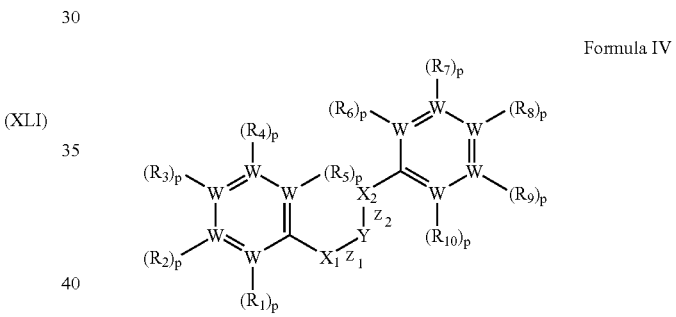

Formula IV wherein:

$X_1$ is selected from C, $CR_{11}$, $CR_{11}R_{13}$, CO, CS, O, S, SO, SO$_2$, N and $NR_{11}$, wherein $R_{11}$ may be the same or different than $R_{13}$;

$X_2$ is selected from C, $CR_{17}$, $CR_{17}R_{18}$, CO, CS, O, S, SO, SO$_2$, N and $NR_{17}$, wherein $R_{17}$ may be the same or different than $R_{18}$;

Y is selected from C, $CR_{12}$, $CR_{12}R_{14}$, CO, CS, S, SO, SO$_2$, N and $NR_{12}$, wherein $R_{12}$ may be the same or different than $R_{14}$;

$R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{17}$ and $R_{18}$ are each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone, or two adjacent substituents selected from $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{17}$ and $R_{18}$ are connected in a 5 or 6-membered ring to form a bicyclic aryl or bicyclic heteroaryl;

each W is independently selected from C and N, wherein if W is N, then p is 0 and if W is C, then p is 1;

$Z_1$ and $Z_2$ are each independently selected from a single bond, a double bond, and a triple bond;

and pharmaceutically acceptable salts and hydrates thereof.

An alternative embodiment provides chalcone compounds of Formula 4:

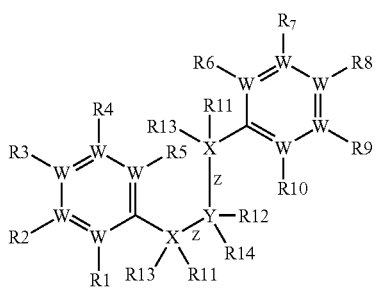

or a pharmaceutically acceptable salt thereof, wherein

R1, R2, R3, R4, R5, R6, R7, R8, R9, R10, R11, R12, R13, and R14 are independently selected from the group consisting of $(C_1$-$C_{22})$alkyl, $(C_2$-$C_{22})$alkenyl, $(C_1$-$C_{22})$alkynyl, aryl, heteroaryl, alkoxy, aryloxy, benzyl, phenyl, carbonyl, thioketone, hydrogen, hydroxyl [OH], acetyl, hydroxyalkyl, aminoalkyl, amides, carbamates, halogen, bromide [Br], iodide [I], fluoride [F], chloride [Cl], $CF_3$, $CCl_3$, sulfonic acid [-$SO_3H$], phosphate, O-sulfate [the sulfate conjugate], O-glucoronidate [the glucoronic (AKA glucuronic) acid conjugates], monoesters, dicaboxylic acid, #STR55#, #STR66#, #STR77#, #STR88#, #STR99#, #STR100#, wherein W can be C or N;

wherein when W is an nitrogen atom, the nitrogen atom will only bind to three covalent bonds due to available valence electrons.

The structures below demonstrate a nitrogen arrangement of one embodiment of the compounds of Formula 4:

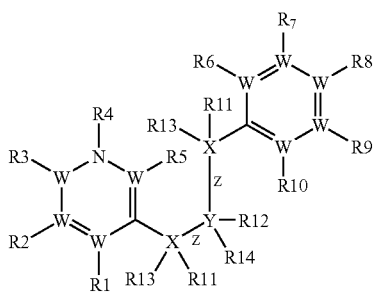

wherein the same applies to any W;

or

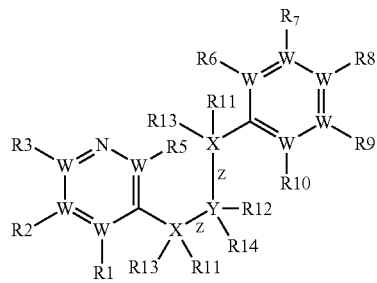

wherein the same applies to any W:

wherein

X can be CH, $CH_2$, CR11, CR13, CHR11, CHR13, CR11 R13, CO, CS, O, S, SO, $SO_2$, NH, NR11 with the proviso that X and Y do not exceed the number of valence electrons available as per definitions of X and Y above Y can be CH, $CH_2$, CR12, CR14, CHR12, CHR14, CR11 R14, CO, CS, O, S, SO, $SO_2$, NH, NR11 with the proviso that X and Y do not exceed the number of valence electrons available as per definitions of X and Y above Z can be a single, double bond or triple bond, with the proviso that X and Y do not exceed the number of valence electrons available as per definitions of X and Y above wherein

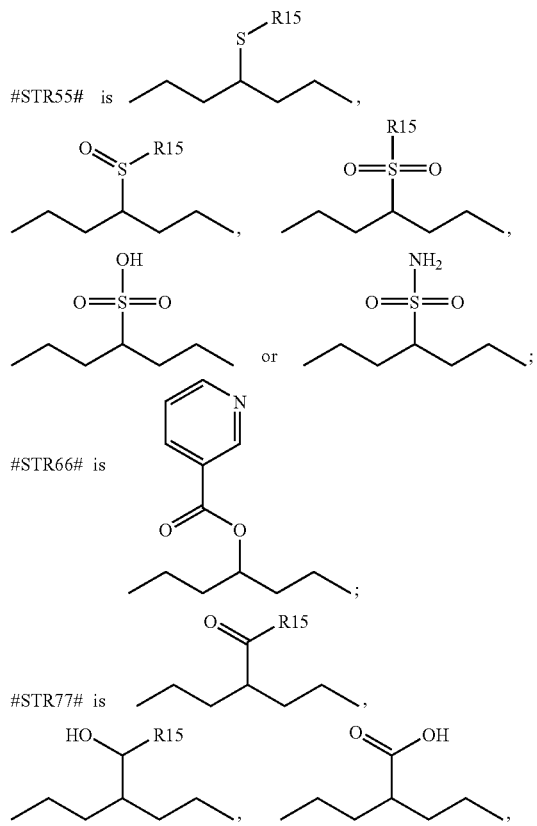

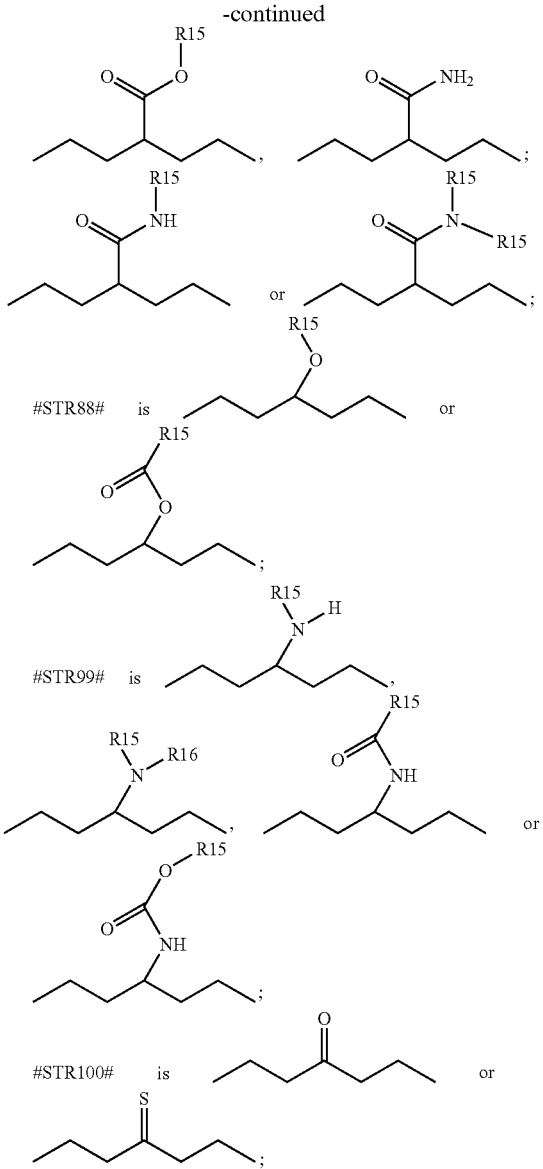

R15 and R16 are substituents independently selected from the group consisting of $(C_1-C_{22})$alkyl, $(C_2-C_{22})$alkenyl, $(C_2-C_{22})$alkynyl, aryl, heteroaryl, alkoxy, aryloxy, benzyl, phenyl, carbonyl, hydrogen, hydroxyl [OH], acetyl, hydroxyalkyl, aminoalkyl, amides, carbamates, halogen, bromide [Br], iodide [I], fluoride [F], chloride [Cl], $CF_3$, $CCl_3$, sulfonic acid [—$SO_3H$], phosphate, or a derivative thereof, wherein said derivative is optionally substituted and optionally branched, and may have one or more of the C atoms replaced by S, N or O;

wherein Formula 4 compounds have at least one proviso selected from the following:
R7 is a hydroxyl;
at least one W is a N;
at least one of R1-R10 is #STR77#, #STR88# or #STR99#;
at least one of R1-R10 is #STR66#;
R7 is #STR66#;
one of R1-R10 is a monoester;
one of R1-R10 is succinic acid;
R7 is #STR55#;
R7 and R2 are #STR55#;
R7 and R2 are hydroxyls; and
one of R1-R10 is a dicarboxylic acid.

Another alternative embodiment provides for compounds of Formula IV wherein:
R7 is a hydroxyl and at least one W is a N;
R7 is a hydroxyl and at least one of R1-R6 and R8-R10 is #STR66#;
R7 is a hydroxyl and at least one of R1-R6 and R8-R10 is #STR77 #, #STR88# or #STR99#; and
R7 is #STR66# and at least one W is a N.

Non-limiting examples of compounds of Formula 4 include the E and Z isomers of the following structures:

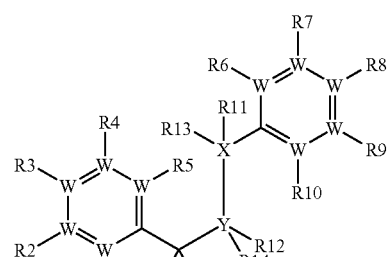
(XLIV)

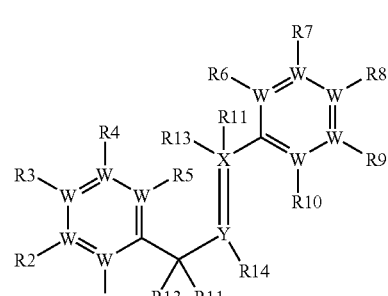
(XLV)

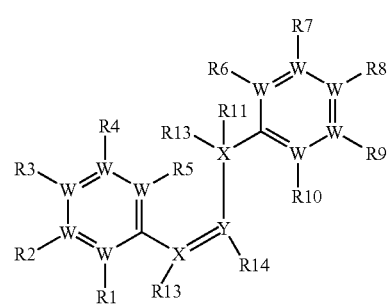
(XLVI)

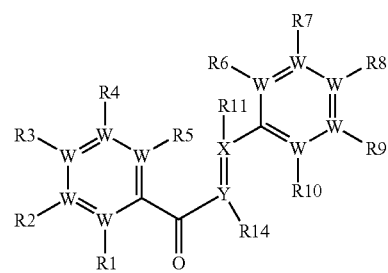
(XLVII)

-continued

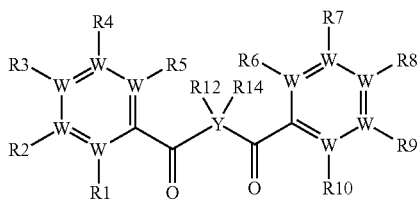
(XLVIII)

or a pharmaceutically acceptable salt thereof,
wherein
R1, R2, R3, R4, R5, R6, R7, R8, R9, R10, R11, R12, R13, and R14 are independently selected from the group consisting of $(C_1-C_{22})$alkyl, $(C_2-C_{22})$alkenyl, $(C_1-C_{22})$alkynyl, aryl, heteroaryl, alkoxy, aryloxy, benzyl, phenyl, carbonyl, thioketone, hydrogen, hydroxyl [OH], acetyl, hydroxyalkyl, aminoalkyl, amides, carbamates, halogen, bromide [Br], iodide [I], fluoride [F], chloride [Cl], $CF_3$, $CCl_3$, sulfonic acid [—$SO_3H$], phosphate, O-sulfate [the sulfate conjugate], O-glucoronidate [the glucoronic (AKA glucuronic) acid conjugates], monoesters, dicaboxylic acid, #STR55#, #STR66#, #STR77#, #STR88#, #STR99#, #STR100#,
wherein
W can be C or N;
wherein when W is an nitrogen atom, the nitrogen atom will only bind to three covalent bonds due to available valence electrons. The structures below demonstrate a nitrogen arrangement of one embodiment of the compounds of Formula 4:

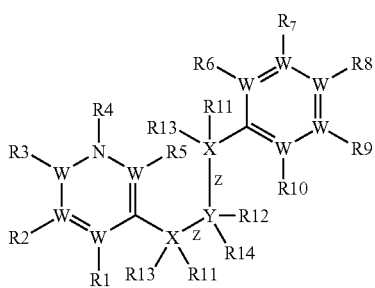

wherein the same applies to any W;
or

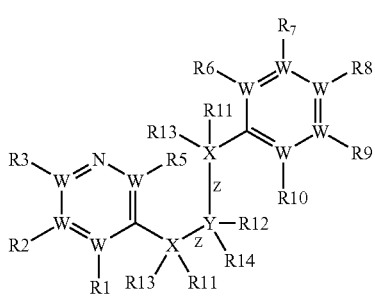

wherein the same applies to any W:
wherein
X can be CH, $CH_2$, CR11, CR13, CHR11, CHR13, CR11 R13, CO, CS, O, S, SO, $SO_2$, NH, NR11 with the proviso that X and Y do not exceed the number of valence electrons available as per definitions of X and Y above Y can be CH, $CH_2$, CR12, CR14, CHR12, CHR14, CR11 R14, CO, CS, O, S, SO, $SO_2$, NH, NR11 with the proviso that X and Y do not exceed the number of valence electrons available as per definitions of X and Y above Z can be a single, double bond or triple bond, with the proviso that X and Y do not exceed the number of valence electrons available as per definitions of X and Y above wherein

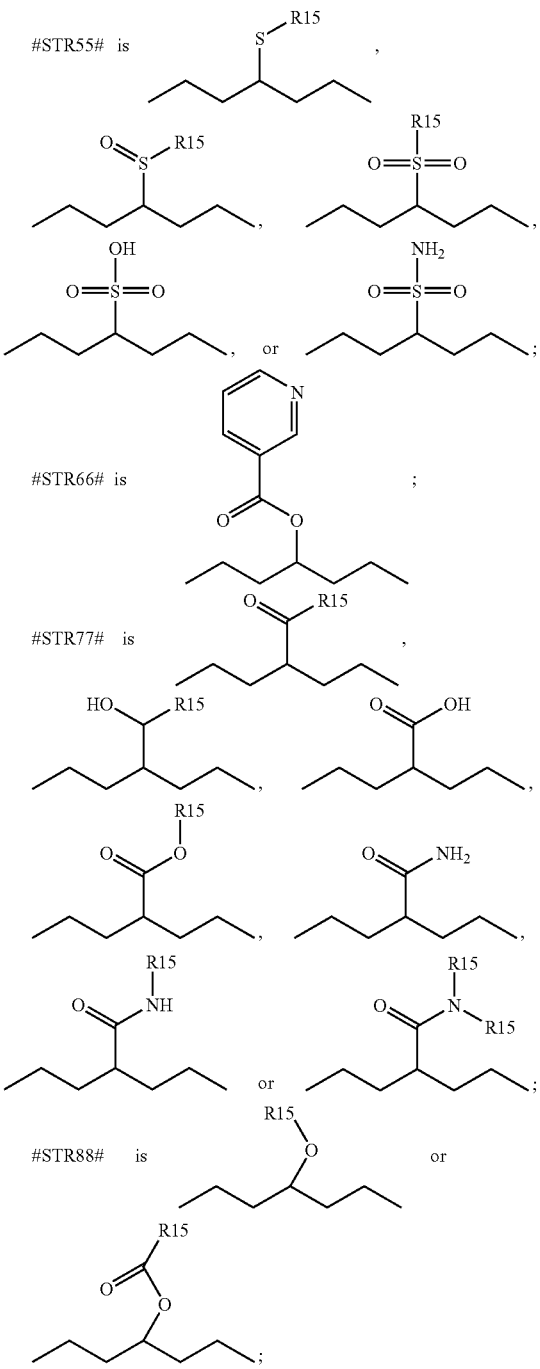

-continued

STR99# is

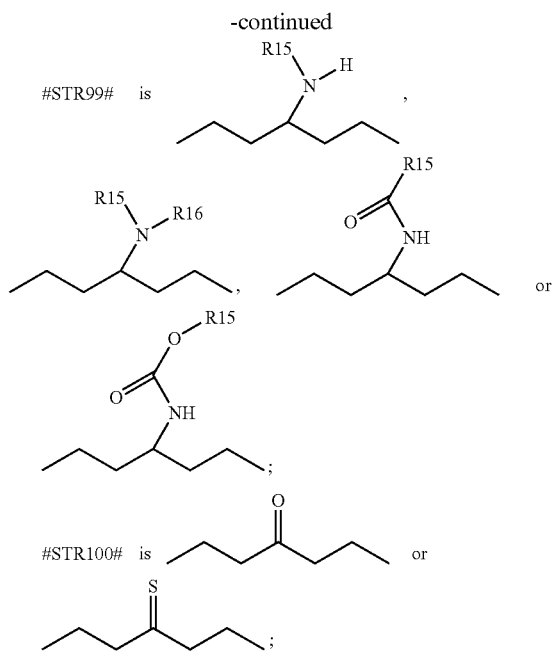

STR100# is

R15 and R16 are substituents independently selected from the group consisting of $(C_1-C_{22})$alkyl, $(C_2-C_{22})$alkenyl, $(C_2-C_{22})$alkynyl, aryl, heteroaryl, alkoxy, aryloxy, benzyl, phenyl, carbonyl, hydrogen, hydroxyl [OH], acetyl, hydroxyalkyl, aminoalkyl, amides, carbamates, halogen, bromide [Br], iodide [I], fluoride [F], chloride [Cl], $CF_3$, $CCl_3$, sulfonic acid [—$SO_3H$], phosphate, or a derivative thereof, wherein said derivative is optionally substituted and optionally branched, and may have one or more of the C atoms replaced by S, N or O;

wherein Formula 4 compounds have at least one proviso selected from the following:

R7 is a hydroxyl;
at least one W is a N;.
at least one of R1-R10 is #STR77#, #STR88# or #STR99#;
at least one of R1-R10 is #STR66#;
R7 is #STR66#;
one of R1-R10 is a monoester;
one of R1-R10 is succinic acid;
R7 is #STR55#;
R7 and R2 are #STR55#;
R7 and R2 are hydroxyls; and
one of R1-R10 is a dicarboxylic acid.

Another alternative embodiment provides for compounds of Formula 4 wherein:

R7 is a hydroxyl and at least one W is a N;
R7 is a hydroxyl and at least one of R1-R6 and R8-R10 is #STR66#;
R7 is a hydroxyl and at least one of R1-R6 and R8-R10 is #STR77#, #STR88# or #STR99#; and
R7 is #STR66# and at least one W is a N.

Another alternative embodiment provides chalcone compounds of Formula 5:

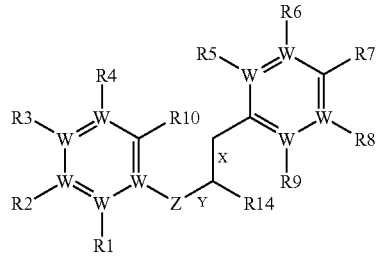

or a pharmaceutically acceptable salt thereof,
wherein

R1, R2, R3, R4, R5, R6, R8, R9, and R10 are independently selected from the group consisting of $(C_1-C_{22})$alkyl, $(C_2-C_{22})$alkenyl, aryl, heteroaryl, hydrogen, hydroxyl [OH], acetyl, hydroxyalkyl, aminoalkyl, Bromide [Br], Iodide [I], methoxy [$OCH_3$], ethoxy [$OCH_2CH_3$], fluoride [F], chloride [Cl], $CF_3$, $CCl_3$, phosphate, O-sulfate [the sulfate conjugate], O-glucoronidate [the glucoronic (AKA glucuronic) acid conjugates], #STR66#, #STR77#, #STR88#, #STR99#, #STR100# wherein W can be C or N;

wherein when W is an nitrogen atom, the nitrogen atom will only bind to three covalent bonds due to available valence electrons.

The structures below demonstrate a nitrogen arrangement of one embodiment of the compounds of Formula 5:

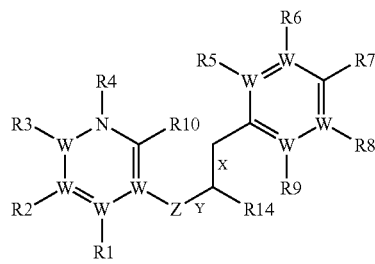

wherein the same applies to any W; or

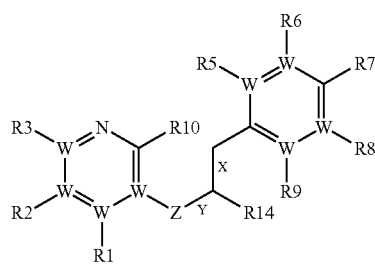

wherein the same applies to any W:
wherein

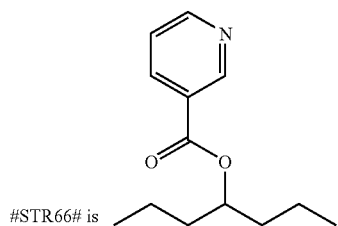

STR66# is wherein
X can be single or double bond;
Y can be single or double bond;
Z can be O, C, N, S, CR13, or NR13;
wherein
R13 is #STR77#, #STR88#, #STR99#, or #STR100#,
wherein

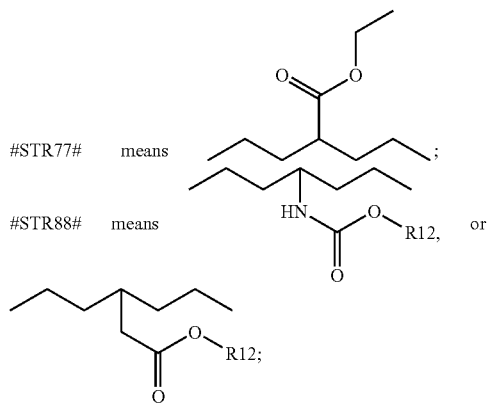

STR77# means

STR88# means

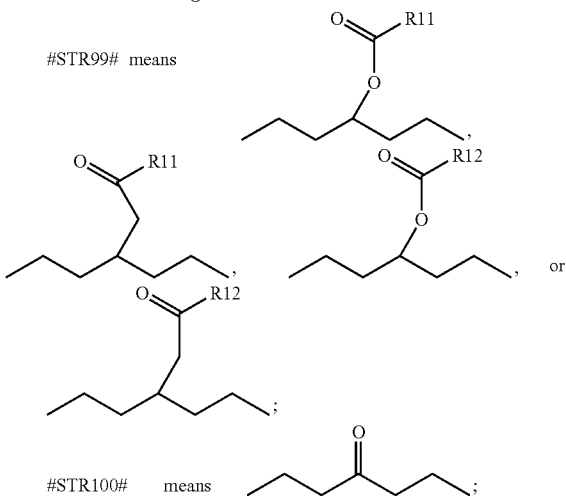

STR99# means

STR100# means

R11 is pyridine, pyridazine, pyrimidine, pyrazine; and
R12 is $(C_1-C_{22})$alkyl, $(C_2-C_{22})$alkenyl, aryl, heteroaryl or a derivative thereof, wherein said derivative is optionally substituted and optionally branched, and may have one or more of the C atoms replaced by S, N or O;
with the proviso that;
a) R7 is a hydroxyl; OR
b) R7 is a hydroxyl, and optionally;
c) at least one W is a N, and/or;
d) at least one of R1-10 is #STR77#, or #STR88#, or #STR99#, and/or;
e) at least one of R1-R10 is #STR66#.

Another alternative embodiment provides compounds comprising the general chalcone structure of Formula 5:

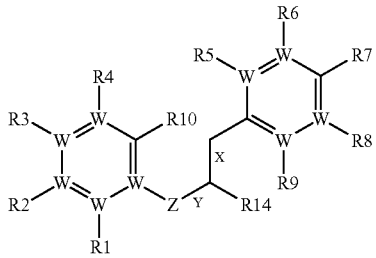

or a pharmaceutically acceptable salt thereof,
wherein
R1, R2, R3, R4, R5, R6, R8, R9, and R10 are independently selected from the group consisting of $(C_1-C_{22})$alkyl, $(C_2-C_{22})$alkenyl, aryl, heteroaryl, hydrogen, hydroxyl [OH], acetyl, hydroxyalkyl, aminoalkyl, Bromide [Br], Iodide [I], methoxy [OCH$_3$], ethoxy [OCH$_2$CH$_3$], fluoride [F], chloride [Cl], CF$_3$, CCl$_3$, phosphate, O-sulfate [the sulfate conjugate], O-glucoronidate [the glucoronic (AKA glucuronic) acid conjugates], #STR66#, #STR77#, #STR88#, #STR99#, #STR100#
wherein
W can be C or N;
wherein when W is an nitrogen atom, the nitrogen atom will only bind to three covalent bonds due to available valence electrons.

The structures below demonstrate a nitrogen arrangement of one embodiment of the compounds of Formula 5:

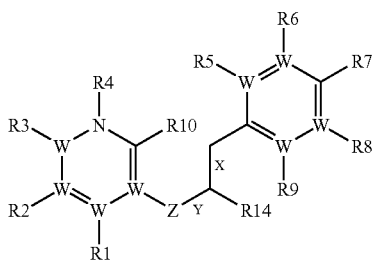

wherein the same applies to any W; or

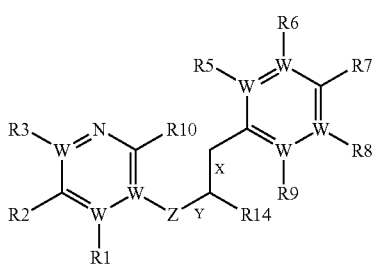

wherein the same applies to any W:
wherein

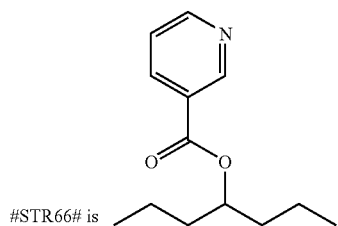

STR66# is wherein
X can be single or double bond;
Y can be single or double bond;
Z can be O, C, N, S, CR13, or NR13;
wherein
R13 is #STR77#, #STR88#, #STR99#, or #STR100#,
wherein

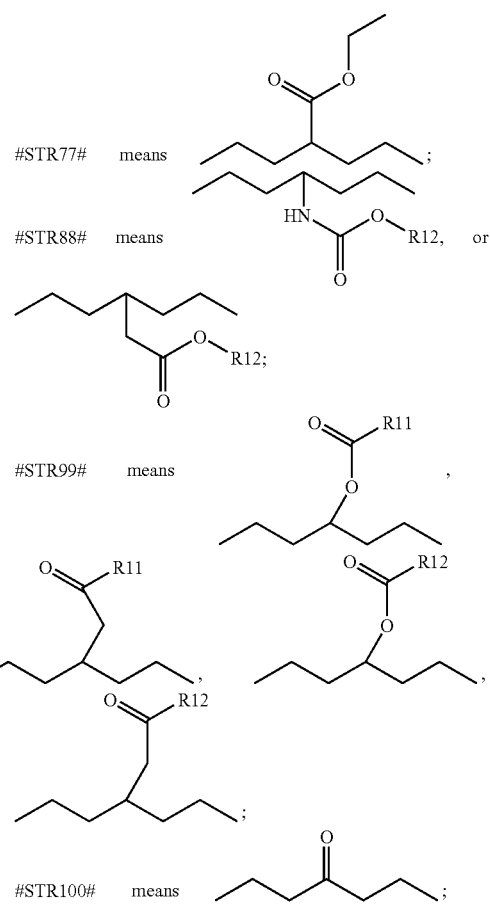

R11 is pyridine, pyridazine, pyrimidine, pyrazine; and
R12 is $(C_1-C_{22})$alkyl, $(C_2-C_{22})$alkenyl, aryl, heteroaryl or a derivative thereof, wherein said derivative is optionally substituted and optionally branched, and may have one or more of the C atoms replaced by S, N or O;
with the proviso that;
  a) at least one W is a N and R7 is a hydroxyl; or
  b) at least one W is a N and R7 is a hydroxyl, and optionally;
  c) at least one of R1-10 is #STR77#, or #STR88#, or #STR99#, and/or;
  d) at least one of R1-R10 is #STR66#.

Another alternative embodiment provides compounds comprising of the chalcone structure of Formula 5:

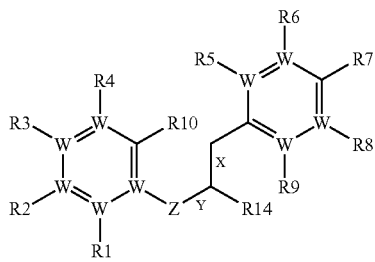

or a pharmaceutically acceptable salt thereof,
wherein
R1, R2, R3, R4, R5, R6, R8, R9, and R10 are independently selected from the group consisting of $(C_1-C_{22})$alkyl, $(C_2-C_{22})$alkenyl, aryl, heteroaryl, hydrogen, hydroxyl [OH], acetyl, hydroxyalkyl, aminoalkyl, Bromide [Br], Iodide [I], methoxy [OCH$_3$], ethoxy [OCH$_2$CH$_3$], fluoride [F], chloride [Cl], CF$_3$, CCl$_3$, phosphate, O-sulfate [the sulfate conjugate], O-glucoronidate [the glucoronic (AKA glucuronic) acid conjugates], #STR66#, #STR77#, #STR88#, #STR99#, #STR100# wherein W can be C or N;

wherein when W is an nitrogen atom, the nitrogen atom will only bind to three covalent bonds due to available valence electrons. The structures below demonstrate a nitrogen arrangement of one embodiment of the compounds of Formula 5:

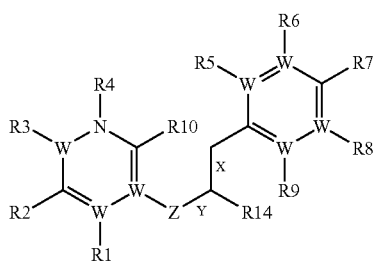

wherein the same applies to any W; or

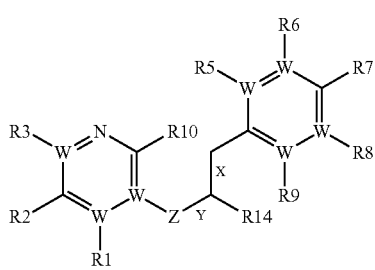

wherein the same applies to any W:
wherein

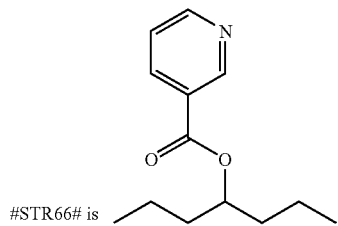

STR66# is wherein
X can be single or double bond;
Y can be single or double bond;
Z can be O, C, N, S, CR13, or NR13;
wherein
R13 is #STR77#, #STR88#, #STR99#, or #STR100#,
wherein

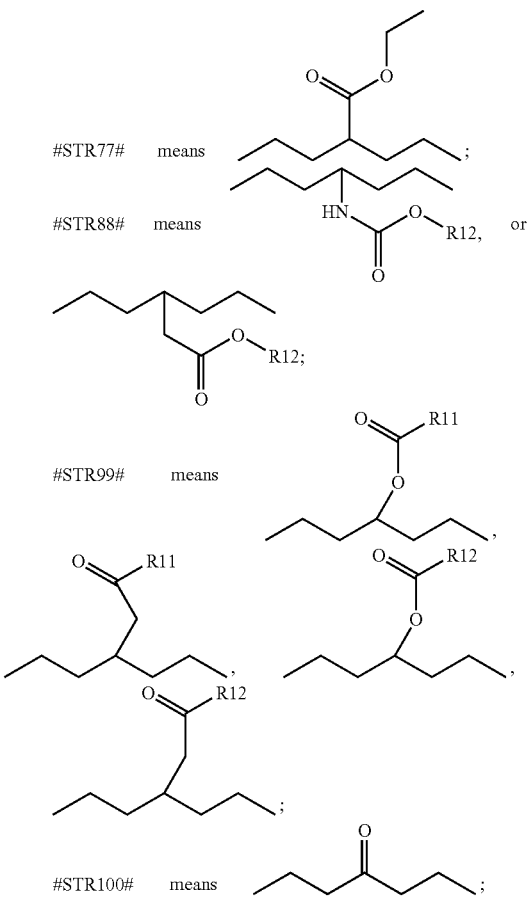

STR77# means

STR88# means

STR99# means

STR100# means

R11 is pyridine, pyridazine, pyrimidine, pyrazine; and
R12 is $(C_1-C_{22})$alkyl, $(C_2-C_{22})$alkenyl, aryl, heteroaryl or a derivative thereof, wherein said derivative is optionally substituted and optionally branched, and may have one or more of the C atoms replaced by S, N or O;
with the proviso that;
a) at least one of R1-10 is selected from #STR77# or #STR88# or #STR99#, and R7 is a hydroxyl;

b) at least one of R1-10 is selected from #STR77# or #STR88# or #STR99#, and R7 is a hydroxyl, and optionally;
c) at least one W is a N, and/or;
d) at least one of R1-R10 is #STR66#.

Another alternative embodiment provides compounds comprising the chalcone structure of Formula 5:

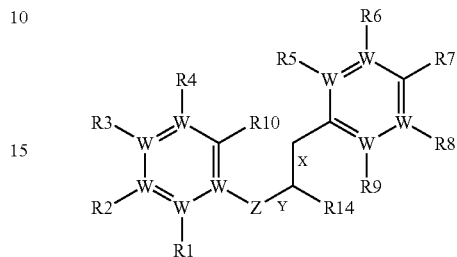

or a pharmaceutically acceptable salt thereof,
wherein
R1, R2, R3, R4, R5, R6, R8, R9, and R10 are independently selected from the group consisting of $(C_1-C_{22})$alkyl, $(C_2-C_{22})$alkenyl, aryl, heteroaryl, hydrogen, hydroxyl [OH], acetyl, hydroxyalkyl, aminoalkyl, Bromide [Br], Iodide [I], methoxy [$OCH_3$], ethoxy [$OCH_2CH_3$], fluoride [F], chloride [Cl], $CF_3$, $CCl_3$, phosphate, O-sulfate [the sulfate conjugate], O-glucoronidate [the glucuronic (AKA glucuronic) acid conjugates], #STR66#, #STR77#, #STR88#, #STR99#, #STR100#
wherein
W can be C or N;
wherein when W is an nitrogen atom, the nitrogen atom will only bind to three covalent bonds due to available valence electrons.

The structures below demonstrate a nitrogen arrangement of one embodiment of the compounds of Formula 5:

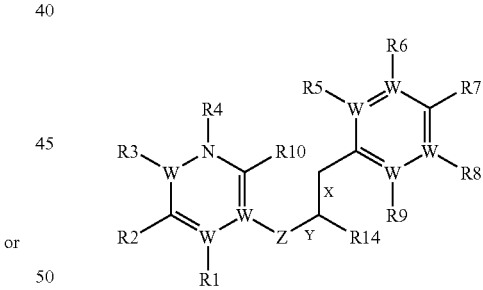

wherein the same applies to any W; or

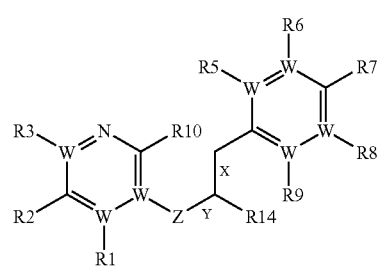

wherein the same applies to any W:
wherein

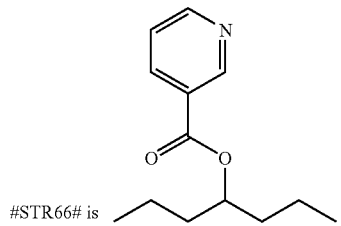

STR66# is wherein
X can be single or double bond;
Y can be single or double bond;
Z can be O, C, N, S, CR13, or NR13;
wherein
R13 is #STR77#, #STR88#, #STR99#, or #STR100#,
wherein

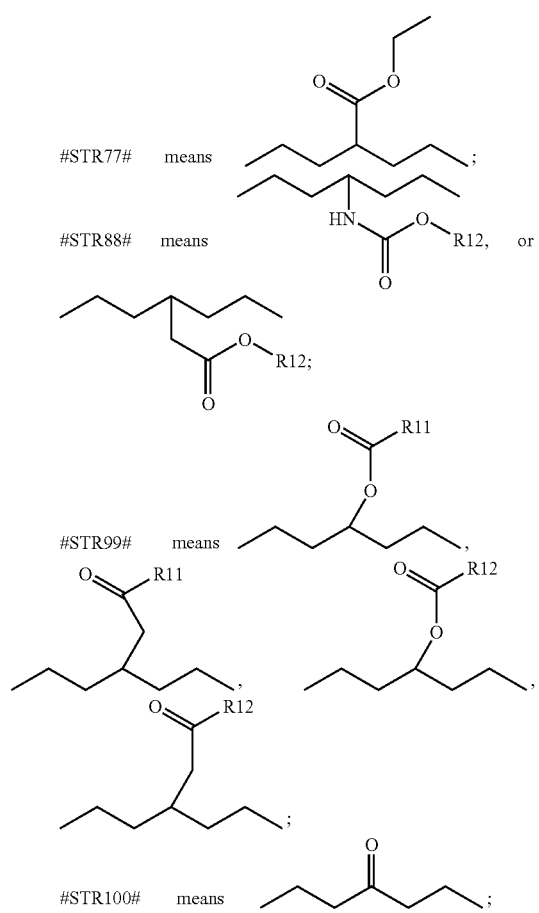

R11 is pyridine, pyridazine, pyrimidine, pyrazine; and
R12 is $(C_1-C_{22})$alkyl, $(C_2-C_{22})$alkenyl, aryl, heteroaryl or a derivative thereof, wherein said derivative is optionally substituted and optionally branched, and may have one or more of the C atoms replaced by S, N or O;
with the proviso that;
a) R7 is a hydroxyl or #STR66# and if R7 is a hydroxyl at least one of (R1-R6 and R8-R10) is #STR66#; or
b) R7 is a hydroxyl or #STR66# and if R7 is a hydroxyl at least one of (R1-R6 and R8-R10) is #STR66# and optionally;
c) at least one W is a N, and/or;
d) at least one of R1-10 is #STR77#, or #STR88#, or #STR99#.

Another alternative embodiment provides compounds comprising, the chalcone structure of Formula 5:

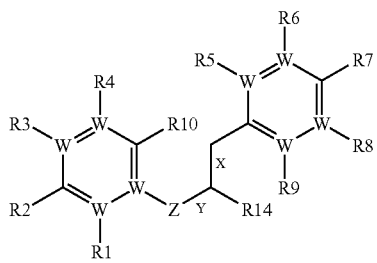

or a pharmaceutically acceptable salt thereof,
wherein
R1, R2, R3, R4, R5, R6, R8, R9, and R10 are independently selected from the group consisting of $(C_1-C_{22})$alkyl, $(C_2-C_{22})$alkenyl, aryl, heteroaryl, hydrogen, hydroxyl [OH], acetyl, hydroxyalkyl, aminoalkyl, Bromide [Br], Iodide [I], methoxy [$OCH_3$], ethoxy [$OCH_2CH_3$], fluoride [F], chloride [Cl], $CF_3$, $CCl_3$, phosphate, O-sulfate [the sulfate conjugate], O-glucoronidate [the glucuronic (AKA glucuronic) acid conjugates], #STR66#, #STR77#, #STR88#, #STR99#, #STR100#
wherein
W can be C or N;
wherein when W is an nitrogen atom, the nitrogen atom will only bind to three covalent bonds due to available valence electrons. The structures below demonstrate a nitrogen arrangement of one embodiment of the compounds of Formula 5:

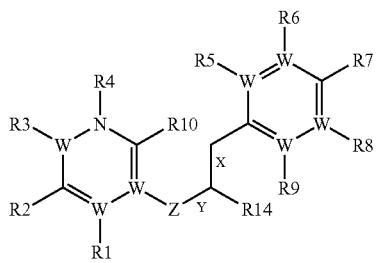

wherein the same applies to any W; or

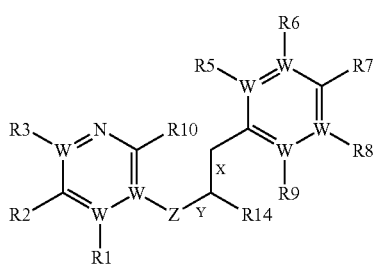

wherein the same applies to any W:
wherein

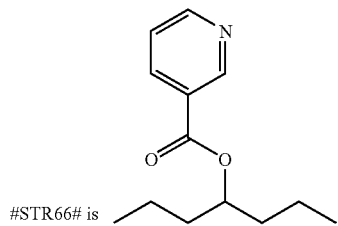

STR66# is wherein
X can be single or double bond;
Y can be single or double bond;
Z can be O, C, N, S, CR13, or NR13;
wherein
R13 is #STR77#, #STR88#, #STR99#, or #STR100#,
wherein

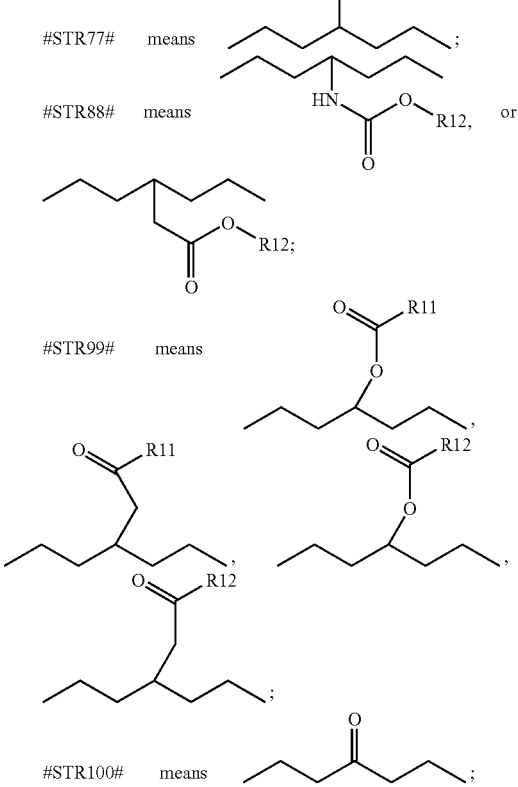

R11 is pyridine, pyridazine, pyrimidine, pyrazine; and
R12 is $(C_1\text{-}C_{22})$alkyl, $(C_2\text{-}C_{22})$alkenyl, aryl, heteroaryl or a derivative thereof, wherein said derivative is optionally substituted and optionally branched, and may have one or more of the C atoms replaced by S, N or O;
with the proviso that;
a) R7 is a hydroxyl or #STR66#, and
b) at least one W is a N, and
c) at least one of R1-10 is #STR77#, or #STR88#, or #STR99#, and
d) at least one of R1-R10 is #STR66#.

Non-limiting examples of chalcone compounds of Formula 5 include:

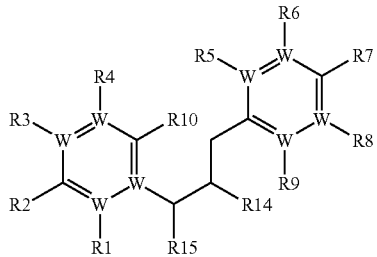
(XLIX)

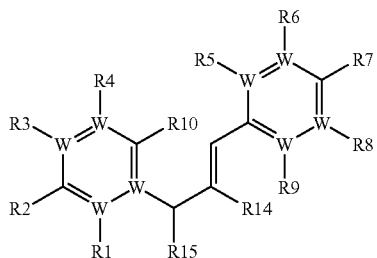
(L)

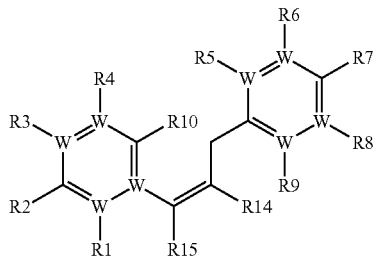
(LI)

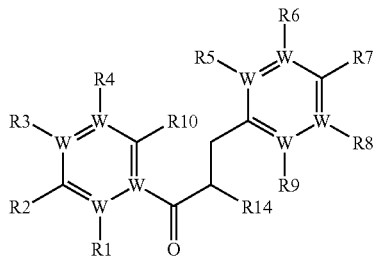
(LII)

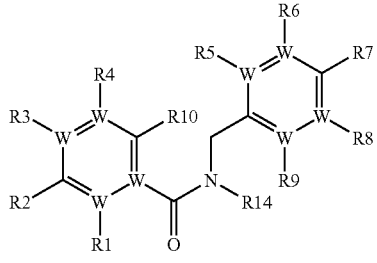
(LIII)

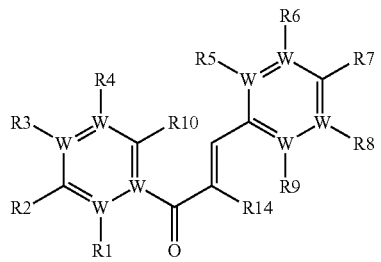
(LIV)
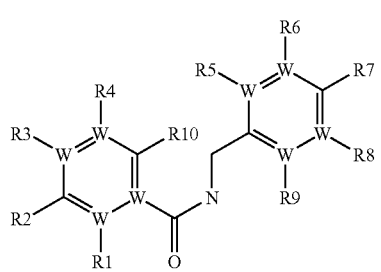
(LV)
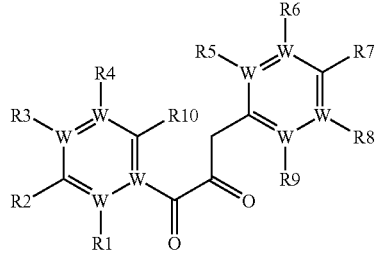
(LVI)
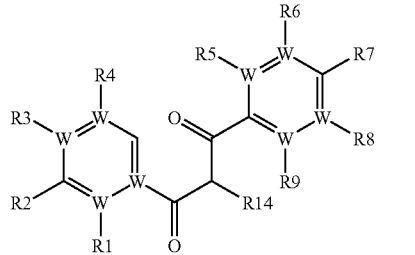
(LVII)
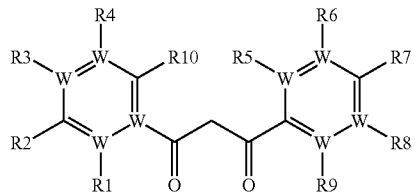
(LVIII)
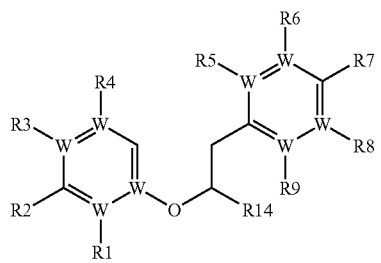
(LIX)
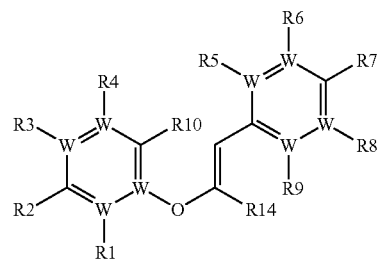
(LX)
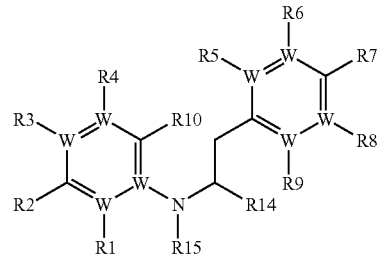
(LXI)
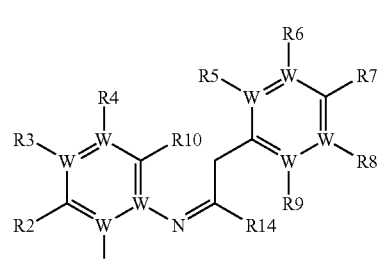
(LXII)
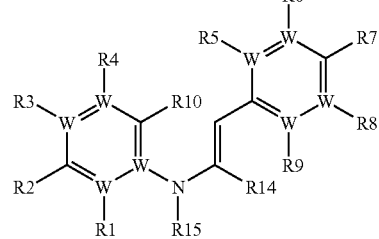
(LXIII)
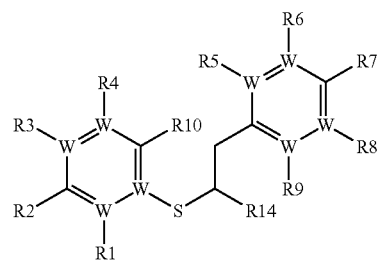
(LXIV)
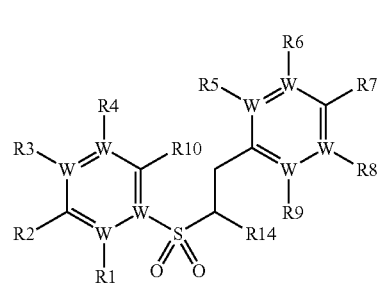
(LXV)

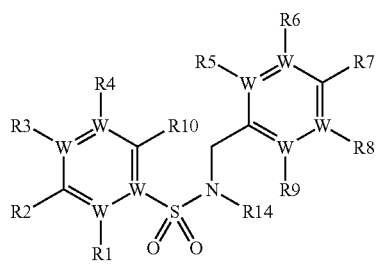
(LXVI)

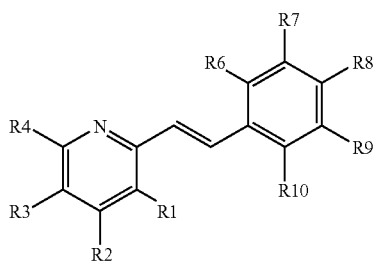
(LXVII)

wherein the same applies to any W; or

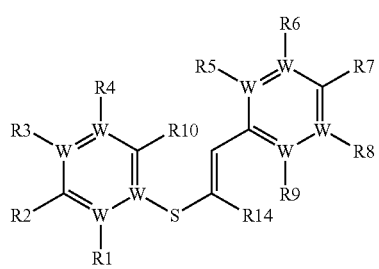

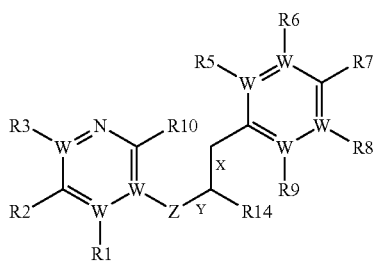

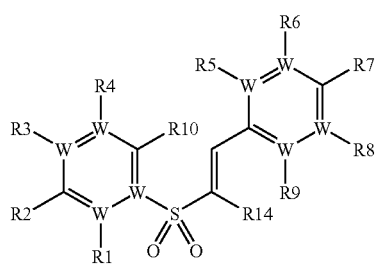
(LXVIII)

wherein the same applies to any W:
wherein

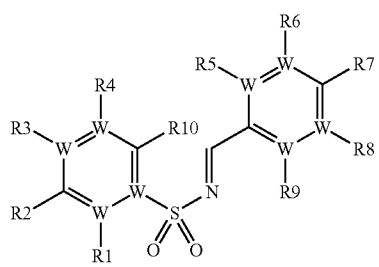
(LXIX)

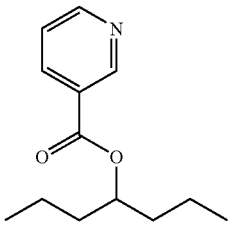

STR66# is wherein
X can be single or double bond;
Y can be single or double bond;
Z can be O, C, N, S, CR13, or NR13;
wherein
R13 is #STR77#, #STR88#, #STR99#, or #STR100#,
wherein or a pharmaceutically acceptable salt thereof,
wherein
R1, R2, R3, R4, R5, R6, R8, R9, R10, R14, and R15 are independently selected from the group consisting of $(C_1-C_{22})$alkyl, $(C_2-C_{22})$alkenyl, aryl, heteroaryl, hydrogen, hydroxyl [OH], acetyl, hydroxyalkyl, aminoalkyl, Bromide [Br], Iodide [I], methoxy [OCH$_3$], ethoxy [OCH$_2$CH$_3$], fluoride [F], chloride [Cl], CF$_3$, CCl$_3$, phosphate, O-sulfate [the sulfate conjugate], O-glucoronidate [the glucuronic (AKA glucuronic) acid conjugates], #STR66#, #STR77#, #STR88#, #STR99#, #STR100#
wherein can be C or N;
wherein when W is an nitrogen atom, the nitrogen atom will only bind to three covalent bonds due to available valence electrons.

The structures below demonstrate a nitrogen arrangement of one embodiment of the compounds of Formula 5:

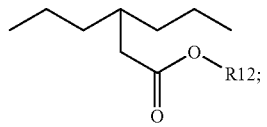

STR77# means 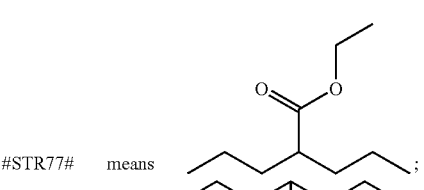

STR88# means 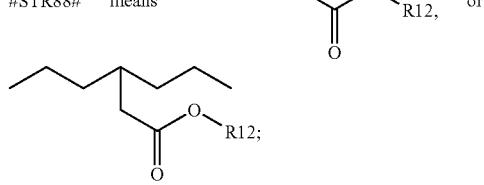

or

-continued

STR99# means

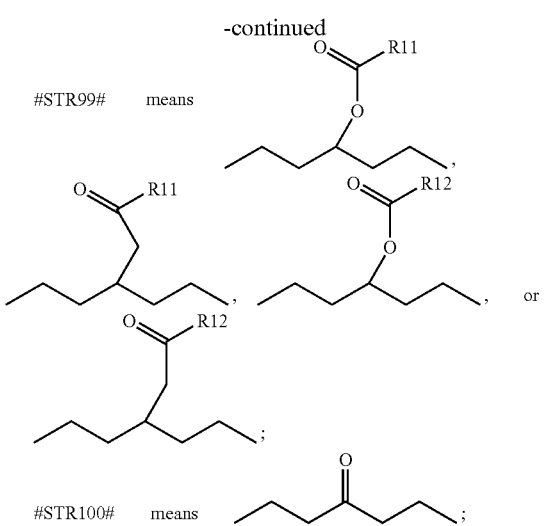

STR100# means

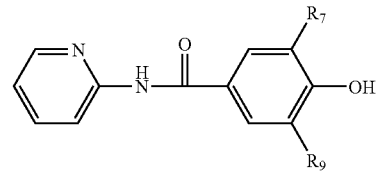

R11 is pyridine, pyridazine, pyrimidine, pyrazine; and
R12 is $(C_1-C_{22})$alkyl, $(C_2-C_{22})$alkenyl, aryl, heteroaryl or a derivative thereof, wherein said derivative is optionally substituted and optionally branched, and may have one or more of the C atoms replaced by S, N or O;
wherein the compounds of Formula 5 have at least one of the following groups of provisos:
1) with the proviso that;
   a) R7 is a hydroxyl; or
   b) R7 is a hydroxyl, and optionally;
   c) at least one W is a N, and/or;
   d) at least one of R1-10 is #STR77#, or #STR88#, or #STR99#, and/or;
   e) at least one of R1-R10 is #STR66#.
2) with the proviso that;
   a) at least one W is a N and R7 is a hydroxyl; or
   b) at least one W is a N and R7 is a hydroxyl, and optionally;
   c) at least one of R1-10 is #STR77#, or #STR88#, or #STR99#, and/or;
   d) at least one of RI-R10 is #STR66#.
3) with the proviso that;
   a) at least one of R1-10 is selected from #STR77# or #STR88# or #STR99#, and R7 is a hydroxyl; or
   b) at least one of R1-10 is selected from #STR77# or #STR88# or #STR99#, and R7 is a hydroxyl, and optionally;
   c) at least one W is a N, and/or;
   d) at least one of R1-R10 is #STR66#.
4) with the proviso that;
   a) R7 is a hydroxyl or #STR66# and if R7 is a hydroxyl at least one of (R1-R6 and R8-R10) is #STR66#; or
   b) R7 is a hydroxyl or #STR66# and if R7 is a hydroxyl at least one of (R1-R6 and R8-R10) is #STR66# and optionally;
   c) at least one W is a N, and/or;
   d) at least one of R1-10 is #STR77#, or #STR88#, or #STR99#, and/or;
5) with the proviso that;
   a) R7 is a hydroxyl or #STR66#, and
   b) at least one W is a N, and
   c) at least one of R1-10 is #STR77#, or #STR88#, or #STR99#, and
   d) at least one of R1-R10 is #STR66#.

The following is a list of specific exemplary embodiments encompassed by the invention:

1. A method for increasing expression of ApoA-I in a mammal comprising administering a therapeutically effective amount of a compound of Formula I:

Formula I

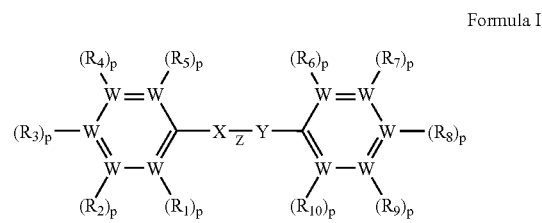

wherein:
X is selected from C, $CR_{11}$, $CR_{11}R_{13}$, CO, CS, O, S, SO, $SO_2$, N and $NR_{11}$, wherein $R_{11}$ may be the same or different than $R_{13}$;
Y is selected from C, $CR_{12}$, $CR_{12}R_{14}$, CO, CS, O, S, SO, $SO_2$, N and $NR_{12}$, wherein $R_{12}$ may be the same or different than $R_{14}$;
$R_1, R_2, R_3, R_4, R_5, R_6, R_7, R_8, R_9, R_{10}, R_{11}, R_{12}, R_{13}$, and $R_{14}$ are each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone, or
two adjacent substituents selected from $R_1, R_2, R_3, R_4, R_5, R_6, R_7, R_8, R_9, R_{10}, R_{11}, R_{12}, R_{13}$, and $R_{14}$ are connected in a 5 or 6-membered ring to form a bicyclic aryl or bicyclic heteroaryl;
each W is independently selected from C and N, wherein if W is N, then p is 0 and if W is C, then p is 1;
Z is selected from a single bond, a double bond and a triple bond;
and pharmaceutically acceptable salts and hydrates thereof;
wherein if $R_3$ and $R_8$ are each hydroxyl, then at least one of $R_{11}$ and $R_{12}$ is not alkyl;
wherein if Z is a double bond, then $R_2, R_4$ and $R_8$ are not each hydroxyl; and
wherein if Formula 1 has the structure:

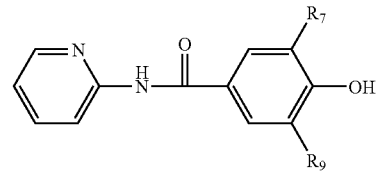

then at least one of $R_7$ and $R_9$ is not alkyl.
2. The method of embodiment 1, wherein at least one W is N.
3. The method of embodiment 1, wherein $R_8$ is hydroxyl, and $R_7$ and $R_9$ are independently selected from arylalkyl, carboxy, cyano, cycloalkyl, ester, formyl, halogen, haloalkyl, heteroaryl, heterocyclyl, hydrogen, hydroxyl, hydroxyalkyl, hydroxyaryl, ketone, perfluoroalkyl, perfluorocyclolkyl, perfluoralkoxy, trichloromethyl, O-sulfate, and O-glucoronidate, subject to the proviso that $R_7$ and $R_9$ are not both simultaneously hydrogen.
4. The method of embodiment 3, wherein at least one W is N.
5. The method of embodiment 1, wherein at least one of $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ is selected from O-sulfate and O-glucoronidate.
6. The method of embodiment 5, wherein at least one W is N.
7. The method of embodiment 1, wherein at least one of $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ is selected from succinate, D-argininate, L-argininate, L-lysinate and D-lysinate.
8. The method of embodiment 7, wherein at least one W is N.
9. The method of embodiment 1, wherein at least one of $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ is selected from amide, amino, carbamate, carboxy, ester, ether, formyl, and ketone.
10. The method of embodiment 9, wherein at least one W is N.
11. The method of embodiment 9, wherein at least one of $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ is a nicotinate ester.
12. The method of embodiment 11, wherein at least one W is N.
13. The method of embodiment 1, wherein Z is a single bond.
14. The method of embodiment 13 wherein $R_8$ is hydroxyl, and $R_7$ and $R_9$ are independently selected from arylalkyl, carboxy, cyano, cycloalkyl, ester, formyl, halogen, haloalkyl, heteroaryl, heterocyclyl, hydrogen, hydroxyl, hydroxyalkyl, hydroxyaryl, ketone, perfluoroalkyl, perfluorocyclolkyl, perfluoralkoxy, trichloromethyl, O-sulfate, and O-glucoronidate, subject to the proviso that $R_7$ and $R_9$ are not both simultaneously hydrogen.
15. The method of embodiment 13, wherein at least one W is N.
16. The method of embodiment 14, wherein at least one W is N.
17. The method of embodiment 13, wherein X is $CR_{11}R_{13}$ and Y is $CR_{12}R_{14}$.
18. The method of embodiment 17, wherein $R_8$ is hydroxyl, and $R_7$ and $R_9$ are independently selected from arylalkyl, carboxy, cyano, cycloalkyl, ester, formyl, halogen, haloalkyl, heteroaryl, heterocyclyl, hydrogen, hydroxyl, hydroxyalkyl, hydroxyaryl, ketone, perfluoroalkyl, perfluorocyclolkyl, perfluoralkoxy, trichloromethyl, O-sulfate, and O-glucoronidate, subject to the proviso that $R_7$ and $R_9$ are not both simultaneously hydrogen.
19. The method of embodiment 17, wherein at least one W is N.
20. The method of embodiment 18, wherein at least one W is N.
21. The method of embodiment 13, wherein X is $NR_{11}$, and Y is $NR_{12}$.
22. The method of embodiment 21, wherein $R_8$ is hydroxyl, and $R_7$ and $R_9$ are independently selected from
arylalkyl, carboxy, cyano, cycloalkyl, ester, formyl, halogen, haloalkyl, heteroaryl, heterocyclyl, hydrogen, hydroxyl, hydroxyalkyl, hydroxyaryl, ketone, perfluoroalkyl, perfluorocyclolkyl, perfluoralkoxy, trichloromethyl, O-sulfate, and O-glucoronidate, subject to the proviso that $R_7$ and $R_9$ are not both simultaneously hydrogen.
23. The method of embodiment 21, wherein at least one W is N.
24. The method of embodiment 22, wherein at least one W is N.
25. The method of embodiment 1, wherein Z is a double bond.
26. The method of embodiment 25, wherein the double bond is an E-double bond.
27. The method of embodiment 25, wherein $R_8$ is hydroxyl, and $R_7$ and $R_9$ are independently selected from
arylalkyl, carboxy, cyano, cycloalkyl, ester, formyl, halogen, haloalkyl, heteroaryl, heterocyclyl, hydrogen, hydroxyl, hydroxyalkyl, hydroxyaryl, ketone, perfluoroalkyl, perfluorocyclolkyl, perfluoralkoxy, trichloromethyl, O-sulfate, and O-glucoronidate,
subject to the proviso that $R_7$ and $R_9$ are not both simultaneously hydrogen.
28. The method of embodiment 25, wherein at least one W is N.
29. The method of embodiment 27, wherein at least one W is N.
30. The method of embodiment 25, wherein X is N and Y is N.
31. The method of embodiment 30, wherein $R_8$ is hydroxyl, and $R_7$ and $R_9$ are independently selected from
arylalkyl, carboxy, cyano, cycloalkyl, ester, formyl, halogen, haloalkyl, heteroaryl, heterocyclyl, hydrogen, hydroxyl, hydroxyalkyl, hydroxyaryl, ketone, perfluoroalkyl, perfluorocyclolkyl, perfluoralkoxy, trichloromethyl, O-sulfate, and O-glucoronidate,
subject to the proviso that $R_7$ and $R_9$ are not both simultaneously hydrogen.
32. The method of embodiment 30, wherein at least one W is N.
33. The method of embodiment 31, wherein at least one W is N.
34. The method of embodiment 25, wherein X is $CR_{11}$ and Y is $CR_{12}$.
35. The method of embodiment 34, wherein $R_8$ is hydroxyl, and $R_7$ and $R_9$ are independently selected from
arylalkyl, carboxy, cyano, cycloalkyl, ester, formyl, halogen, haloalkyl, heteroaryl, heterocyclyl, hydrogen, hydroxyl, hydroxyalkyl, hydroxyaryl, ketone, perfluoroalkyl, perfluorocyclolkyl, perfluoralkoxy, trichloromethyl, O-sulfate, and O-glucoronidate,
subject to the proviso that $R_7$ and $R_9$ are not both simultaneously hydrogen.
36. The method of embodiment 34, wherein at least one W is N.
37. The method of embodiment 35, wherein at least one W is N.
38. The method of embodiment 1, wherein Z is a triple bond.
39. The method of embodiment 38, wherein $R_8$ is hydroxyl, and $R_7$ and $R_9$ are independently selected from
arylalkyl, carboxy, cyano, cycloalkyl, ester, formyl, halogen, haloalkyl, heteroaryl, heterocyclyl, hydrogen, hydroxyl, hydroxyalkyl, hydroxyaryl, ketone, perfluoroalkyl, perfluorocyclolkyl, perfluoralkoxy, trichloromethyl, O-sulfate, and O-glucoronidate, subject to the proviso that $R_7$ and $R_9$ are not both simultaneously hydrogen.
40. The method of embodiment 38, wherein at least one W is N.
41. The method of embodiment 39, wherein at least one W is N.
42. The method of embodiment 1, wherein Formula I has the structure:

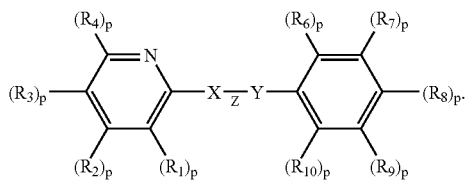

43. The method of embodiment 42, wherein $R_8$ is hydroxyl, and $R_7$ and $R_9$ are independently selected from arylalkyl, carboxy, cyano, cycloalkyl, ester, formyl, halogen, haloalkyl, heteroaryl, heterocyclyl, hydrogen, hydroxyl, hydroxyalkyl, hydroxyaryl, ketone, perfluoroalkyl, perfluorocyclolkyl, perfluoralkoxy, O-sulfate, and O-glucoronidate, subject to the proviso that $R_7$ and $R_9$ are not both simultaneously hydrogen.

44. The method of embodiment 42, wherein at least one W is N.

45. The method of embodiment 43, wherein at least one W is N.

46. The method of embodiment 1, wherein Formula I has the structure:

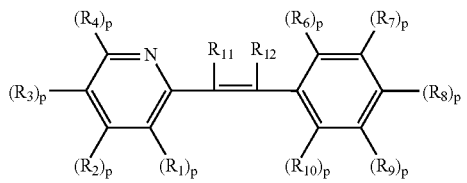

47. The method of embodiment 46, wherein $R_8$ is hydroxyl, and $R_7$ and $R_9$ are independently selected from arylalkyl, carboxy, cyano, cycloalkyl, ester, formyl, halogen, haloalkyl, heteroaryl, heterocyclyl, hydrogen, hydroxyl, hydroxyalkyl, hydroxyaryl, ketone, perfluoroalkyl, perfluorocyclolkyl, perfluoralkoxy, O-sulfate, and O-glucoronidate, subject to the proviso that $R_7$ and $R_9$ are not both simultaneously hydrogen.

48. The method of embodiment 46, wherein at least one W is N.

49. The method of embodiment 47, wherein at least one W is N.

50. The method of embodiment 1, wherein:

X is selected from $CR_{11}$, $CR_{11}R_{13}$, N and $NR_{11}$, wherein $R_{11}$, may be the same or different than $R_{13}$; and Y is selected from $CR_{12}$, $CR_{12}R_{14}$, N and $NR_{12}$, wherein $R_{12}$ may be the same or different than $R_{14}$.

51. The method of embodiment 50 wherein $R_8$ is hydroxyl, and $R_7$ and $R_9$ are independently selected from arylalkyl, carboxy, cyano, cycloalkyl, ester, formyl, halogen, haloalkyl, heteroaryl, heterocyclyl, hydrogen, hydroxyl, hydroxyalkyl, hydroxyaryl, ketone, perfluoroalkyl, perfluorocyclolkyl, perfluoralkoxy, O-sulfate, and O-glucoronidate, subject to the proviso that $R_7$ and $R_9$ are not both simultaneously hydrogen.

52. The method of embodiment 50, wherein at least one W is N.

53. The method of embodiment 51, wherein at least one W is N

54. The method of embodiment 1, wherein X is selected from N and $NR_{11}$, and Y is selected from N and $NR_{12}$.

55. The method of embodiment 54 wherein $R_8$ is hydroxyl, and $R_7$ and $R_9$ are independently selected from arylalkyl, carboxy, cyano, cycloalkyl, ester, formyl, halogen, haloalkyl, heteroaryl, heterocyclyl, hydrogen, hydroxyl, hydroxyalkyl, hydroxyaryl, ketone, perfluoroalkyl, perfluorocyclolkyl, perfluoralkoxy, O-sulfate, and O-glucoronidate, subject to the proviso that $R_7$ and $R_9$ are not both simultaneously hydrogen.

56. The method of embodiment 54, wherein at least one W is N.

57. The method of embodiment 55, wherein at least one W is N.

58. The method of embodiment 1, wherein the therapeutically effective amount of the compound of Formula I is sufficient to establish a concentration ranging from about 0.001 μM to about 100 μM in the mammal.

59. The method of embodiment 2, wherein the concentration ranges from about 1 μM to about 20 μM.

60. The method of embodiment 1, wherein the therapeutically effective amount of the compound of Formula I is administered with a pharmaceutically acceptable carrier in a pharmaceutically acceptable composition.

61. A method for increasing expression of ApoA-I in a mammal comprising administering a therapeutically effective amount of a compound of Formula II:

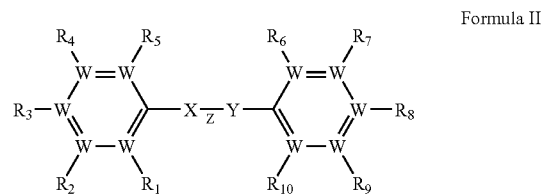

Formula II wherein:

X is selected from CH, $CH_2$, $CR_{11}$, $CR_{13}$, $CHR_{11}$, $CHR_{13}$, $CR_{11}R_{13}$, CO, CS, O, S, SO, $SO_2$, NH and $NR_{11}$, wherein $R_{11}$ may be the same or different than $R_{13}$;

Y is selected from CH, $CH_2$, $CHR_{12}$, $CHR_{14}$, $CR_{12}$, $CR_{14}$, $CR_{12}R_{14}$, CO, CS, O, S, SO, $SO_2$, NH and $NR_{12}$, wherein $R_{12}$ may be the same or different than $R_{14}$;

$R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ are each independently selected from ($C_1$-$C_{22}$)alkyl, ($C_2$-$C_{22}$)alkenyl, ($C_2$-$C_{22}$)alkynyl, aryl, heteroaryl, alkoxy, aryloxy, benzyl, phenyl, carbonyl, thioketone, hydrogen, hydroxyl, acetyl, hydroxyalkyl, aminoalkyl, amide, carbamate, halogen, $CF_3$, $CCl_3$, sulfonic acid, phosphate, O-sulfate, O-glucoronidate, monoester, dicarboxylic acid, J, K, L, M, P and Q;

each W is independently selected from C and N;

Z is selected from a single bond, a double bond, and a triple bond;

J is selected from

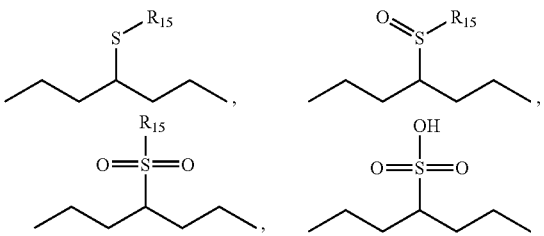

-continued

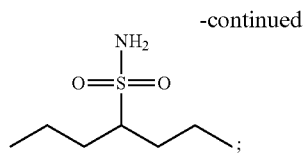

and
K is

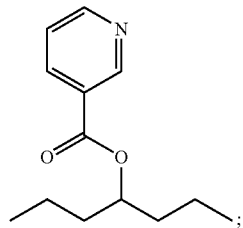

L is selected from

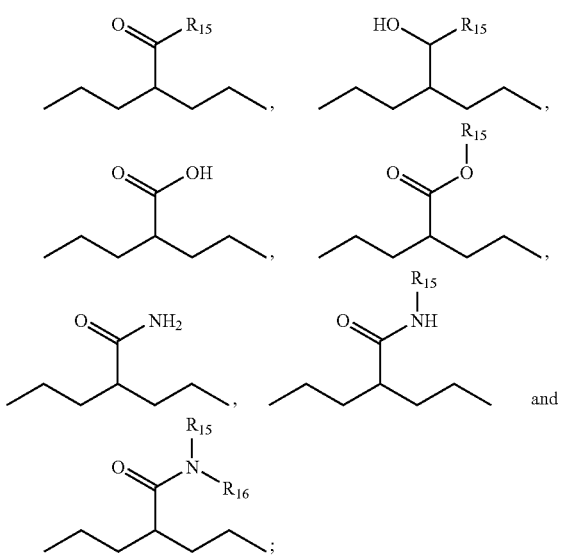

M is selected from

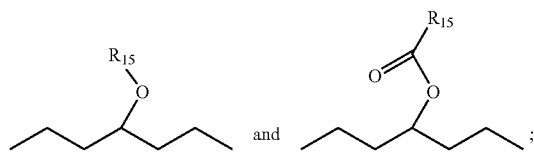

P is selected from

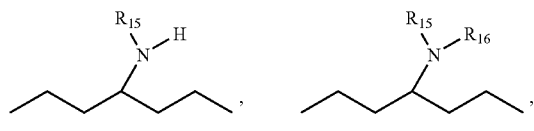

-continued

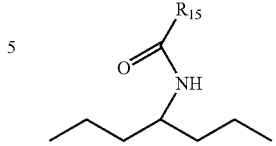
and ;

Q is selected from

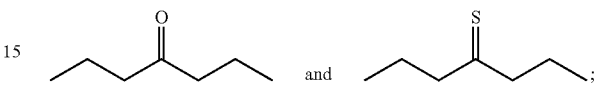
and ;

$R_{15}$ and $R_{16}$ are each independently selected from $(C_1-C_{22})$ alkyl, $(C_2-C_{22})$alkenyl, $(C_2-C_{22})$alkynyl, aryl, heteroaryl, alkoxy, aryloxy, benzyl, phenyl, carbonyl, hydrogen, hydroxyl, acetyl, hydroxyalkyl, aminoalkyl, amide, carbamate, halogen, $CF_3$, $CCl_3$, sulfonic acid and phosphate;

and pharmaceutically acceptable salts thereof;

subject to at least one proviso selected from:
1) $R_8$ is hydroxyl;
2) at least one W is N;
3) at least one of $R_1-R_{12}$ is selected from L, M and P;
4) at least one of $R_1-R_{12}$ is selected from K;
5) $R_8$ is K;
6) one of $R_1-R_{12}$ is a monoester;
7) one of $R_1-R_{12}$ is a dicarboxylic acid;
8) one of $R_1-R_{12}$ is succinic acid;
9) $R_8$ and $R_3$ are each hydroxyl;
10) $R_8$ is selected from J; and
11) $R_8$ and $R_3$ are each selected from J.

62. The method of embodiment 61, wherein
if proviso 1 is selected, then at least one of provisos 3-8, 10 and 11 is selected;
if proviso 2 is selected, then at least one of provisos 3-8, 10 and 11 is selected; and
if proviso 9 is selected and Z is a double bond, then at least one of $R_{11}$ and $R_{12}$ is not alkyl.

63. The method of embodiment 61, wherein at least one proviso is selected from provisos 1, 2, 4, 5, and 9.

64. The method of embodiment 61, wherein $R_8$ is hydroxyl and at least one W is N.

65. The method of embodiment 61, wherein $R_8$ is hydroxyl and at least one of $R_1-R_7$ and $R_9-R_{12}$ is K.

66. The method of embodiment 61, wherein $R_8$ is hydroxyl and at least one of $R_1-R_7$ and $R_9-R_{12}$ is selected from L, M and P.

67. The method of embodiment 61, wherein $R_8$ is K and at least one W is N.

68. The method of embodiment 61, wherein Z is a single bond.

69. The method of embodiment 61, wherein Z is a double bond.

70. The method of embodiment 68, wherein X is $CR_{11}R_{13}$, and Y is $CR_{12}R_{14}$.

71. The method of embodiment 69, wherein X is $CR_{11}$, and Y is $CR_{12}$.

72. The method of embodiment 68, wherein X is $NR_{11}$, and Y is $NR_{12}$.

73. The method of embodiment 68, wherein X is $NR_{11}$, and Y is $CR_{12}R_{14}$.

74. The method of embodiment 68, wherein X is O, and Y is $CR_{12}R_{14}$.
75. The method of embodiment 68, wherein X is S, and Y is $CR_{12}R_{14}$.
76. The method of embodiment 68, wherein X is SO, and Y is $CR_{12}R_{14}$.
77. The method of embodiment 68, wherein X is $SO_2$, and Y is $CR_{12}R_{14}$.
78. The method of embodiment 68, wherein X is O, and Y is $NR_{12}$.
79. The method of embodiment 68, wherein X is S, and Y is $NR_{12}$.
80. The method of embodiment 68, wherein X is SO, and Y is $NR_{12}$.
81. The method of embodiment 68, wherein X is $SO_2$, and Y is $NR_{12}$.
82. The method of embodiment 68, wherein X is CO, and Y is $CR_{12}R_{14}$.
83. The method of embodiment 68, wherein X is CO, and Y is $NR_{12}$.
84. The method of embodiment 68, wherein X is CO, and Y is O.
85. The method of embodiment 68, wherein X is CO, and Y is S.
86. The method of embodiment 68, wherein X is CO, and Y is SO.
87. The method of embodiment 68, wherein X is CO, and Y is $SO_2$.
88. The method of embodiment 68, wherein X is SO, and Y is $NR_{12}$.
89. The method of embodiment 68, wherein X is SO, and Y is $CR_{12}R_{14}$.
90. The method of embodiment 61, wherein Formula II has the structure:

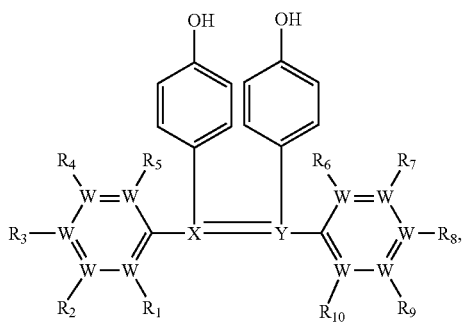

wherein the double bond is selected from an E-double bond and a Z-double bond.
91. The method of embodiment 90, wherein at least one W is N.
92. The method of embodiment 61, wherein Formula II has the structure:

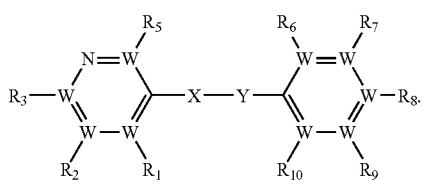

93. A method for increasing expression of ApoA-I in a mammal comprising administering a therapeutically effective amount of a compound selected from Formulae IIA and IIB:

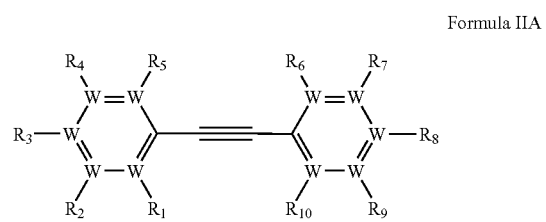

Formula IIA

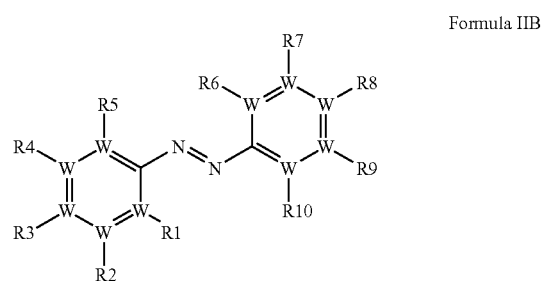

Formula IIB wherein:
$R_1$, $R_2$, $R_3$, $R_4$, $R_5$, $R_6$, $R_7$, $R_8$, $R_9$, and $R_{10}$ are each independently selected from $(C_1\text{-}C_{22})$alkyl, $(C_2\text{-}C_{22})$alkenyl, $(C_2\text{-}C_{22})$alkynyl, aryl, heteroaryl, alkoxy, aryloxy, benzyl, phenyl, carbonyl, thioketone, hydrogen, hydroxyl, acetyl, hydroxyalkyl, aminoalkyl, amide, carbamate, halogen, $CF_3$, $CCl_3$, sulfonic acid, phosphate, O-sulfate, O-glucoronidate, monoester, dicarboxylic acid, J, K, L, M, P and Q;
each W is independently selected from C and N;
J is selected from

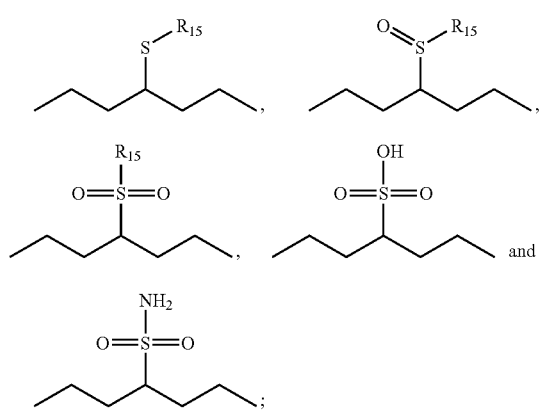

and

K is

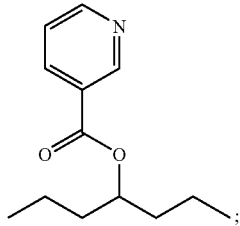

L is selected from

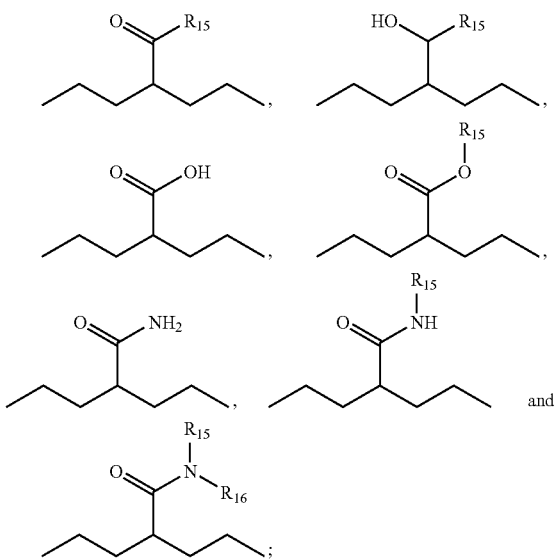

M is selected from

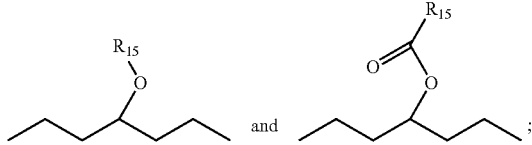

P is selected from

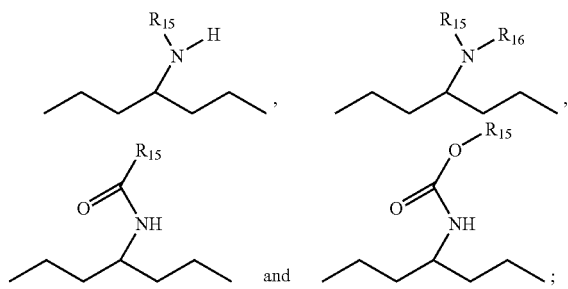

Q is selected from

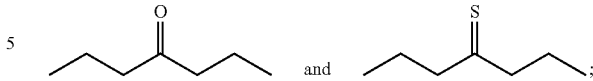

$R_{15}$ and $R_{16}$ are each independently selected from $(C_1-C_{22})$ alkyl, $(C_2-C_{22})$alkenyl, $(C_2-C_{22})$alkynyl, aryl, heteroaryl, alkoxy, aryloxy, benzyl, phenyl, carbonyl, hydrogen, hydroxyl, acetyl, hydroxyalkyl, aminoalkyl, amide, carbamate, halogen, $CF_3$, $CCl_3$, sulfonic acid and phosphate;

and pharmaceutically acceptable salts thereof;

subject to at least one proviso selected from:
1) $R_8$ is hydroxyl;
2) at least one W is N;
3) at least one of $R_1$-$R_{10}$ is selected from L, M and P;
4) at least one of $R_1$-$R_{10}$ is selected from K;
5) $R_8$ is K;
6) one of $R_1$-$R_{10}$ is a monoester;
7) one of $R_1$-$R_{10}$ is a dicarboxylic acid;
8) one of $R_1$-$R_{10}$ is succinic acid;
9) $R_8$ and $R_3$, are each hydroxyl;
10) $R_8$ is selected from J; and
11) $R_8$ and $R_3$ are each selected from J.

94. A method for increasing expression of ApoA-I in a mammal comprising administering a therapeutically effective amount of a compound of Formula III:

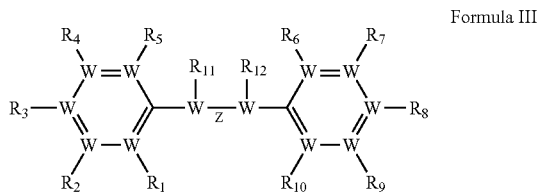

Formula III wherein:
$R_1$, $R_2$, $R_3$, $R_4$, $R_5$, $R_6$, $R_7$, $R_9$, $R_{10}$, $R_{11}$, and $R_{12}$ are each independently selected from $(C_1-C_{22})$alkyl, $(C_2-C_{22})$alkenyl, aryl, heteroaryl, hydrogen, hydroxyl, acetyl, hydroxyalkyl, aminoalkyl, bromide, iodide, methoxy, ethoxy, fluoride, chloride, $CF_3$, $CCl_3$, phosphate, O-sulfate, O-glucoronidate, K, D, E, F and G;

$R_8$ is selected from hydroxyl and K;

each W is independently selected from C and N;

Z is selected from a single bond, a double bond, and a triple bond, provided that when Z is a triple bond, $R_{11}$ and $R_{12}$ are not present;

wherein:
K is

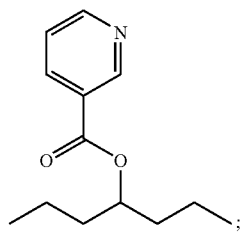

D is

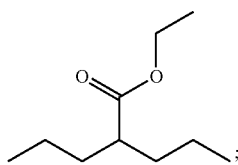

E is selected from

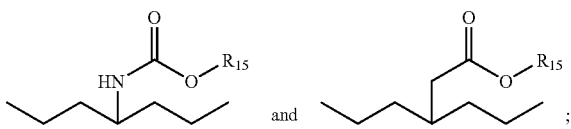

F is selected from

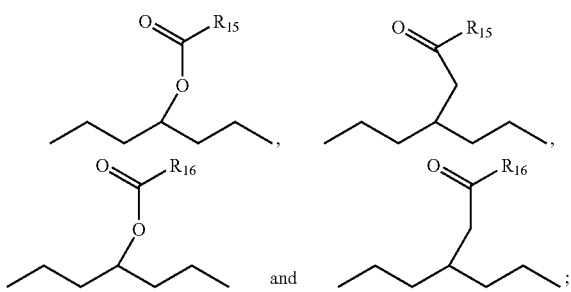

G is

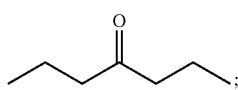

$R_{15}$ is selected from pyridine, pyridazine, pyrimidine, and pyrazine;

$R_{16}$ is selected from $(C_1-C_{22})$alkyl, $(C_2-C_{22})$alkenyl, aryl and heteroaryl;

and pharmaceutically acceptable salts thereof;

subject to at least one proviso selected from:
1) at least one W is N;
2) at least one of $R_{1-7}$ and $R_{9-12}$ is selected from D, E and F; and
3) at least one of $R_{1-7}$ and $R_{9-12}$ is selected from K.

95. The method of embodiment 94, wherein $R_8$ is hydroxyl and at least one of $R_{1-7}$ and $R_{9-12}$ is selected from K.

96. The method of embodiment 95, subject to at least one proviso selected from
1) at least one W is N; and
2) at least one of $R_{1-7}$ and $R_{9-12}$ is selected from D, E and F.

97. The method of embodiment 94, wherein at least one W is N, at least one of $R_{1-7}$ and $R_{9-12}$ is selected from D, E, F, and K.

98. The method of embodiment 94, wherein $R_8$ is hydroxyl and at least one W is N.

99. The method of embodiment 98, wherein at least one of $R_{1-7}$ and $R_{9-12}$ is selected from D, E, F, and K.

100. The method of embodiment 94, wherein at least one W is N; and
if $R_8$ is hydroxyl, then at least one of $R_{1-7}$ and $R_{9-12}$ is K.

101. The method of embodiment 94, wherein E is:

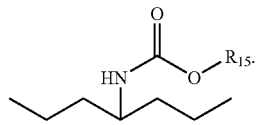

102. The method of embodiment 94, wherein E is:

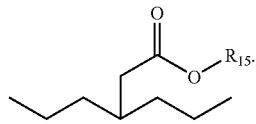

103. The method of embodiment 94, wherein F is selected from:

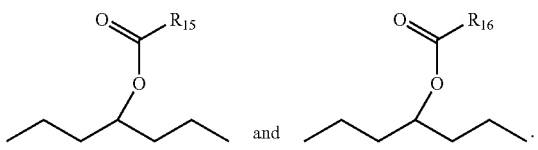

104. The method of embodiment 94, wherein F is selected from:

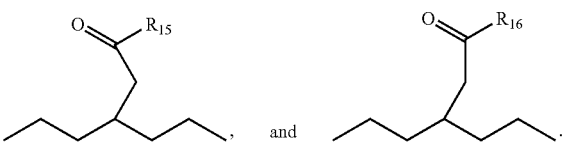

105. The method of embodiment 94, wherein Z is a single bond.

106. The method of embodiment 94, wherein Z is a double bond.

107. The method of embodiment 94, wherein Z is a triple bond.

108. The method of embodiment 94, wherein Formula III has the structure:

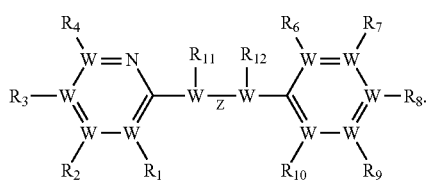

109. A method for increasing expression of ApoA-I in a mammal comprising administering a therapeutically effective amount of a compound selected from Formulae IIIA and IIIB:

Formula IIIA

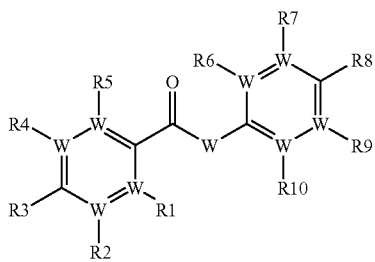

Formula IIIB

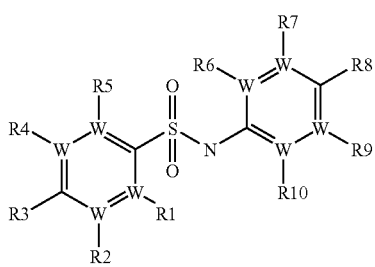

wherein:
R$_1$, R$_2$, R$_3$, R$_4$, R$_5$, R$_6$, R$_7$, R$_9$, and R$_{10}$ are each independently selected from (C$_1$-C$_{22}$)alkyl, (C$_2$-C$_{22}$)alkenyl, aryl, heteroaryl, hydrogen, hydroxyl, acetyl, hydroxyalkyl, aminoalkyl, bromide, iodide, methoxy, ethoxy, fluoride, chloride, CF$_3$, CCl$_3$, phosphate, O-sulfate, O-glucoronidate, K, D, E, F and G;
R$_8$ is selected from hydroxyl and K;
each W is independently selected from C and N;
wherein:
K is

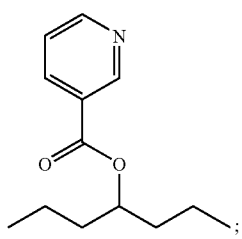

D is

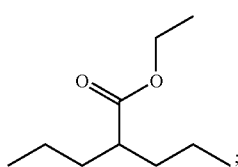

E is selected from and

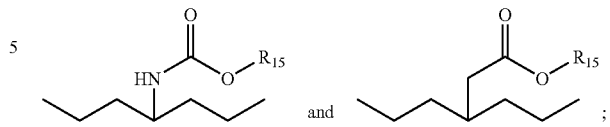

F is selected from and

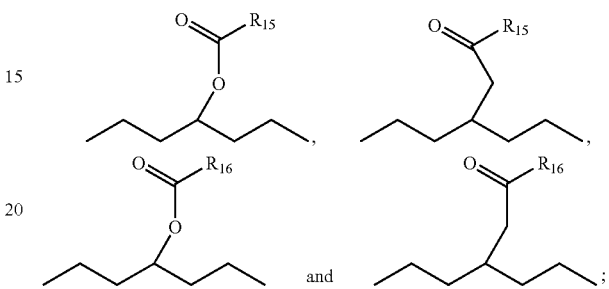

G is

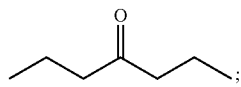

R$_{15}$ is selected from pyridine, pyridazine, pyrimidine, and pyrazine;
R$_{16}$ is selected from (C$_1$-C$_{22}$)alkyl, (C$_2$-C$_{22}$)alkenyl, aryl and heteroaryl;
and pharmaceutically acceptable salts thereof;
subject to at least one proviso selected from:
1) at least one W is N;
2) at least one of R$_{1-7}$ and R$_{9-12}$ is selected from D, E and F; and
3) at least one of R$_{1-7}$ and R$_{9-12}$ is selected from K.

110. A method for increasing expression of ApoA-I in a mammal comprising administering a therapeutically effective amount of a compound of Formula III:

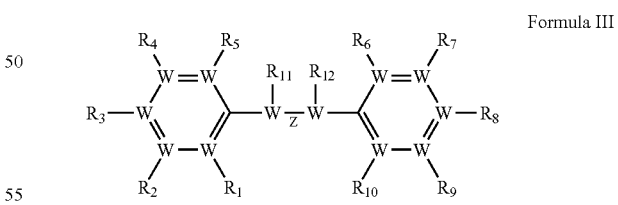

Formula III wherein
R$_1$, R$_2$, R$_4$, R$_5$, R$_6$, R$_7$, R$_9$, R$_{10}$, R$_{11}$, and R$_{12}$ are each independently selected from (C$_1$-C$_{22}$)alkyl, (C$_2$-C$_{22}$) alkenyl, aryl, heteroaryl, hydrogen, hydroxyl, acetyl, hydroxyalkyl, aminoalkyl, bromide, iodide, methoxy, ethoxy, fluoride, chloride, CF$_3$, CCl$_3$, phosphate, O-sulfate, and O-glucoronidate;
R$_3$ and R$_8$ are hydroxyl;
each W is independently selected from C and N; wherein at least one W is N; and Z is selected from a single bond, a double bond, and a triple bond, provided that when Z is a triple bond, $R_{11}$ and $R_{12}$ are not present.

111. The method of embodiment 110, wherein Z is a single bond.
112. The method of embodiment 110, wherein Z is a double bond.
113. The method of embodiment 110, wherein Z is a triple bond.
114. The method of embodiment 110, wherein at least one of $R_1$, $R_2$, $R_4$, $R_5$, $R_6$, $R_7$, $R_9$, $R_{10}$, $R_{11}$, and $R_{12}$ is:

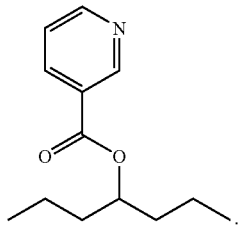

115. The method of embodiment 114, wherein Z is a single bond.
116. The method of embodiment 114, wherein Z is a double bond.
117. The method of embodiment 114, wherein Z is a triple bond.
118. A method for increasing expression of ApoA-I in a mammal comprising administering a therapeutically effective amount of a compound of Formula III:

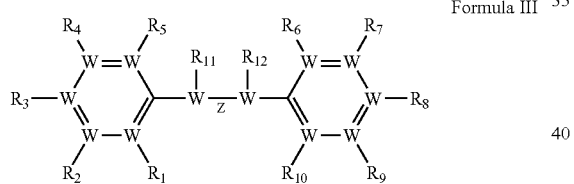

Formula III wherein:
$R_1$, $R_2$, $R_4$, $R_5$, $R_6$, $R_7$, $R_9$, $R_{10}$, $R_{11}$, and $R_{12}$ are each independently selected from $(C_1-C_{22})$alkyl, $(C_2-C_{22})$alkenyl, aryl, heteroaryl, hydrogen, hydroxyl, acetyl, hydroxyalkyl, aminoalkyl, bromide, iodide, methoxy, ethoxy, fluoride, chloride, $CF_3$, $CCl_3$, phosphate, O-sulfate, and O-glucoronidate;
$R_3$ is hydroxyl;
$R_8$ is

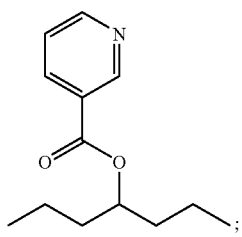

;

each W is independently selected from C and N, wherein at least one W is N; and

Z is selected from a single bond, a double bond, and a triple bond, provided that when Z is a triple bond, $R_{11}$ and $R_{12}$ are not present.

119. The method of embodiment 118, wherein Z is a single bond.
120. The method of embodiment 118, wherein Z is a double bond.
121. The method of embodiment 118, wherein Z is a triple bond.
122. The method of embodiment 110, wherein Formula III has the structure:

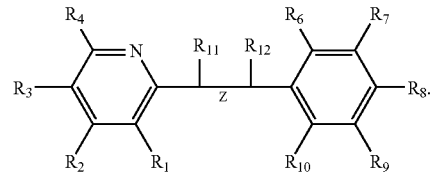

123. The method of embodiment 122, wherein Z is a single bond.
124. The method of embodiment 122, wherein Z is a double bond.
125. The method of embodiment 122, wherein Z is a triple bond.
126. The method of embodiment 114, wherein Formula III has the structure:

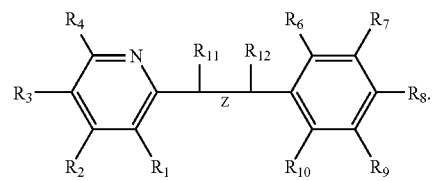

127. The method of embodiment 126, wherein Z is a single bond.
128. The method of embodiment 126, wherein Z is a double bond.
129. The method of embodiment 126, wherein Z is a triple bond.
130. The method of embodiment 118, wherein Formula III has the structure:

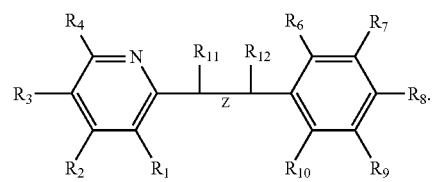

131. The method of embodiment 130, wherein Z is a single bond.
132. The method of embodiment 130, wherein Z is a double bond.
133. The method of embodiment 130, wherein Z is a triple bond.
134. A method of treating or preventing cardiovascular, cholesterol or lipid related disorders comprising administering a therapeutically effective amount of a compound of Formula I:

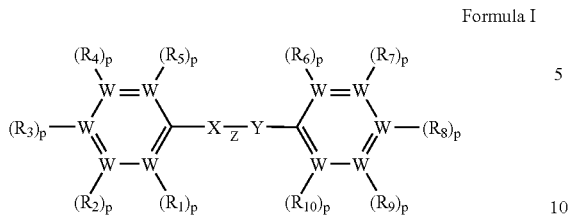

Formula I wherein:
X is selected from C, $CR_{11}$, $CR_{11}R_{13}$, CO, CS, O, S, SO, $SO_2$, N and $NR_{11}$, wherein $R_{11}$ may be the same or different than $R_{13}$;
Y is selected from C, $CR_{12}$, $CR_{12}R_{14}$, CO, CS, O, S, SO, $SO_2$, N and $NR_{12}$, wherein $R_{12}$ may be the same or different than $R_{14}$;
$R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ are each independently selected from alkoxy, aryloxy, alkyl, alkenyl, alkynyl, amide, amino, aryl, arylalkyl, carbamate, carboxy, cyano, cycloalkyl, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone, or
two adjacent substituents selected from $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ are connected in a 5 or 6-membered ring to form a bicyclic aryl or bicyclic heteroaryl;
each W is independently selected from C and N, wherein if W is N, then p is 0 and if W is C, then p is 1;
Z is selected from a single bond, a double bond and a triple bond;
and pharmaceutically acceptable salts and hydrates thereof;
wherein if $R_3$ and $R_8$ are each hydroxyl, then at least one of $R_{11}$ and $R_{12}$ is not alkyl;
wherein if Z is a double bond, then $R_2$ and $R_4$ and $R_8$ are not simultaneously hydroxyl; and
wherein if Formula 1 has the structure:

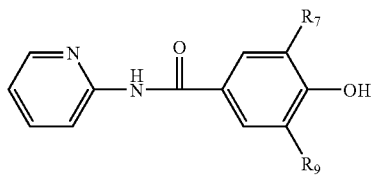

then at least one of $R_7$ and $R_9$ is not alkyl.
135. The method of embodiment 134, wherein the cardiovascular, cholesterol or lipid related disorder is selected from
acute coronary syndrome, angina pectoris, arteriosclerosis, atherosclerosis, carotid atherosclerosis, cerebrovascular disease, cerebral infarction, congestive heart failure, congenital heart disease, coronary heart disease, coronary artery disease, coronary plaque stabilization, dyslipidemias, dyslipoproteinemias, endothelium dysfunctions, familial hypercholesterolemia, familial combined hyperlipidemia, hypertension, hyperlipidemia, intermittent claudication, ischemia, ischemia reperfusion injury; ischemic heart diseases, multi-infarct dementia, myocardial infarction, peripheral vascular disease, restenosis, renal artery atherosclerosis, rheumatic heart disease, stroke, thrombotic disorder, transitory ischemic attacks, and lipoprotein abnormalities associated with Alzheimer's disease, obesity, diabetes mellitus, syndrome X and impotence.
136. The method of embodiment 135, wherein treating or preventing a cholesterol disorder comprises decreasing blood cholesterol levels.
137. The method of embodiment 135, wherein treating or preventing a cholesterol disorder comprises increasing blood ApoA-I levels.
138. The method of embodiment 135, wherein the therapeutically effective amount of the compound of Formula I is administered with a pharmaceutically acceptable carrier in a pharmaceutically acceptable composition.
139. The method of embodiment 135, wherein the therapeutically effective amount of the compound of Formula I is sufficient to establish a concentration ranging from about 0.001 μM to about 100 μM in the mammal.
140. The method of embodiment 136, wherein the concentration ranges from about 1 μM to about 20 μM.
141. A method for increasing expression of ApoA-I in a mammal comprising administering a therapeutically effective amount of a compound of Formula IV:

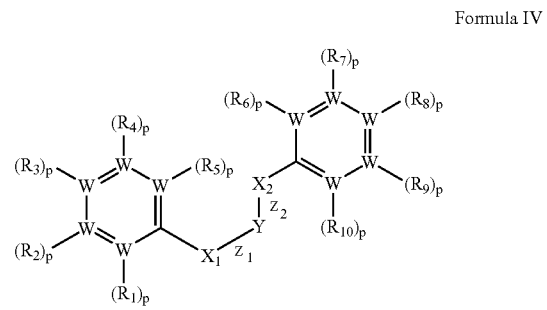

Formula IV wherein:
$X_1$ is selected from C, $CR_{11}$, $CR_{11}R_{13}$, CO, CS, O, S, SO, $SO_2$, N and $NR_{11}$, wherein $R_{11}$ may be the same or different than $R_{13}$;
$X_2$ is selected from C, $CR_{17}$, $CR_{17}R_{18}$, CO, CS, O, S, SO, $SO_2$, N and $NR_{17}$, wherein $R_{17}$ may be the same or different than $R_{18}$;
Y is selected from C, $CR_{12}$, $CR_{12}R_{14}$, CO, CS, S, SO, $SO_2$, N and $NR_{12}$, wherein $R_{12}$ may be the same or different than $R_{14}$;
$R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{17}$ and $R_{18}$ are each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone, or
two adjacent substituents selected from $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{17}$ and $R_{18}$ are connected in a 5 or 6-membered ring to form a bicyclic aryl or bicyclic heteroaryl;
each W is independently selected from C and N, wherein if W is N, then p is 0 and if W is C, then p is 1;
$Z_1$ and $Z_2$ are each independently selected from a single bond, a double bond, and a triple bond;

142. The method of embodiment 6, wherein $R_8$ is hydroxyl, and $R_7$ and $R_9$ are independently selected from arylalkyl, carboxy, cyano, cycloalkyl, ester, formyl, halogen, haloalkyl, heteroaryl, heterocyclyl, hydrogen, hydroxyl, hydroxyalkyl, hydroxyaryl, ketone, perfluoroalkyl, perfluorocyclolkyl, perfluoralkoxy, trichloromethyl, O-sulfate, and O-glucoronidate, subject to the proviso that $R_7$ and $R_9$ are not both simultaneously hydrogen.

143. The method of embodiment 6, wherein at least one W is N.

144. The method of embodiment 142, wherein at least one W is N.

145. The method of embodiment 6, wherein at least one of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{17}$ and $R_{18}$ is selected from O-sulfate and O-glucoronidate.

146. The method of embodiment 6, wherein at least one of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{17}$ and $R_{18}$ is selected from succinate, D-argininate, L-argininate, L-lysinate and D-lysinate.

147. The method of embodiment 6, wherein at least one of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{17}$ and $R_{18}$ is selected from amide, amino, carbamate, carboxy, ester, ether, formyl, and ketone.

148. The method of embodiment 147, wherein at least one of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and $R_{17}$ is a nicotinate ester.

149. The method of embodiment 6, wherein $Z_1$ is a double bond, X is selected from C, $CR_{11}$ and N, and Y is selected from C, $CR_{17}$, and N.

150. The method of embodiment 149, wherein $R_8$ is hydroxyl, and $R_7$ and $R_9$ are independently selected from arylalkyl, carboxy, cyano, cycloalkyl, ester, formyl, halogen, haloalkyl, heteroaryl, heterocyclyl, hydrogen, hydroxyl, hydroxyalkyl, hydroxyaryl, ketone, perfluoroalkyl, perfluorocyclolkyl, perfluoralkoxy, trichloromethyl, O-sulfate, and O-glucoronidate, subject to the proviso that $R_7$ and $R_9$ are not both simultaneously hydrogen.

151. The method of embodiment 149, wherein at least one W is N.

152. The method of embodiment 150, wherein at least one W is N.

153. The method of embodiment 6, wherein $Z_2$ is a double bond, X is selected from C, $CR_{11}$ and N, and Y is selected from C, $CR_{17}$, and N.

154. The method of embodiment 153, wherein $R_8$ is hydroxyl, and $R_7$ and $R_9$ are independently selected from arylalkyl, carboxy, cyano, cycloalkyl, ester, formyl, halogen, haloalkyl, heteroaryl, heterocyclyl, hydrogen, hydroxyl, hydroxyalkyl, hydroxyaryl, ketone, perfluoroalkyl, perfluorocyclolkyl, perfluoralkoxy, trichloromethyl, O-sulfate, and O-glucoronidate, subject to the proviso that $R_7$ and $R_9$ are not both simultaneously hydrogen.

155. The method of embodiment 153, wherein at least one W is N.

156. The method of embodiment 154, wherein at least one W is N.

157. The method of embodiment 153, wherein $Z_1$ is a single bond and $X_1$ is CO.

158. The method of embodiment 157, wherein $R_8$ is hydroxyl, and $R_7$ and $R_9$ are independently selected from arylalkyl, carboxy, cyano, cycloalkyl, ester, formyl, halogen, haloalkyl, heteroaryl, heterocyclyl, hydrogen, hydroxyl, hydroxyalkyl, hydroxyaryl, ketone, perfluoroalkyl, perfluorocyclolkyl, perfluoralkoxy, trichloromethyl, O-sulfate, and O-glucoronidate, subject to the proviso that $R_7$ and $R_9$ are not both simultaneously hydrogen.

159. The method of embodiment 157, wherein at least one W is N.

160. The method of embodiment 158, wherein at least one W is N.

161. The method of embodiment 157, wherein Y is $CR_{14}$.

162. The method of embodiment 161, wherein $R_8$ is hydroxyl, and $R_7$ and $R_9$ are independently selected from arylalkyl, carboxy, cyano, cycloalkyl, ester, formyl, halogen, haloalkyl, heteroaryl, heterocyclyl, hydrogen, hydroxyl, hydroxyalkyl, hydroxyaryl, ketone, perfluoroalkyl, perfluorocyclolkyl, perfluoralkoxy, trichloromethyl, O-sulfate, and O-glucoronidate, subject to the proviso that $R_7$ and $R_9$ are not both simultaneously hydrogen.

163. The method of embodiment 161, wherein at least one W is N.

164. The method of embodiment 162, wherein at least one W is N.

165. The method of embodiment 149, wherein $Z_2$ is a double bond.

166. The method of embodiment 165, wherein at least one W is N.

167. The method of embodiment 6, wherein Formula IV has the structure:

168. The method of embodiment 167, wherein $R_8$ is hydroxyl, and $R_7$ and $R_9$ are independently selected from arylalkyl, carboxy, cyano, cycloalkyl, ester, formyl, halogen, haloalkyl, heteroaryl, heterocyclyl, hydrogen, hydroxyl, hydroxyalkyl, hydroxyaryl, ketone, perfluoroalkyl, perfluorocyclolkyl, perfluoralkoxy, trichloromethyl, O-sulfate, and O-glucoronidate, subject to the proviso that $R_7$ and $R_9$ are not both simultaneously hydrogen.

169. The method of embodiment 167, wherein at least one W is N.

170. The method of embodiment 168, wherein at least one W is N.

171. The method of embodiment 167, wherein $Z_1$ is a single bond, $Z_2$ is a double bond, and $X_1$ is CO.

172. The method of embodiment 171, wherein $R_8$ is hydroxyl, and $R_7$ and $R_9$ are independently selected from arylalkyl, carboxy, cyano, cycloalkyl, ester, formyl, halogen, haloalkyl, heteroaryl, heterocyclyl, hydrogen, hydroxyl, hydroxyalkyl, hydroxyaryl, ketone, perfluoroalkyl, perfluorocyclolkyl, perfluoralkoxy, trichloromethyl, O-sulfate, and O-glucoronidate, subject to the proviso that $R_7$ and $R_9$ are not both simultaneously hydrogen.

173. The method of embodiment 171, wherein at least one W is N.

174. The method of embodiment 172, wherein at least one W is N.

175. The method of embodiment 171, wherein Y is $CR_{14}$.

176. The method of embodiment 175, wherein $R_8$ is hydroxyl, and $R_7$ and $R_9$ are independently selected from arylalkyl, carboxy, cyano, cycloalkyl, ester, formyl, halogen, haloalkyl, heteroaryl, heterocyclyl, hydrogen, hydroxyl, hydroxyalkyl, hydroxyaryl, ketone, perfluoroalkyl, perfluorocyclolkyl, perfluoralkoxy, trichloromethyl, O-sulfate, and O-glucoronidate, subject to the proviso that $R_7$ and $R_9$ are not both simultaneously hydrogen.

177. The method of embodiment 175, wherein at least one W is N.

178. The method of embodiment 176, wherein at least one W is N.

179. The method of embodiment 6, wherein the therapeutically effective amount of the compound of Formula I is sufficient to establish a concentration ranging from about 0.001 µM to about 100 µM in the mammal.

180. The method of embodiment 180, wherein the concentration ranges from about 1 µM to about 20 µM.

181. The method of embodiment 6, wherein the therapeutically effective amount of the compound of Formula IV is administered with a pharmaceutically acceptable carrier in a pharmaceutically acceptable composition.

182. A method for increasing expression of ApoA-I in a mammal comprising administering a therapeutically effective amount of a compound of Formula IV:

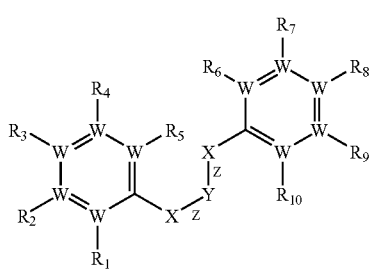

Formula V wherein:

X is selected from CH, $CH_2$, $CR_{11}$, $CR_{13}$, $CHR_{11}$, $CHR_{13}$, $CR_{11}R_{13}$, CO, CS, O, S, SO, $SO_2$, NH and $NR_{11}$, wherein $R_{11}$ may be the same or different than $R_{13}$;

Y is selected from CH, $CH_2$, $CR_{12}$, $CR_{14}$, $CHR_{12}$, $CHR_{14}$, $CR_{12}R_{14}$, CO, CS, O, S, SO, $SO_2$, NH and $NR_{12}$, wherein $R_{12}$ may be the same or different than $R_{14}$;

$R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ are each independently selected from $(C_1-C_{22})$alkyl, $(C_2-C_{22})$alkenyl, $(C_1-C_{22})$alkynyl, aryl, heteroaryl, alkoxy, aryloxy, benzyl, phenyl, carbonyl, thioketone, hydrogen, hydroxyl, acetyl, hydroxyalkyl, aminoalkyl, amide, carbamate, halogen, $CF_3$, $CCl_3$, sulfonic acid, phosphate, O-sulfate, O-glucoronidate, monoester, dicarboxylic acid, J, K, L, M, P and Q;

each W is independently selected from C and N;

Z is selected from a single bond, a double bond, and a triple bond;

J is selected from

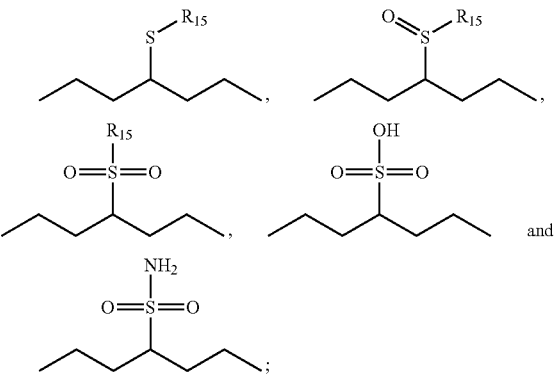

K is

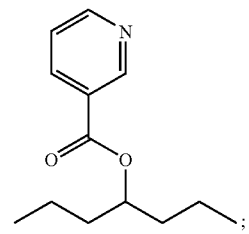

L is selected from

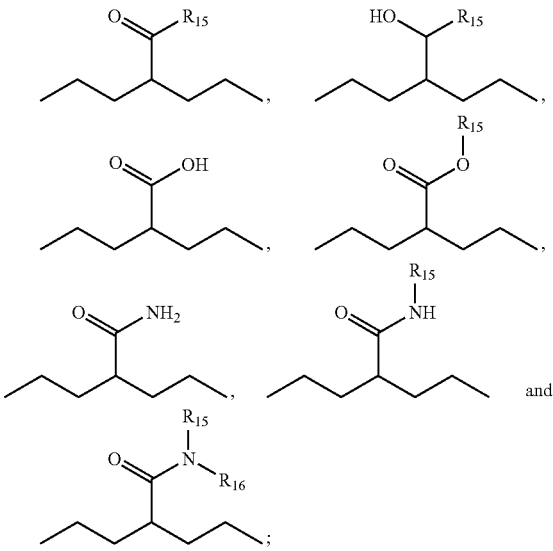

M is selected from

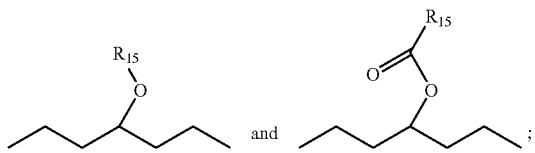
and ;

P is selected from

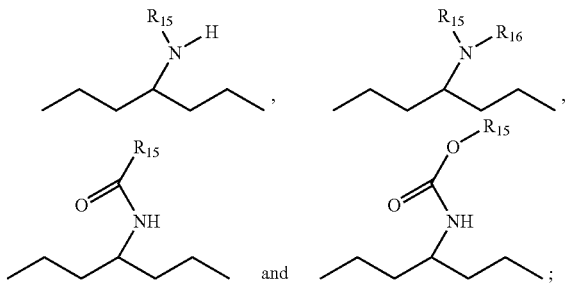
and ;

Q is selected from

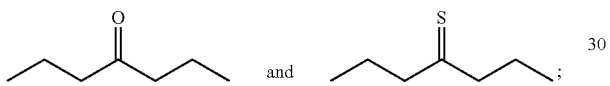
and ;

$R_{15}$ and $R_{16}$ are each independently selected from $(C_1-C_{22})$ alkyl, $(C_2-C_{22})$alkenyl, $(C_1-C_{22})$alkynyl, aryl, heteroaryl, alkoxy, aryloxy, benzyl, phenyl, carbonyl, hydrogen, hydroxyl, acetyl, hydroxyalkyl, aminoalkyl, amide, carbamate, halogen, $CF_3$, $CCl_3$, sulfonic acid and phosphate;

and pharmaceutically acceptable salts thereof;
subject to at least one proviso selected from:
 a. $R_8$ is hydroxyl;
 b. at least one W is N;
 c. at least one of $R_1-R_{12}$ is selected from L, M and P;
 d. at least one of $R_1-R_{12}$ is selected from K;
 e. $R_8$ is K;
 f. one of $R_1-R_{12}$ is a monoester;
 g. one of $R_1-R_{12}$ is a dicarboxylic acid;
 h. one of $R_1-R_{12}$ is succinic acid;
 i. $R_8$ and $R_3$ are each hydroxyl;
 j. $R_8$ is selected from J; and
 k. $R_8$ and $R_3$ are each selected from J.

183. The method of embodiment 182, wherein the proviso is selected from provisos 1, 2, 4, 5, and 9.
184. The method of embodiment 182, wherein $R_8$ is hydroxyl and at least one W is N.
185. The method of embodiment 182, wherein $R_8$ is hydroxyl and at least one of $R_1-R_7$ and $R_9-R_{12}$ is K.
186. The method of embodiment 182, wherein $R_8$ is hydroxyl and at least one of $R_1-R_7$ and $R_9-R_{12}$ is selected from L, M and P.
187. The method of embodiment 182, wherein Z is a single bond.
188. The method of embodiment 182, wherein Formula V is selected from Formulae VA-VE:

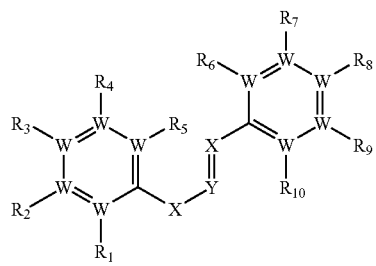
Formula VA

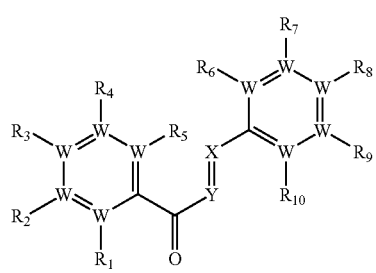
Formula VB

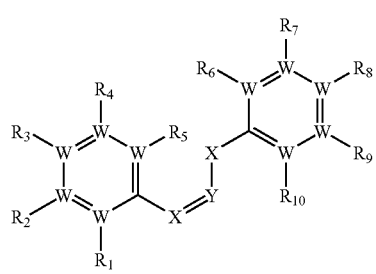
Formula VC

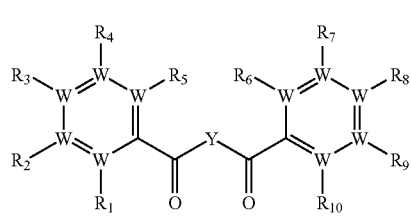
Formula VD

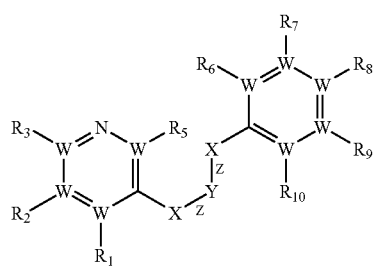
Formula VE

189. A method for increasing expression of ApoA-I in a mammal comprising administering a therapeutically effective amount of a compound of Formula VI:

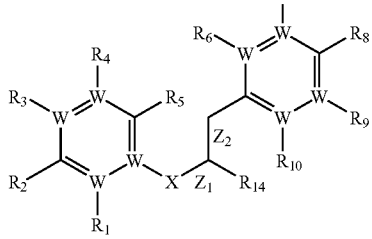

Formula VI wherein:
$R_1$, $R_2$, $R_3$, $R_4$, $R_5$, $R_6$, $R_7$, $R_9$, $R_{10}$, and $R_{14}$ are each independently selected from $(C_1-C_{22})$alkyl, $(C_2-C_{22})$alkenyl, aryl, heteroaryl, hydrogen, hydroxyl, acetyl, hydroxyalkyl, aminoalkyl, bromide, iodide, methoxy, ethoxy, fluoride, chloride, $CF_3$, $CCl_3$, phosphate, O-sulfate, O-glucoronidate, K, D, E, F and G;

$R_8$ is selected from hydroxyl or K;

each W is independently selected from C and N;

X is selected from O, C, N, S, $CR_{13}$ and $NR_{13}$;

$Z_1$ and $Z_2$ are each independently is selected from a single bond and a double bond;

$R_{13}$ is selected from D, E, F and G;

wherein:

K is

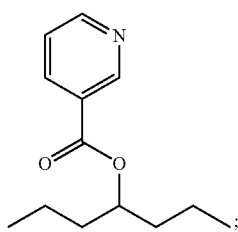

D is

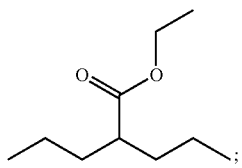

E is selected from

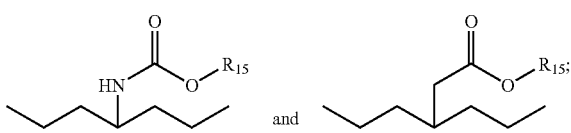

F is selected from

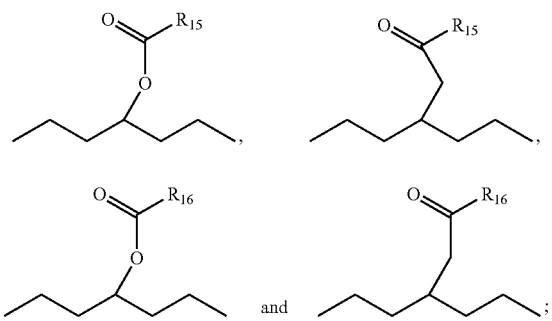

G is

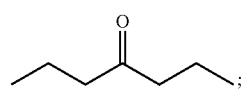

$R_{15}$ is selected from pyridine, pyridazine, pyrimidine, and pyrazine;

$R_{16}$ is selected from $(C_1-C_{22})$alkyl, $(C_2-C_{22})$alkenyl, aryl and heteroaryl;

and pharmaceutically acceptable salts thereof;

subject to at least one proviso selected from:
1) at least one W is N;
2) at least one of $R_{1-7}$ and $R_{9-12}$ is selected from D, E and F; and
3) at least one of $R_{1-7}$ and $R_{9-12}$ is selected from K.

190. The method of embodiment 189, wherein $R_8$ is hydroxyl and at least one of $R_{1-7}$ and $R_{9-10}$ is selected from K.

191. The method of embodiment 190, subject to at least one proviso selected from:
1) at least one W is N; and
2) at least one of $R_{1-7}$ and $R_{9-10}$ is selected from D, E and F.

192. The method of embodiment 189, wherein at least one W is N, at least one of $R_{1-6}$ and $R_{8-10}$ is selected from D, E and F, and at least one of $R_{1-7}$ and $R_{9-10}$ is selected from K.

193. The method of embodiment 189, wherein X is O, and $Z_1$ and $Z_2$ are each single bonds.

194. The method of embodiment 189, wherein X is O, $Z_1$ is a single bond and $Z_2$ is a double bond.

195. The method of embodiment 189, wherein X is N, $Z_1$ is a double bond and $Z_2$ is a single bond.

196. The method of embodiment 189, wherein X is S, and $Z_1$ and $Z_2$ are each single bonds.

197. The method of embodiment 189, wherein X is S, $Z_1$ is a double bond and $Z_2$ is a single bond.

198. The method of embodiment 189, wherein Formula VI is selected from Formulae VIA to VIJ:

-continued
Formula VIA
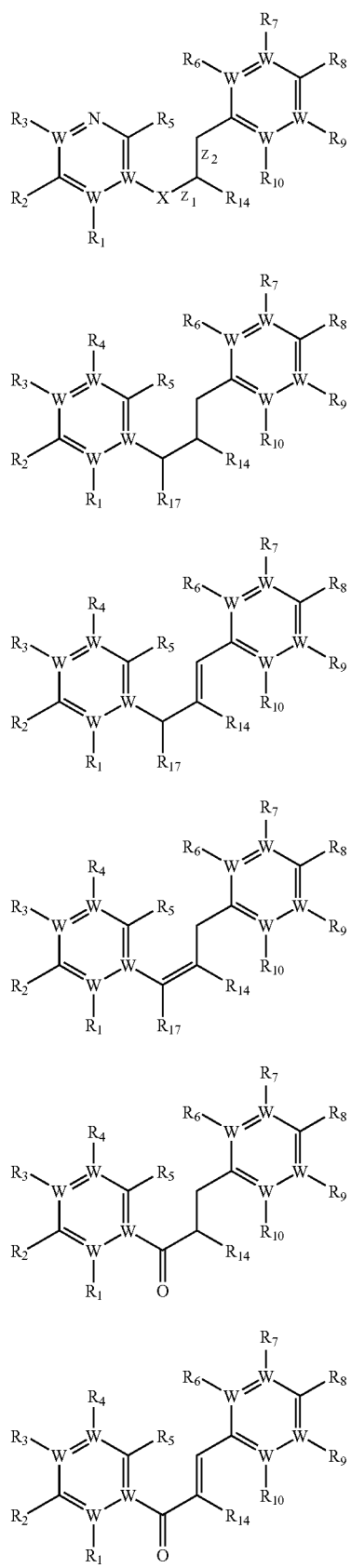
Formula VIB
Formula VIC
Formula VID
Formula VIE
Formula VIF
Formula VIG
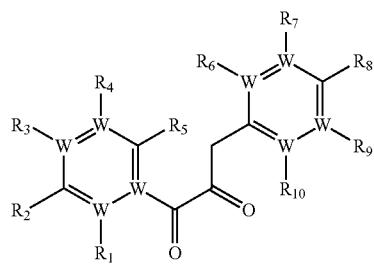
Formula VIH
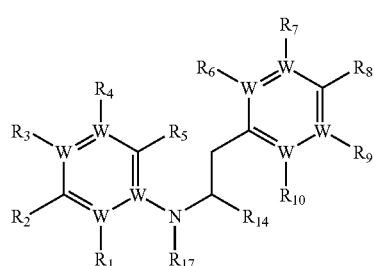
Formula VIJ
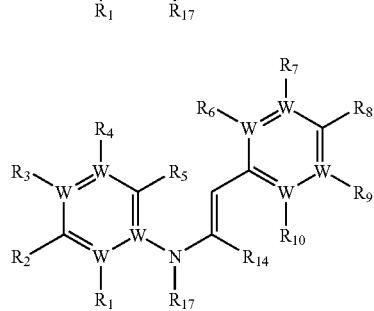
199. A method for increasing expression of ApoA-I in a mammal comprising administering a therapeutically effective amount of a compound selected from Formulae VIK-VIR:
Formula VIK
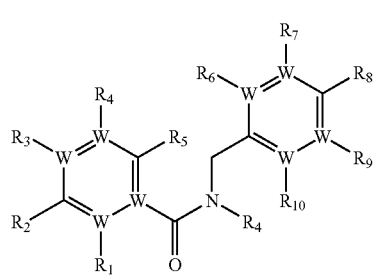
Formula VIL
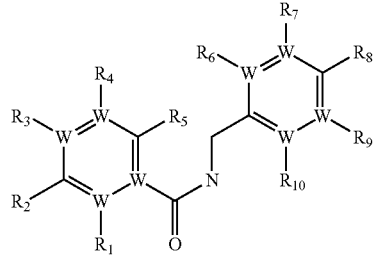

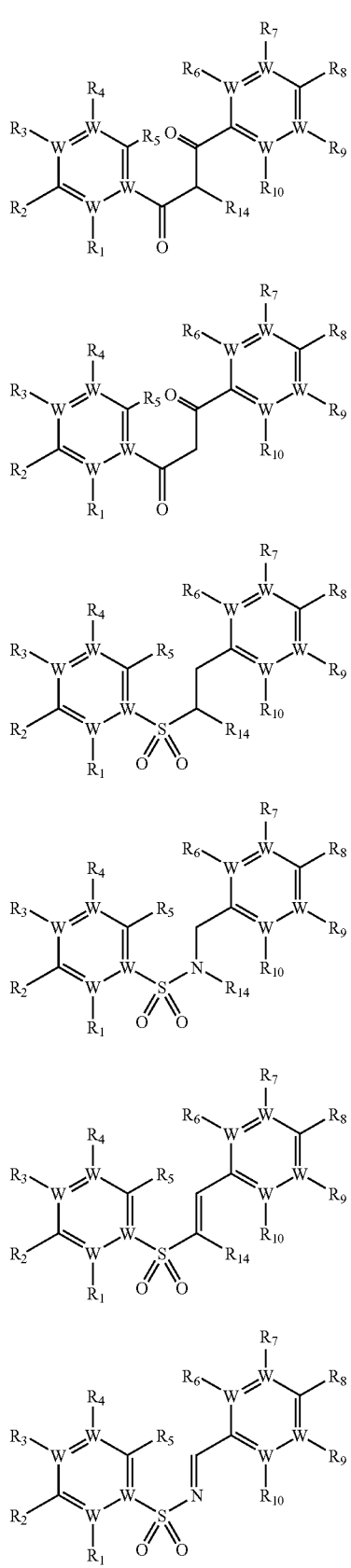

Formula VIM

Formula VIN

Formula VIO

Formula VIP

Formula VIQ

Formula VIR wherein:

$R_1$, $R_2$, $R_3$, $R_4$, $R_5$, $R_6$, $R_7$, $R_9$, $R_{10}$, $R_{14}$, and $R_{17}$ are each independently selected from ($C_1$-$C_{22}$)alkyl, ($C_2$-$C_{22}$) alkenyl, aryl, heteroaryl, hydrogen, hydroxyl, acetyl, hydroxyalkyl, aminoalkyl, bromide, iodide, methoxy, ethoxy, fluoride, chloride, $CF_3$, $CCl_3$, phosphate, O-sulfate, O-glucoronidate, K, D, E, F and G;

$R_7$ is selected from hydroxyl or K;

each W is independently selected from C and N;

X is selected from O, C, N, S, $CR_{13}$ and $NR_{13}$;

$R_{13}$ is selected from D, E, F and G;

wherein:

K is

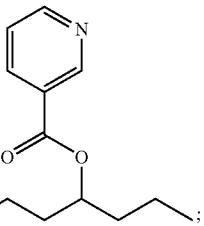

D is

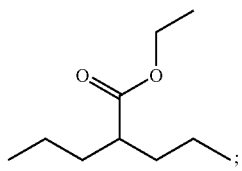

E is selected from

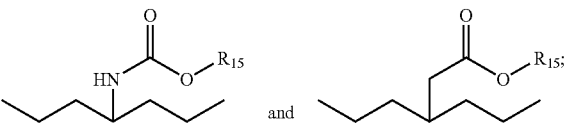

F is selected from

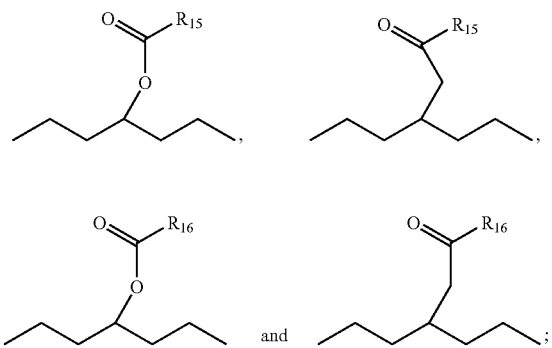

G is

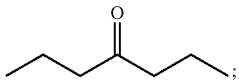

$R_{15}$ is selected from pyridine, pyridazine, pyrimidine, and pyrazine;

$R_{16}$ is selected from $(C_1\text{-}C_{22})$alkyl, $(C_2\text{-}C_{22})$alkenyl, aryl and heteroaryl;

and pharmaceutically acceptable salts thereof;

subject to at least one proviso selected from:
1) at least one W is N;
2) at least one of $R_{1-7}$ and $R_{9-12}$ is selected from D, E and F; and
3) at least one of $R_{1-7}$ and $R_{9-12}$ is selected from K.

200. A method of treating or preventing cardiovascular, cholesterol or lipid related disorders comprising administering a therapeutically effective amount of a compound of Formula IV:

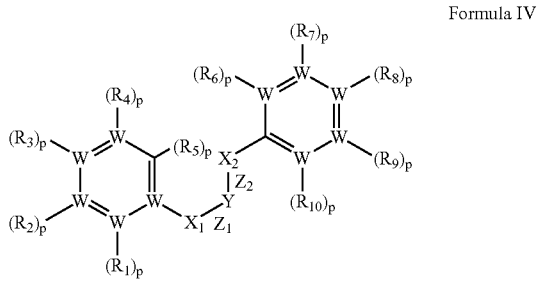

Formula IV wherein:

$X_1$ is selected from C, $CR_{11}$, $CR_{11}R_{13}$, CO, CS, O, S, SO, $SO_2$, N and $NR_{11}$, wherein $R_{11}$ may be the same or different than $R_{13}$;

$X_2$ is selected from C, $CR_{17}$, $CR_{17}R_{18}$, CO, CS, O, S, SO, $SO_2$, N and $NR_{17}$, wherein $R_{17}$ may be the same or different than $R_{18}$;

Y is selected from C, $CR_{12}$, $CR_{12}R_{14}$, CO, CS, S, SO, $SO_2$, N and $NR_{12}$, wherein $R_{12}$ may be the same or different than $R_{14}$;

$R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{17}$ and $R_{18}$ are each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone, or two adjacent substituents selected from $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{17}$ and $R_{18}$ are connected in a 5 or 6-membered ring to form a bicyclic aryl or bicyclic heteroaryl;

each W is independently selected from C and N, wherein if W is N, then p is 0 and if W is C, then p is 1;

$Z_1$ and $Z_2$ are each independently selected from a single bond, a double bond, and a triple bond;

and pharmaceutically acceptable salts and hydrates thereof.

201. The method of embodiment 200, wherein the cardiovascular, cholesterol or lipid related disorder is selected from acute coronary syndrome, angina pectoris, arteriosclerosis, atherosclerosis, carotid atherosclerosis, cerebrovascular disease, cerebral infarction, congestive heart failure, congenital heart disease, coronary heart disease, coronary artery disease, coronary plaque stabilization, dyslipidemias, dyslipoproteinemias, endothelium dysfunctions, familial hypercholeasterolemia, familial combined hyperlipidemia, hypertension, hyperlipidemia, intermittent claudication, ischemia, ischemia reperfusion injury, ischemic heart diseases, multi-infarct dementia, myocardial infarction, peripheral vascular disease, restenosis, renal artery atherosclerosis, rheumatic heart disease, stroke, thrombotic disorder, transitory ischemic attacks, and lipoprotein abnormalities associated with Alzheimer's disease, obesity, diabetes mellitus, syndrome X and impotence.

202. The method of embodiment 200, wherein treating or preventing a cholesterol disorder comprises decreasing blood cholesterol levels.

203. The method of embodiment 200, wherein treating a or preventing cholesterol disorder comprises increasing blood ApoA-I levels.

204. The method of embodiment 200, wherein the therapeutically effective amount of the compound of Formula IV is administered with a pharmaceutically acceptable carrier in a pharmaceutically acceptable composition.

205. The method of embodiment 200, wherein the therapeutically effective amount of the compound of Formula I is sufficient to establish a concentration ranging from about 0.001 μM to about 100 μM in the mammal.

206. The method of embodiment 205, wherein the concentration ranges from about 1 μM to about 20 μM.

Pharmaceutical Formulations and Methods of Treatment

The present disclosure also provides pharmaceutical compositions comprising compounds as disclosed herein formulated together with one or more pharmaceutically acceptable carriers. These formulations include those suitable for oral, rectal, topical, buccal and parenteral (e.g. subcutaneous, intramuscular, intradermal, or intravenous) administration, although the most suitable form of administration in any given case will depend on the degree and severity of the condition being treated and on the nature of the particular compound being used.

Formulations suitable for oral administration may be presented in discrete units, such as capsules, cachets, lozenges, or tablets, each containing a predetermined amount of the compound as powder or granules; as a solution or a suspension in an aqueous or non-aqueous liquid; or as an oil-in-water or water-in-oil emulsion. As indicated, such formulations may be prepared by any suitable method of pharmacy which includes the step of bringing into association the active compound and the carrier or excipient (which may constitute one or more accessory ingredients). The carrier must be acceptable in the sense of being compatible with the other ingredients of the formulation and must not be deleterious to the recipient. The carrier may be a solid or a liquid, or both, and may be formulated with the compound as a unit-dose formulation, for example, a tablet, which may contain from 0.05% to 95% by weight of the active compound. Other pharmacologically active substances may also be present including other compounds. The formulations of the invention may be prepared by any of the well known techniques of pharmacy consisting essentially of admixing the, components.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. In general, suitable formulations may be prepared by uniformly and intimately admixing the active compound with a liquid or finely divided solid carrier, or both, and then, if necessary, shaping the product. For example, a tablet may be prepared by compressing or molding a powder or granules of the compound, optionally with one or more assessory ingredients. Compressed tablets may be prepared by compressing, in a suitable machine, the compound in a free-flowing form, such as a powder or granules optionally mixed with a binder, lubricant, inert diluent and/or surface active/dispersing agent(s). Molded tablets may be made by molding, in a suitable machine, the powdered compound moistened with an inert liquid diluent.

Formulations suitable for buccal (sub-lingual) administration include lozenges comprising a compound in a flavored base, usually sucrose and acacia or tragacanth, and pastilles comprising the compound in an inert base such as gelatin and glycerin or sucrose and acacia.

Formulations of the present invention suitable for parenteral administration comprise sterile aqueous preparations of the compounds, which are approximately isotonic with the blood of the intended recipient. These preparations are administered intravenously, although administration may also be effected by means of subcutaneous, intramuscular, or intradermal injection. Such preparations may conveniently be prepared by admixing the compound with water and rendering the resulting solution sterile and isotonic with the blood. Injectable compositions according to the invention may contain from 0.1 to 5% w/w of the active compound.

Formulations suitable for rectal administration are presented as unit-dose suppositories. These may be prepared by admixing the compound with one or more conventional solid carriers, for example, cocoa butter, and then shaping the resulting mixture.

Formulations suitable for topical application to the skin may take the form of an ointment, cream, lotion, paste, gel, spray, aerosol, or oil. Carriers and excipients which may be used include Vaseline, lanoline, polyethylene glycols, alcohols, and combinations of two or more thereof. The active compound is generally present at a concentration of from about 0.1% to about 15% w/w of the composition, for example, from about 0.5 to about 2%.

The amount of active compound administered may be dependent on the subject being treated, the subject's weight, the manner of administration and the judgment of the prescribing physician. For example, a dosing schedule may involve the daily or semi-daily administration of the encapsulated compound at a perceived dosage of about 1 µg to about 1000 mg. In another embodiment, intermittent administration, such as on a monthly or yearly basis, of a dose of the encapsulated compound may be employed. Encapsulation facilitates access to the site of action and allows the administration of the active ingredients simultaneously, in theory producing a synergistic effect. In accordance with standard dosing regimens, physicians will readily determine optimum dosages and will be able to readily modify administration to achieve such dosages.

A therapeutically effective amount of a compound or composition disclosed herein can be measured by the therapeutic effectiveness of the compound. Compounds of the invention may be administered in a dose of about 1 µg/kg to about 200 mg/kg daily; such as from about 1 µg/kg to about 150 mg/kg, from about 1 mg/kg to about 200 mg/kg, from about 1 µg/kg to about 100 mg/kg, from about 1 µg/kg to about 1 mg/kg, from about 50 µg/kg to about 200 mg/kg, from about 10 µg/kg to about 1 mg/kg, from about 10 µg/kg to about 100 µg/kg, from about 100 µg to about 10 mg/kg, and from about 500 µg/kg to about 50 mg/kg. The dosages, however, may be varied depending upon the requirements of the patient, the severity of the condition being treated, and the compound being used. In one embodiment, the therapeutically effective amount of a disclosed compound is sufficient to establish a maximal plasma concentration ranging from about 0.001 µM to about 100 µM, e.g., from about 1 µM to about 20 µM. Preliminary doses as, for example, determined according to animal tests, and the scaling of dosages for human administration is performed according to art-accepted practices.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferable.

The therapeutically effective dose can be estimated initially from cell culture assays. A dose may be formulated in animal models to achieve a circulating plasma concentration range that includes the $IC_{50}$ (i.e., the concentration of the therapeutic which achieves a half-maximal inhibition of symptoms) as determined in cell culture assays or animal models. Levels in plasma may be measured, for example, by high performance liquid chromatography. The effects of any particular dosage can be monitored by a suitable bioassay. Examples of dosages are: about $0.1 \times IC_{50}$, about $0.5 \times IC_{50}$, about $1 \times IC_{50}$, about $5 \times IC_{50}$, $10 \times IC_{50}$, about $50 \times IC_{50}$, and about $100 \times IC_{50}$.

Data obtained from the cell culture assays or animal studies can be used in formulating a range of dosage for use in humans. Therapeutically effective dosages achieved in one animal model may be converted for use in another animal, including humans, using conversion factors known in the art (see, e.g., Freireich et al., *Cancer Chemother. Reports* 50(4): 219-244 (1966) and Table 1 for equivalent Surface Area Dosage Factors).

TABLE 1

| | To: | | | | |
| --- | --- | --- | --- | --- | --- |
| From. | Mouse (20 g) | Rat (150 g) | Monkey (3.5 kg) | Dog (8 kg) | Human (60 kg) |
| Mouse | 1 | ½ | ¼ | ⅙ | 1/12 |
| Rat | 2 | 1 | ½ | ¼ | 1/7 |
| Monkey | 4 | 2 | 1 | ⅗ | ⅓ |
| Dog | 6 | 4 | ⅗ | 1 | ½ |
| Human | 12 | 7 | 3 | 2 | 1 |

The dosage of such compounds lies preferably within a range of circulating concentrations that include the $ED_{50}$ with little or no toxicity. The dosage may vary within this range depending upon the dosage form employed and the route of administration utilized. Generally, a therapeutically effective amount may vary with the subject's age, condition, and sex, as well as the severity of the medical condition in the subject. The dosage may be determined by a physician and adjusted, as necessary, to suit observed effects of the treatment.

In one embodiment, a compound as disclosed herein, or a pharmaceutically acceptable salt or hydrate thereof, is administered in combination with another therapeutic agent. The other therapeutic agent can provide additive or synergistic value relative to the administration of a stilbene or chalcone compound alone. The therapeutic agent can be, for example, a statin; a PPAR agonist, e.g., a thiazolidinedione or fibrate; a bile-acid-binding-resin; a niacin; a RXR agonist; an anti-obesity drug; a hormone; a tyrophostine; a sulfonylurea-based drug; a biguanide; an alpha-glucosidase inhibitor; apolipoprotein E; a cardiovascular drug; an HDL-raising drug; an HDL enhancer; or a regulator of the apolipoprotein A-IV and/or apolipoprotein genes.

In one embodiment, a method of treating or preventing cardiovascular, cholesterol or lipid related disorders comprises administering a therapeutically effective amount of a disclosed compound. The disclosed compound may be administered as a pharmaceutically acceptable composition, comprising a disclosed compound and a pharmaceutically acceptable carrier. Another embodiment provides methods for the prevention of a cardiovascular, cholesterol or lipid related disorder, comprising administering to a mammal a therapeutically effective amount of a presently disclosed compound or composition.

Exemplary cardiovascular, cholesterol or lipid related disorders include, but are not limited to acute coronary syndrome, angina pectoris, arteriosclerosis, atherosclerosis, carotid atherosclerosis, cerebrovascular disease, cerebral infarction, congestive heart failure, congenital heart disease, coronary heart disease, coronary artery disease, coronary plaque stabilization, dyslipidemias, dyslipoproteinemias, endothelium dysfunctions, familial hypercholeasterolemia, familial combined hyperlipidemia, hypertension, hyperlipidemia, intermittent claudication, ischemia, ischemia reperfusion injury, ischemic heart diseases, multi-infarct dementia, myocardial infarction, peripheral vascular disease, restenosis, renal artery atherosclerosis, rheumatic heart disease, stroke, thrombotic disorder, transitory ischemic attacks, and lipoprotein abnormalities associated with Alzheimer's disease, obesity, diabetes mellitus, syndrome X and impotence.

As used herein, the term "cardiovascular disease" refers to diseases and disorders of the heart and circulatory system. These diseases are often associated with dyslipoproteinemias and/or dyslipidemias. "Endothelium dysfunction(s)" include, but are not limited to, dysfunctions affecting blood vessel elasticity; peripheral vascular disease; coronary heart disease; myocardial infarcation; cerebral infarction and restenosis. "Syndrome X" or "Metabolic Syndrome(s)" include, but are not limited to hypertension and dyslipidemia/dyslipoproteinemia.

In one embodiment, "treatment" or "treating" refers to an amelioration of a disease or disorder, or at least one discernible symptom thereof. In another embodiment, "treatment" or "treating" refers to an amelioration of at least one measurable physical parameter, not necessarily discernible by the patient. In yet another embodiment, "treatment" or "treating" refers to inhibiting the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder. For example, treating a cholesterol disorder may comprise decreasing blood cholesterol levels.

One embodiment provides a compound for administration to a patient, such as a human, as a preventative measure against cardiovascular, cholesterol or lipid related disorder. As used herein, "prevention" or "preventing" refers to a reduction of the risk of acquiring a given disease or disorder. In another embodiment, the present compositions are administered as a preventative measure to a patient, such as a human having a genetic predisposition to, for example, a cardiovascular disease, a dyslipidemia, a dyslipoproteinemia, Alzheimer's Disease, hypertension, atherosclerosis, or inflammation.

In another embodiment, the compositions of the invention are administered as a preventative measure to a patient having a non-genetic predisposition to, for example, cardiovascular disease, a dyslipidemia, a dyslipoproteinemia, Alzheimer's Disease, hypertension, atherosclerosis, or inflammation. Examples of such non-genetic predispositions include, but are not limited to, cardiac bypass surgery and percutaneous transluminal coronary angioplasty, which often leads to restenosis, an accelerated form of atherosclerosis; diabetes in women, which often leads to polycystic ovarian disease; and cardiovascular disease, which often leads to impotence. Accordingly, the present compositions may be used for the prevention of one disease or disorder and concurrently treating another (e.g., prevention of polycystic ovarian disease while treating diabetes; prevention of impotence while treating a cardiovascular disease).

Angioplasty and open heart surgery, such as coronary bypass surgery, may be required to treat cardivascular diseases, such as atherosclerosis. These surgical procedures entail using invasive surgical devices and/or implants, and are associated with a high risk of restenosis and thrombosis. Accordingly, the compounds of the invention may be used as coatings on surgical devices (e.g., catheters) and implants (e.g., stents) to reduce the risk of restenosis and thrombosis associated with invasive procedures used in the treatment of cardiovascular diseases.

The present invention provides methods for the treatment or prevention of a dyslipidemia comprising administering to a patient a therapeutically effective amount of a presently disclosed compound. In one embodiment, the compound is administered as a pharmaceutically acceptable composition. As used herein, the term "dyslipidemias" refers to disorders that lead to or are manifested by aberrant levels of circulating lipids. To the extent that levels of lipids in the blood are too high, the disclosed compounds or compositions may be administered to a patient to restore normal levels. Normal levels of lipids are reported in medical treatises known to those of skill in the art.

Dyslipidemias which the disclosed compounds or compositions are useful for preventing or treating include but are not limited to hyperlipidemia and low blood levels of high density lipoprotein (HDL) cholesterol. Hyperlipidemia includes, but is not limited to, familial hypercholesterolemia; familial combined hyperlipidemia; reduced or deficient lipoprotein lipase levels or activity, including reductions or deficiencies resulting from lipoprotein lipase mutations; hypertriglyceridemia; hypercholesterolemia; high blood levels of ketone bodies (e.g., beta-OH butyric acid); high blood levels of Lp(a) cholesterol; high blood levels of low density lipoprotein (LDL) cholesterol; high blood levels of very low density lipoprotein (VLDL) cholesterol and high blood levels of non-esterified fatty acids.

One embodiment provides methods for altering lipid metabolism in a patient, e.g., increasing the ratio of HDL to LDL in the blood of a patient, comprising administering to the patient a composition of the invention in an amount effective alter lipid metabolism.

Another embodiment provides methods for the treatment or prevention of a dyslipoproteinemia comprising administering to a patient a therapeutically effective amount of a disclosed compound or composition. As used herein, the term "dyslipoproteinemias" refers to disorders that lead to or are manifested by aberrant levels of circulating lipoproteins. To the extent that levels of lipoproteins in the blood are too high, the disclosed compounds or compositions are administered to a patient to restore normal levels. Conversely, to the extent that levels of lipoproteins in the blood are too low, the disclosed compounds or compositions are administered to a patient to restore normal levels. Normal levels of lipoproteins are reported in medical treatises known to those of skill in the art.

Dyslipoproteinemias which the disclosed compounds or compositions are useful for preventing or treating include, but are not limited to, high blood levels of LDL; high blood levels of apolipoprotein B (apo B); high blood levels of Lp(a); high blood levels of apo(a); high blood levels of VLDL; low blood levels of HDL; reduced or deficient lipoprotein lipase levels or activity, including reductions or deficiencies resulting from lipoprotein lipase mutations; hypoalphalipo-proteinemia; lipoprotein abnormalities associated with diabetes mellitus; lipoprotein abnormalities associated with obesity; lipoprotein abnormalities associated with Alzheimer's Disease; and familial combined hyperlipidemia.

One embodiment provides methods for elevating the levels of HDL associated proteins, such as ApoA-I, in the blood of a mammal, comprising administering to the mammal a composition comprising a disclosed compound or composition in an amount effective to elevate levels of HDL associated proteins in the mammal.

Another embodiment provides methods for the treatment or prevention of Alzheimer's Disease, hypertension, atherosclerosis, comprising administering to a mammal a therapeutically effective amount of a disclosed compound or composition. As used herein, "treatment or prevention of Alzheimer's Disease" encompasses treatment or prevention of lipoprotein abnormalities associated with Alzheimer's Disease.

"Diseases and conditions associated with diabetes mellitus" as defined herein comprise, but are not restricted to, hyperglycemia, hyperinsulinaemia, hyperlipidaemia, insulin resistance, impaired glucose metabolism, obesity, diabetic retinopathy, macular degeneration, cataracts, diabetic nephropathy, glomerulosclerosis, diabetic neuropathy, erectile dysfunction, premenstrual syndrome, vascular restenosis, ulcerative colitis, skin and connective tissue disorders, foot ulcerations, metabolic acidosis, arthritis, osteoporosis and impaired glucose tolerance.

Preparation of Compounds

Formula A represents a general formula for stilbenes and their analogs:

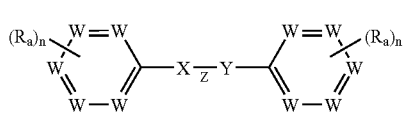

A $R_a$ may be selected from groups including, but not limited to, alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone. One of ordinary skill will appreciate that stilbene compounds and analogs thereof can be prepared according to the procedures outlined in the following schemes.

Stilbenes Comprising a —C=C— Linker

In one embodiment, the synthesis of stilbenes of Formula A can be achieved by following the procedure of Scheme 1:

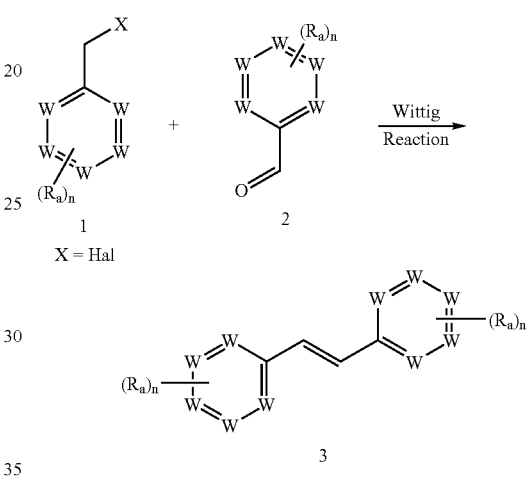

Arylalkyl halide 1 can be combined with aldehyde 2 in the presence of, for example, triphenylphosphine and NaOMe, afford alkene 3. Other methods of achieving the desired coupling include, for example, a Peterson olefination.

Stilbenes of Formula A may also be prepared via the procedure of Scheme 2:

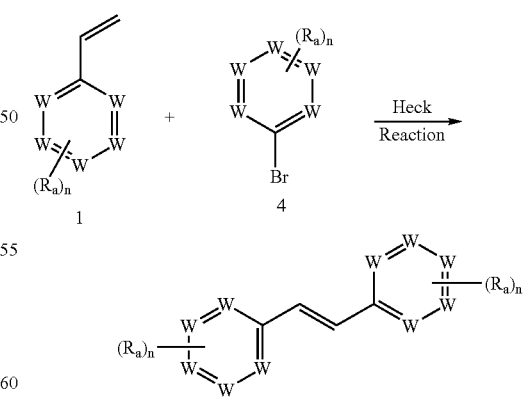

Scheme 2 illustrates arylation of styrene 1 using a Heck reaction. Bromobenzene 4 can be treated with a Pd catalyst, such as a palladium-triarylphosphine couple, to give stilbene 3. However, other methods known in the art that may be used include: 1) treatment of an aryl iodide with palladium acetate in the presence of a base (e.g., tributylamine, potassium acetate); or 2) reaction of an aromatic compound with palladium acetate or palladium metal and silver acetate in acetic acid.

The resuting alkene of the stilbenes of Schemes 1 and 2 can be reduced using a range of known reduction methods in the art to yield a —$CH_2$—$CH_2$— linker. Such methods include, but are not limited to, catalytic hydrogenation using catalysts such as Pt, Pd, or Ni, optionally in the presence of a solid support (e.g., $Al_2O_3$, $BaSO_4$), in the presence of $H_2$.

Stilbene Analogs Comprising a —$CH_2$—NH— Linker

Formula B depicts stilbene analogs comprising a —$CH_2$—NH— linker:

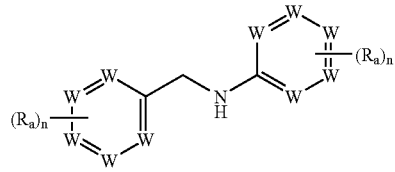

B

Stilbene analogs of Formula B may be prepared following the general procedure of Scheme 3:

Scheme 3

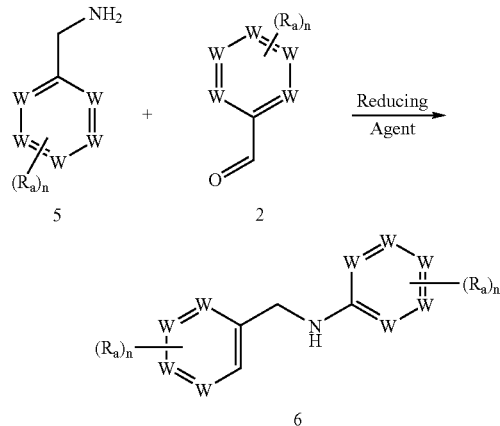

Stilbene analog 6 in Scheme 3 may be prepared using known reductive amination techniques. A Borch reaction uses $NaBH_3CN$ as a reducing agent to afford amine 6. Other reductants such as $NaBH_4$ may also be used. Alternatively, the amine 5 can be reacted with benzaldehyde 2, followed by subjection to catalytic hydrogenation conditions (such as $H_2$/Pd).

Stilbene Analogs Comprising a —$CH_2$—O— Linker

Formula C represents a general formula for stilbene analogs comprising a —$CH_2$—O— linker:

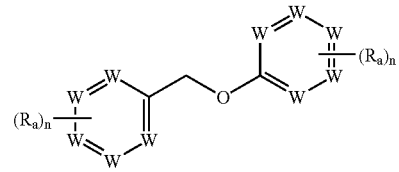

C

Stilbenes analogs comprising an aryl ether may be synthesized following the procedure of Scheme 4:

Scheme 4

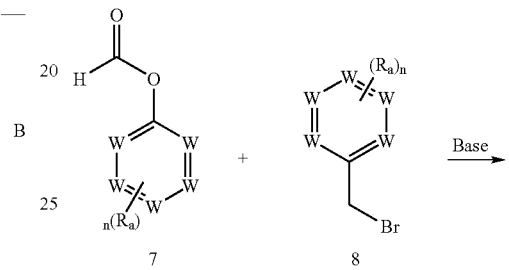

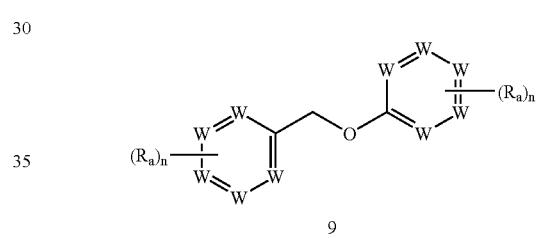

Formic acid phenyl ester 7 may be synthesized from the corresponding benzaldehyde via traditional oxidation methods known in the art. For example, Baeyer-Villiger oxidation using m-CPBA to form 7, followed by deformylation using a suitable base and exposure to bromide 8 affords stilbene analog 9.

Stilbenes Comprising a —(CO)—NH— Linker

Formula D represents a general formula for stilbene analogs comprising a —(CO)—NH— linker:

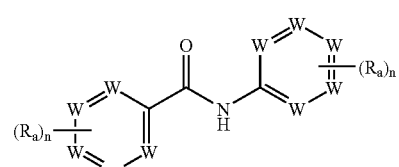

D

Stilbene analogs of Formula D can be prepared following the procedure of Scheme 5:

Scheme 5

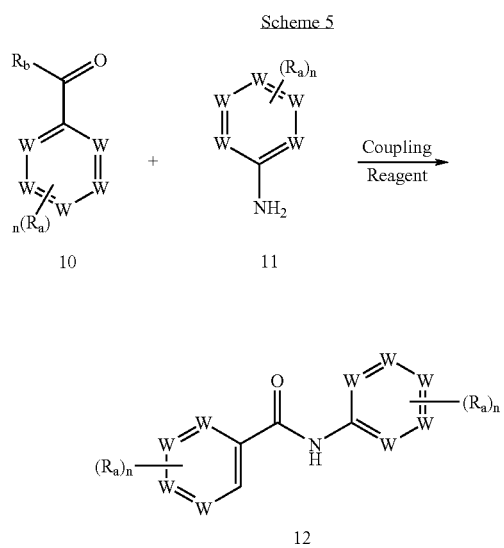

The formation of stilbene derivative 12 in Scheme 5 may use an acyl halide 10 ($R_b$=Hal) or carboxylic acid 10 ($R_b$=OH). An acyl halide, optionally in the presence of a suitable base, can react with amine 11 to afford amide 12. Amide 12 can also be prepared from the carboxylic acid 10 using known peptide coupling reagents, such as EDCI.

Chalcones

Formula E represents an exemplary chalcone compound:

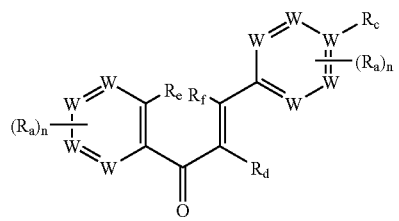

Chalcones of Formula E may be synthesized following the procedure of Scheme 6:

Scheme 5

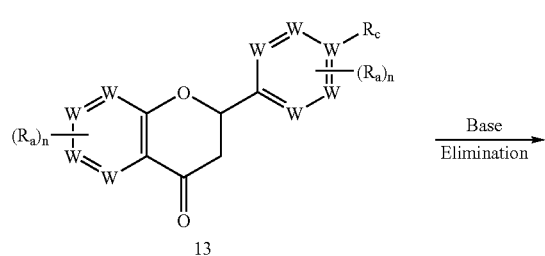

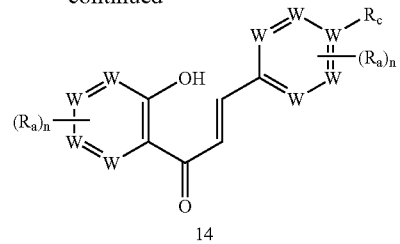

Base-catalyzed β-elimination of flavone 13 to prepare chalcone 14 can be accomplished with a strong base such as NaOH and reflux. Other conditions include heating a reaction mixture containing flavone 14 with a metal-hydroxide or metal-alkyl species.

EXAMPLES

Examples of stilbene compounds of Formula I include, but are not limited to, the following compounds.

4,4'-dihydroxy-stilbene

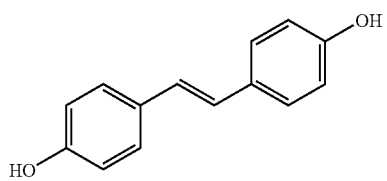

6-[(E)-2-(4-Hydroxy-phenyl)-vinyl]-pyridin-3-ol

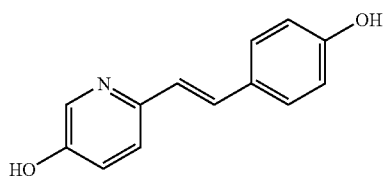

5-[(E)-2-(4-Hydroxy-phenyl)-vinyl]-pyrazin-2-ol

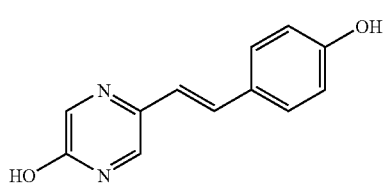

5-[(E)-2-(4-Hydroxy-phenyl)-vinyl]-pyridin-2-ol

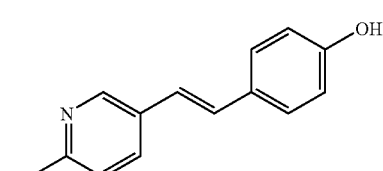

Nicotinic acid 4-[(E)-2-(4-hydroxy-phenyl)-vinyl]-phenyl ester

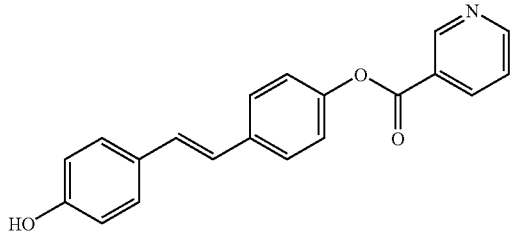

5-{[1-(4-Hydroxy-phenyl)-meth-(E)-ylidene]-amino}-pyridin-2-ol

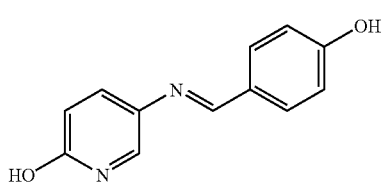

5-(4-Hydroxy-phenylazo)-pyridin-2-ol

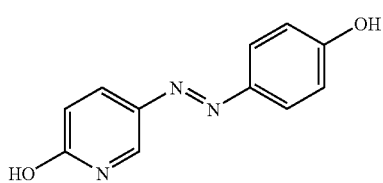

Examples of Chalcone compounds of Formula 4 include but are not limited to:
(E)-3-(4-Hydroxy-phenyl)-1-phenyl-propenone

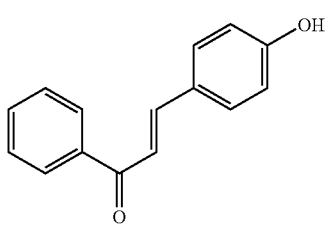

and its derivatives, including but not limited to:
(E)-3-(4-Hydroxy-phenyl)-1-pyridin-3-yl-propenone
(E)-3-(4-Hydroxy-phenyl)-1-pyridin-4-yl-propenone
(E)-3-(4-Hydroxy-phenyl)-1-pyridin-2-yl-propenone
(E)-3-(5-Hydroxy-pyridin-2-yl)-1-phenyl-propenone
(E)-3-(6-Hydroxy-pyridin-3-yl)-1-phenyl-propenone
Nicotinic acid 4-((E)-3-oxo-3-phenyl-propenyl)-phenyl ester
Nicotinic acid 4-((E)-3-oxo-3-pyridin-3-yl-propenyl)-phenyl ester
Nicotinic acid 4-((E)-3-oxo-3-pyridin-4-yl-propenyl)-phenyl ester
Nicotinic acid 4-((E)-3-oxo-3-pyridin-2-yl-propenyl)-phenyl ester
Nicotinic acid 6-((E)-3-oxo-3-phenyl-propenyl)-pyridin-3-yl ester
Nicotinic acid 5-((E)-3-oxo-3-phenyl-propenyl)-pyridin-2-yl ester
[5-Hydroxy-2-((E)-3-oxo-3-phenyl-propenyl)-phenyl]-carbamic acid ethyl ester
[5-Hydroxy-2-((E)-3-oxo-3-pyridin-3-yl-propenyl)-phenyl]-carbamic acid ethyl ester
[5-Hydroxy-2-((E)-3-oxo-3-pyridin-4-yl-propenyl)-phenyl]-carbamic acid ethyl ester
[5-Hydroxy-2-((E)-3-oxo-3-pyridin-2-yl-propenyl)-phenyl]-carbamic acid ethyl ester
[5-Hydroxy-2-((E)-3-oxo-3-phenyl-propenyl)-pyridin-3-yl]-carbamic acid ethyl ester
[2-Hydroxy-5-((E)-3-oxo-3-phenyl-propenyl)-pyridin-4-yl]-carbamic acid ethyl ester
Nicotinic acid 3-ethoxycarbonylamino-4-((E)-3-oxo-3-phenyl-propenyl)-phenyl ester
Nicotinic acid 3-ethoxycarbonylamino-4-((E)-3-oxo-3-pyridin-3-yl-propenyl)-phenyl ester
Nicotinic acid 3-ethoxycarbonylamino-4-((E)-3-oxo-3-pyridin-4-yl-propenyl)-phenyl ester
Nicotinic acid 3-ethoxycarbonylamino-4-((E)-3-oxo-3-pyridin-2-yl-propenyl)-phenyl ester
Nicotinic acid 5-ethoxycarbonylamino-6-((E)-3-oxo-3-phenyl-propenyl)-pyridin-3-yl ester
Nicotinic acid 4-ethoxycarbonylamino-5-((E)-3-oxo-3-phenyl-propenyl)-pyridin-2-yl ester.

The following compounds were obtained from commercially available sources (such as Indofine Chemical Company, Inc.): 4,4'-dihydroxystilbene; 4-hydroxychalcone; 4-methoxychalcone; 4,2',4'-trihydroxychalcone; 2,4-dihydroxy-4'-methoxychalcone; and 4,2',4',6'-tetramethoxychalcone.

Abbreviations used herein denote the following compounds, reagents and substituents: N-methylpyrrolidinone (NMP); dichloromethane (DCM); dimethylaminopyridine (DMAP); dimethylformamide (DMF); dimethylsulfoxide (DMSO); ethanol (EtOH); ethyl acetate (EtOAc); 1-ethyl-3-(3-dimethyaminopropyl)carbodiimide (EDCI); lithium aluminum hydride (LAH); methanol (MeOH); methoxymethyl (MOM); and tetrahydrofuran (THF).

Example 1

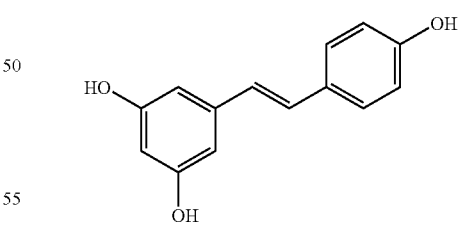

5[(E)-2-(4-Hydroxyphenyl)-vinyl]benzene 1,3-diol (Resveratrol)

To a solution of 4-methoxy-benzyltriphenylphosphonium bromide (12.5 g) in anhydrous tetrahydrofuran (200 mL) at −78° C. was added n-butyllithium (2.44 M, 1.0 equiv), and the resulting red solution was stirred under argon for 2-4 h. A solution of 3,5-dimethoxybenzaldehyde (4.5 g) in tetrahydrofuran was added dropwise over 30 min and the mixture stirred for 6-15 h. The resulting cream suspension was poured into water and extracted with dichloromethane. The organic phase was washed with water, and removal of the solvent in vacuo afforded an oil. The oil was separated by flash column chromatography (49:1 hexane/ethyl acetate). The cis-stilbene eluted first as a clear oil followed by the trans isomer as a colorless solid or oil. Overall yield: 91%. To a solution of the trans isomer (3.1. g) in anhydrous dichloromethane (150 mL) at −78° C. was added (dropwise) boron tribromide (1.0 M, 34.5 mL), and the resulting red solution was stirred under argon for 30 min. The solution was poured into water and extracted with dichloromethane. The organic phase was washed with water, and removal of the solvent in vacuo afforded an oil, which was separated by flash column chromatography (1:1 hexane/ethyl acetate) to afford a colorless solid (2.26 g, 86%): mp 260° C.

Example 2

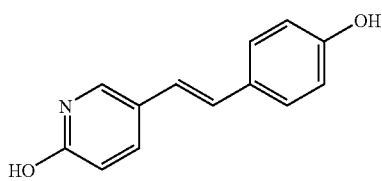

5-[(E)-2-(4-Hydroxyphenyl)-vinyl]-pyridin-2-ol (4-Methoxybenzyl)triphenylphosphonium chloride (4.79 g, 11.4 mmol) was suspended in 50 mL of dry methanol. Sodium methoxide (4.94 g of 25% solution in methanol, 22.8 mmol) was added in one portion to the above suspension and the resulting mixture was stirred at room temperature under nitrogen for 30 minutes. Pyridinecarbaldehyde (1.57 g, 11.4 mmol) was then added and the stirring was continued at room temperature overnight. Excess of sodium methoxide was quenched by addition of water and pH of the reaction mixture was adjusted to pH=4.5 with 1 N HCl, and then to pH=7.5-8.0 by addition of saturated sodium bicarbonate. Products were then extracted with ethyl acetate (500 mL). Combined extracts were washed with water and brine, and concentrated in vacuo. The crude product was purified by column chromatography using ethyl acetate in hexane (5%-10%) to give 1.27 g (46%) of trans-stilbene.

The trans-stilbene (1.17 g, 4.85 mmol) was dissolved in dry NMP (12 mL). Thiophenol (1.07 g, 9.7 mmol) was then added to the above solution, followed by addition of $K_2CO_3$ (67 mg, 0.48 mmol). The resulting mixture was heated for 8 hours at 195° C. under nitrogen. The cooled reaction mixture was made alkaline with 1 N NaOH (pH=10), and the neutral components were extracted with ether (3×50 mL). The aqueous layer was acidified to pH=4 with 1 N HCl and stirred at room temperature for 30 minutes, and extracted with ether (2×50 mL). Then pH was adjusted to pH=8 with saturated $NaHCO_3$. The solid was isolated by filtration, washed with water (100 mL), ethyl acetate (50 mL) and ether (30 mL), and air-dried to yield 5-[(E)-2-(4-hydroxyphenyl)-vinyl]-pyridin-2-ol (715 mg, 69%). MS (ES) m/z: 214.08 (M+1); $^{13}$C-NMR (DMSO-$d_6$): δ 162.42, 157.50, 138.21, 134.07, 129.04, 127.92, 125.67, 121.59, 121.03, 116.89, and 116.18.

Example 3

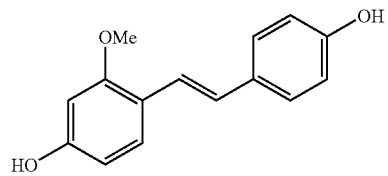

4-[(E)-2-(4-Hydroxyphenyl)-vinyl]-3-methoxy-phenol

In a 50 mL round-bottomed flask fitted with condenser and magnetic stirrer were placed 4-bromo-3-methoxyphenol (2.0 g, 9.85 mmol), $Ac_2O$ (1.206 g, 11.82 mmol), $Et_3N$ (1.196 g, 11.82 mmol) and catalytic amount of DMAP and the reaction mixture was stirred for 24 h at room temperature. The reaction mixture was poured into water and extracted with ethyl acetate. The organic layer washed with water, dried and concentrated to give 4-acetoxy-3-methoxy-bromobenzene (2.4 g, 99%).

To a stirred solution of 4-acetoxy-3-methoxy-bromobenzene (3.549 g, 14.48 mmol) in acetonitrile (60 mL), were added 4-acetoxystyrene (2.47 g, 15.21 mmol), N,N-diisopropylethylamine (5.61 g, 43.45 mmol), biphenyl-2-yl-di-t-butyl phosphine (259 mg, 0.87 mmol) and palladium acetate (195 mg, 0.87 mmol) under $N_2$. The reaction mixture was heated to 80° C. for 48 h and then cooled to room temperature. Water was added and the mixture was extracted with ethyl acetate. The organic layer was separated, washed with water, brine, dried and concentrated to give crude product, which was purified by column chromatography, using 10% ethyl acetate in hexane to give (220 mg) of diacetoxystillbene.

To a solution of diacetoxystillbene (220 mg, 0.675 mmol) in methanol: THF (10 mL: 4 mL), $K_2CO_3$ (466 mg, 3.37 mmol) was added and stirred for 25 minutes at room temperature. Then the reaction mixture was neutralized by dilute HCl and extracted by ethyl acetate, the combined organic layer was washed with water, brine, dried and concentrated to give a crude product, which was purified by column chromatography using 50% ethyl acetate in hexane, to give 140 mg (85%) of 4-[(E)-2-(4-hydroxyphenyl)-vinyl]-3-methoxy-phenol. MS (ES) m/z: 243.11 (M+1), 242.07 (M), 215.05, 193.08, and 182.99; $^{13}$C-NMR (CD$_3$OD): δ 158.07, 158.02, 156.50, 130.43, 127.11, 126.57, 125.62, 120.40, 118.47, 115.18, 107.33, 98.58, and 54.64; Mp. 192-194° C.

Example 4

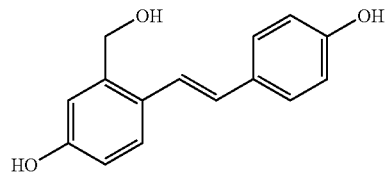

3-Hydroxymethyl-4-[(E)-2-(4-hydroxy-phenyl)-vinyl]-phenol

To a stirred solution of methyl-2-bromo-5-methoxy benzoate (4.0 g, 16.32 mmol) in acetonitrile (80 mL), were added 4-methoxystyrene (2.3 g, 17.14 mmol), N,N-diisopropylethylamine (6.33 g, 48.98 mmol), biphenyl-2-yl-di-t-butyl phosphine (292 mg, 0.98 mmol) and palladium acetate (220 mg, 0.98 mmol) under $N_2$. The reaction mixture was heated to 80° C. for 48 h and then cooled to rt. Water was added and the mixture was extracted with ethyl acetate. The organic layer was separated, washed with water, brine, dried and concentrated to give the crude product, which was purified by column chromatography, using 15% ethyl acetate in hexane to give (1.5 g, 30%) of dimethoxy-stillbene ester intermediate.

To a suspension of LAH (106 mg, 2.82 mmol) in THF (20 mL), the dimethoxy-stillbene ester intermediate (700 mg, 2.34 mmol) in THF (10 mL) was added slowly at 0° C. and resulting mixture was stirred at 0° C. for 2 h. The reaction was quenched by adding diluted NaOH at 0° C. then extracted with ethyl acetate. The combined organic layers were washed with water, brine, dried and concentrated to give the crude product, which was purified by column chromatography using 30% ethyl acetate in hexane, to give 572 mg (90%) of the dimethoxystilbene.

To a solution of the dimethoxystillbene (572 mg, 2.12 mmol) in NMP (10 mL), thiophenol (513 mg, 4.66 mmol) and $K_2CO_3$ (29 mg, 0.212 mmol) was added and resulting mixture was heated at 190° C. for 7 h. Then the reaction mixture was diluted with water, made alkaline by using 1 N NaOH and extracted with ethyl acetate. The combined organic layers were washed with water, brine, dried and concentrated to give a crude product, which was purified by column chromatography using 5% methanol in ethyl acetate, to give 120 mg (23%) of 3-hydroxymethyl-4-[(E)-2-(4-hydroxy-phenyl)-vinyl]-phenol. MS (ES) m/z: 241.15 (M), and 141.12; $^{13}$C-NMR (CD$_3$OD): δ 156.85, 156.66, 139.46, 129.84, 128.03, 127.82, 127.45, 126.46, 122.19, 115.21, 114.81, 114.51, and 62.09; Mp. 223-225° C.

Example 5

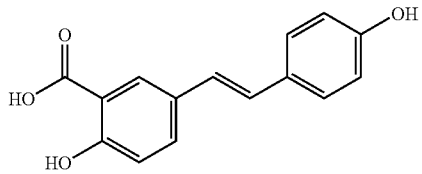

2-Hydroxy-5-[(E)-2-(4-hydroxyphenyl)vinyl]benzoic acid

In a 50 mL round-bottomed flask fitted with condenser and magnetic stirrer were placed methyl 5-bromosalicylate (5.0 g, 21.64 mmol), Ac$_2$O (2.65 g, 25.97 mmol), Et$_3$N (2.63 g, 25.97 mmol) and catalytic amount of DMAP. The reaction mixture was stirred for 24 h at room temperature. The reaction mixture was poured into water and extracted with ethyl acetate. The organic layer was washed with water, dried and concentrated to give methyl 2-acetoxy-5-bromobenzoate (5.9 g, 98%). To a stirred solution of methyl 2-acetoxy-5-bromobenzoate (5.9 g, 21.61 mmol) in acetonitrile (80 mL) were added 4-acetoxystyrene (3.68 g, 22.69 mmol), N,N-diisopropylethylamine (8.38 g, 64.82 mmol), biphenyl-2-yl-di-t-butyl phosphine (368 mg, 1.29 mmol) and palladium acetate (291 mg, 1.29 mmol) under $N_2$. The reaction mixture was heated to 80° C. for 48 h and then cooled to room temperature. Water was added and the mixture was extracted with ethyl acetate. The organic layer was separated, washed with water, brine, dried and concentrated to give crude product, which was purified by column chromatography, using 20% ethyl acetate in hexane to give (3.19 g, 42%) of the di-acetoxy stilbene. To a solution of the di-acetoxy stillbene (500 mg, 1.41 mmol) in acetonitrile: THF (10 mL: 10 mL), NaOH (388 mg, 8.47 mmol) was added and stirred for 24 h at room temperature. The reaction mixture was neutralized by dilute HCl and extracted with ethyl acetate. The combined organic layers were washed with water, brine, dried and concentrated to give a crude product, which was purified by crystallization in ethyl acetate and hexane to give 2-hydroxy-5-[(E)-2-(4-hydroxyphenyl)vinyl] benzoic acid (250 mg, 69%). MS (ES) m/z: 256.06 (M), 255.05 (M–1); $^{13}$C-NMR (CD$_3$OD): δ 172.3, 161.1, 157.1, 132.7, 129.6, 129.3, 128.0, 127.5, 127.1, 124.3, 117.4, 115.3, 112.7. Mp. 241-243° C.

Example 6

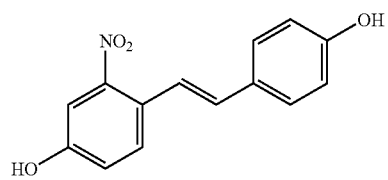

3-Nitro-4-[(E)-2-(4-hydroxyphenyl)-vinyl]phenol

To a stirred solution of 2-bromo-5-methoxynitrobenzene (5 g, 21.6 mmol) in dry acetonitrile (60 mL) were added 4-methoxystyrene (3.04 g, 22.6 mmol), N,N-diisopropylethylamine (8.36 g, 64.6 mmol), biphenyl-2-yl-di-t-butyl phosphine (385 mg, 1.3 mmol) and palladium acetate (290 mg, 1.3 mmol). The resulting mixture was heated at 80° C. overnight under $N_2$. The reaction mixture was cooled to room temperature and partitioned between ethyl acetate and water. The organic layer was separated, washed with water, brine, and dried over magnesium sulfate. Concentration under reduced pressure gave the crude product which was purified by column chromatography using ethyl acetate in hexane (5%-10%) to give the protected nitro-stilbene (4.4 g, 72%).

The nitro-stilbene (1.45 g, 5.09 mmol) was placed in the round bottom flask under nitrogen. Pyridinium hydrochloride (8.82 g, 76.3 mmol) was then added and the mixture was heated to 190° C. for 2 hours. After cooling to room temperature 50 mL of water was added and the product was extracted with ethyl acetate (3×80 mL). The combined extracts were washed with water and brine, and dried over magnesium sulfate. The solvent was then removed in vacuo and the crude product was purified by column chromatography using 10%-20% ethyl acetate in hexane to afford 3-nitro-4-[(E)-2-(4-hydroxyphenyl)-vinyl]phenol (480 mg, 37%). MS (ES) m/z: 257.08 (M), 256.11 (M–1); $^{13}$C-NMR (DMSO-d$_6$): δ 158.3, 157.5, 148.8, 131.6, 129.6, 128.8, 128.5, 123.8, 121.7, 119.9, 116.3, 111.0.

Mp. 237-240° C.

Example 7

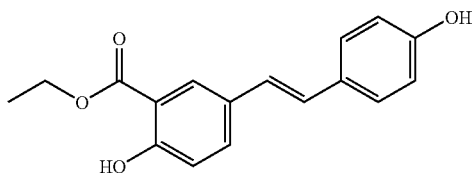

(E)-Ethyl 2-hydroxy-5-(4-hydroxystyryl)benzoate

In a 50 mL round-bottomed flask fitted with condenser and magnetic stirrer were placed methyl 5-bromosalicylate (5.0 g, 21.64 mmol), Ac$_2$O (2.65 g, 25.97 mmol), Et$_3$N (2.63 g, 25.97 mmol) and catalytic amount of DMAP. The reaction mixture was stirred for 24 h at rt. The reaction mixture was poured into water and extracted with EtOAc. The organic layer was washed with water, dried and concentrated to give the acetoxy derivative (5.9 g, 98%). To a stirred solution of methyl 2-acetoxy-5-bromobenzoate (5.9 g, 21.61 mmol) in acetonitrile (80 mL) were added 4-acetoxystyrene (3.68 g, 22.69 mmol), N,N-diisopropylethylamine (8.38 g, 64.82 mmol), biphenyl-2-yl-di-t-butyl phosphine (368 mg, 1.29 mmol) and palladium acetate (291 mg, 1.29 mmol) under N$_2$. The reaction mixture was heated to 80° C. for 48 h and then cooled to rt. Water was added and the mixture was extracted with EtOAc. The organic layer was separated, washed with water, brine, dried and concentrated to give crude product, which was purified by column chromatography, using 20% EtOAc in hexane to give (3.19 g, 42%) of the di-acetoxy stillbene. The di-acetoxystillbene (500 mg, 1.41 mmol) was treated with ammonia (2M solution in ethanol, 15 mL) in a sealed tube at 115° C. for 12 h. The reaction mixture was cooled to rt. The solvent was removed and the crude product was purified by column chromatography using 50% EtOAc in hexane to give the product (200 mg, 50%).

MS (ES) m/z: 284.12 (M), 283.14 (M−1); $^{13}$C-NMR (DMSO-d$_6$): δ 169.5, 159.9, 157.8, 133.2, 130.4, 129.9, 128.8, 128.4, 128.3, 127.8, 124.5, 118.6, 116.2, 115.9, 113.9, 62.1, 14.7; Mp. 269-271° C.

Example 8

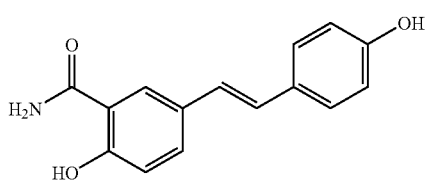

(E)-2-Hydroxy-5-(4-hydroxystyryl)benzamide (E)-2-Hydroxy-5-(4-hydroxystyryl)benzamide was isolated (75 mg, 20%) with (E)-ethyl 2-hydroxy-5-(4-hydroxystyryl)benzoate in the procedure set. forth in Example 7. Selected data for (E)-2-hydroxy-5-(4-hydroxystyryl)benzamide:

MS (ES) m/z: 254.07 (M−1); $^{13}$C-NMR (DMSO-d$_6$): δ 172.7, 160.9, 157.8, 132.8, 129.0, 128.8, 128.1, 127.4, 125.8, 125.0, 118.3, 116.3, 115.8, 115.1. Mp. 272-274° C.

Example 9

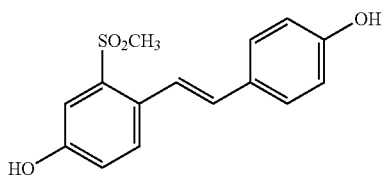

4-[(E)-2-(4-Hydroxyphenyl)vinyl]-3-methanesulfonylphenol

To a solution of 3-methoxythioanisole (3.084 g, 20 mmol) in 300 mL acetone was added a solution of oxone (30.74 g, 50 mmol) in 125 mL water, resulting in the formation of a white precipitate. Stirring continued overnight, and the solid was filtered off and washed with acetone. Filtrate was concentrated to remove acetone. Aqueous layer was extracted with EtOAc (2×200 mL) and dried over Na$_2$SO$_4$. The solvent was removed to give 1-methanesulfonyl-3-methoxy benzene (3.68 g, 98%) as oil.

1-Methanesulfonyl-3-methoxy benzene was dissolved in 90 mL glacial acetic acid. 100 mL water was added. A solution of bromine (4.79 g, 30 mmol) in 10 mL acetic acid was added dropwise at 10° C. The stirring was continued at rt for 15 h. The pH of the mixture was adjusted to pH 8 with aqueous NaOH solution, and extracted with EtOAc (3×200 mL) and dried over Na$_2$SO$_4$. The crude compound was purified by column chromatography (SilicaGel 230-400 mesh; 20% EtOAc in hexanes as an eluent) to give 1-bromo-2-methanesulfonyl-4-methoxy benzene (2.4 g, 45%).

To a stirred solution of 1-bromo-2-methanesulfonyl-4-methoxy benzene in anhyd. acetonitrile were added 4-acetoxystyrene (1.413 g, 8.715 mmol), N,N-diisopropylethylamine (3.218 g, 24.9 mmol), biphenyl-2-yl-di-tert-butylphophine (0.149 g, 0.5 mmol) and palladium acetate (0.112 g, 0.5 mmol). The resulting mixture was stirred at 80° C. for 15 h under nitrogen. The mixture was cooled to rt, and the solvent was removed under reduced pressure. The residue was dissolved in 50 mL EtOAc, washed with water and brine and dried over anhydrous Na$_2$SO$_4$. Purification by column chromatography (SilicaGel 230-400 mesh; 20% EtOAc in hexanes as an eluent) gave 4-[2-(2-methanesulfonyl)-4-methoxyphenylvinyl]phenyl acetate 1.245 g (43% yield).

4-[2-(2-Methanesulfonyl)-4-methoxyphenylvinyl]phenyl acetate (1.2 g, 3.5 mmol) and pyridinium hydrochloride (6.07 g, 52.5 mmol) were mixed together and stirred at 190° C. for 15 h. The mixture was cooled to rt and washed with water. The residue was purified by column chromatography (SilicaGel 70-200 mesh; 25 MeOH in dichloromethane) to give 4-[(E)-2-(4-hydroxyphenyl)vinyl]-3-methanesulfonylphenol (0.35 g, 33%) as an off-white solid. MS (ES) m/z: 291.06 (M+1), 290.10 (M), 289.07 (M−1); $^{13}$C-NMR (CD$_3$OD): δ 157.8, 157.1, 137.9, 131.8, 129.2, 129.0, 128.9, 128.0, 121.0, 120.5, 120.4, 115.4, 114.9. Mp. 244-245° C.

Example 10

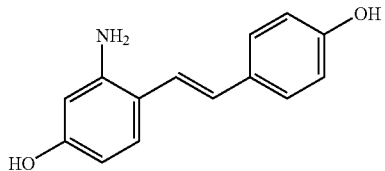

3-Amino-4-[(E)-2-(4-hydroxy-phenyl)vinyl]phenol

To a solution of the product of 3-nitro-4-[(E)-2-(4-hydroxyphenyl)-vinyl]phenol (216 mg, 0.84 mmol) in acetone (6 mL) was added a solution of ammonium chloride (89.9 mg, 1.68 mmol) in 2 mL of water. The mixture was heated to reflux, and the oil bath was removed. Zinc dust (164.8 mg, 2.5 mmol) was added in small portions to the reaction mixture to maintain a moderate reaction. After the reaction subsided an additional portion of zinc (82.4 mg, 1.25 mmol) was added. The reaction mixture was then heated to reflux for an additional 2 h. The precipitate was removed by filtration, washed with acetone (2×20 mL) and with ethyl acetate (2×30 mL). The combined washings were concentrated in vacuo and the crude product was purified by column chromatography using 5% methanol in dichloromethane to afford 3-Amino-4-[(E)-2-(4-hydroxy-phenyl)vinyl]phenol (155 mg, 72%). MS (ES) m/z: 228.11 (M+1), 134.06; $^{13}$C-NMR (DMSO-$d_6$): δ 158.3, 156.9, 147.9, 130.4, 130.2, 127.9, 126.9, 124.5, 122.0, 115.9, 115.5, 114.2, 105.4, 102.2. Mp. 229-232° C.

Example 11

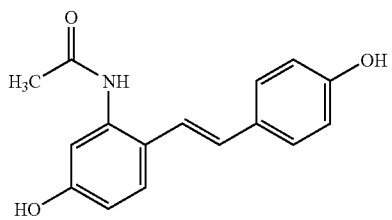

N-{5-Hydroxy-2-[(E)-2-(4-hydroxyphenyl)vinyl]phenyl}-acetamide

To the solution of 3-amino-4-[(E)-2-(4-hydroxy-phenyl)vinyl]phenol (100 mg) in anhydrous THF was added 225 mg of acetic anhydride and 223 mg of Et$_3$N. The resulting solution was stirred at rt overnight. The reaction mixture was concentrated by vacuum evaporation. The residue, which was identified as mainly desired compound by $^1$H-NMR, was not further purified and used directly for the next step. The crude mixture from the previous reaction was dissolved in 30 mL of methanol. K$_2$Co$_3$ (197 mg, ~12 eq.) was added as well as 20 mL of H$_2$O. The resulting solution was vigorously stirred at rt for 1 h. All volatile solvents were evaporated and the residue was loaded on a silica gel column with 5% MeOH/dichloromethane as eluent to give N-{5-hydroxy-2-[(E)-2-(4-hydroxyphenyl)vinyl]phenyl}-acetamide (55 mg, 46.4% in two steps). MS (ES) m/z: 270.14 (M+1); Mp. 227-229° C.

Example 12

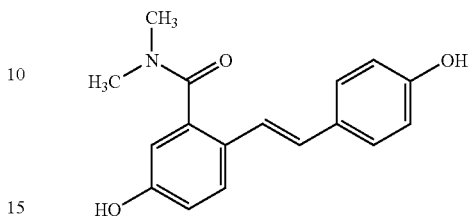

5-Hydroxy-2-[2-(4-hydroxyphenyl)vinyl]-N,N-dimethylbenzamide

To a stirred solution of methyl 2-bromo-5-methoxybenzoate (4.0 g, 16.32 mmol) in acetonitrile (80 mL), were added 4-methoxystyrene (2.3 g, 17.14 mmol), N,N-diisopropylethylamine (6.33 g, 48.98 mmol), biphenyl-2-yl-di-t-butyl phosphine (292 mg, 0.98 mmol) and palladium acetate (220 mg, 0.98 mmol) under N$_2$. The reaction mixture was heated to 80° C. for 48 h and then cooled to rt. Water was added and the mixture was extracted with EtOAc. The organic layer was separated, washed with water, brine, dried and concentrated to give the crude product, which was purified by column chromatography, using 15% EtOAc in hexane to give (1.5 g, 30%) the stilbene methyl benzoate.

The above stilbene methyl benzoate (485 mg, 1.6 mmol) was dissolved in 20 mL of THF-acetonitrile (1:1). LiOH (hydrate, 102.4 mg, 2.4 mmol) dissolved in 1 mL of water was added to the above solution and the resulting reaction mixture was stirred at rt overnight. Most of the solvent was removed in vacuo, 10 mL of water was added, and the pH was adjusted to pH=3 by addition of 2 N HCl. The product was extracted with EtOAc (3×30 mL). The extracts were washed with water, brine, and dried over MgSO$_4$. Concentration under reduced pressure gave the crude product, which was purified by column chromatography (5% MeOH-dichloromethane) to afford 462 mg (quantitative yield) of the stilbene carboxylic acid.

The stilbene carboxylic acid (462 mg, 1.6 mmol) was dissolved in 10 mL of dry dichloromethane. Oxalyl chloride (227 mg, 1.79 mmol) was added at rt under nitrogen atmosphere and the resulting mixture was stirred for 2 hs. Et$_3$N (247 mg, 2.44 mmol) was then added, followed by addition of dimethylamine (2 M solution in THF, 1.6 mL). The solution was stirred at rt overnight. Volatiles were removed in vacuo, and the residue was partitioned between EtOAc and water. The organic layer was separated, washed with water, brine, and dried over magnesium sulfate. Concentration under reduced pressure gave the crude product (510 mg, quantitative yield) which was used in the next step without further purification. The above stilbene (510 mg, 1.6 mmol) was mixed with pyridinium hydrochloride (2.82 g, 24.4 mmol) was added and the resulting mixture was heated at 190° C. for 3 hs. Water (20 mL) was added and the product was extracted with EtOAc (3×50 mL). The organic extracts were washed with water, brine, and dried over magnesium sulfate. Concentration in vacuo gave the crude product which was purified by column chromatography (5% MeOH-dichloromethane) to afford 210 mg of the product (46% yield). Further purification by recrystallization from EtOAc/hexane gave 5-hydroxy-2-[2-(4-hydroxyphenyl)vinyl]-N,N-dimethylbenzamide (100 mg). MS (ES) m/z: 282.94 (M), 281.92 (M−1); Mp. 183.5-187.7° C.

Example 13

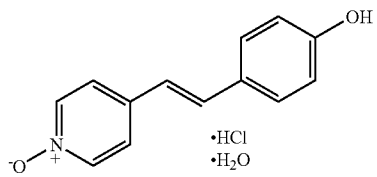

N-Oxide 4'-hydroxystilbene hydrochloride

To 4-hydroxybenzaldehyde (2 g) in 40 mL of acetone was added 5.65 g of $K_2CO_3$. The resulting mixture was stirred at rt for 15 min, before the addition of 1.58 g of MOMCl. The stirring was continued overnight. After the solid was filtered off, the evaporation of the solvent afforded pure MOM-protected phenol in quantitative yield. To the mixture of 4-methyl pyridine N-oxide (1.07 g) and the above protected benzaldehyde (1 g) in 10 mL of EtOH was added NaOEt potion-wise. Gas evolution was observed. After the addition, the reaction mixture was stirred at rt overnight. EtOH was evaporated and 20 mL of water were added. The solution was extracted by EtOAc (3×30 mL). The combined EtOAc extracts were dried over anhydrous $MgSO_4$ and evaporated under vacuum. Column chromatography afforded 1.6 g of the pure stilbene in 62% yield. The obtained product (200 mg) was dissolved in 10 mL of THF. Then 6 mL of 1 M HCl was added. The color of the solution changed from yellow to orange. The stirring was continued for 2 h. The reaction solution was left one day without any movement. Some precipitate formed during the day. The solid was filtered off and washed with 20% EtOAc/hexane to afford 137 mg, of product (66%). MS (ES) m/z: 214.94 (M+1), 213.95 (M); Mp. 247-249° C.

Example 14

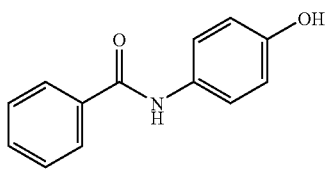

N-(4-Hydroxy-phenyl)-benzamide

To a solution of 4-hydroxyaniline (2.03 g, 18.6 mmol) in dry dichloromethane (40 mL) was added $Et_3N$ (2.63 g, 26.0 mmol), followed by addition of benzoyl chloride (2.70 g, 19.1 mmol). The resulting mixture was stirred at rt under nitrogen for 17 h. Water (100 mL) was then added and the product was extracted with EtOAc (3×100 mL). The extracts were combined and the organic layer was washed consecutively with 1 N HCl, water, saturated sodium bicarbonate solution, water, and brine, and dried over $MgSO_4$. After filtration and concentration in vacuo, the crude product obtained was purified by flash column chromatography (using 20% EtOAc in hexane) to afford 680 mg of product (17%). Further purification by recrystallization from EtOAc and hexane afforded 170 mg of N-(4-hydroxy-phenyl)-benzamide. MS (ES) m/z: 214.08 (M+1).

Example 15

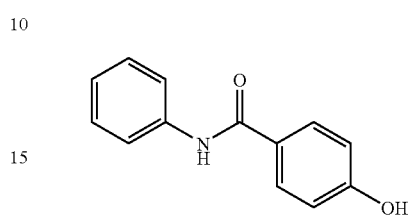

4-Hydroxy-N-phenyl-benzamide

4-Hydroxybenzoic acid (1.1 g, 7.96 mmoL) and aniline (742 mg, 7.23 mmol) were dissolved in 20 mL of dry DMF. To the above solution EDCI (1.53 g, 7.23 mmol) was added in one portion and the resulting mixture was stirred at rt overnight under nitrogen. The reaction mixture was then partitioned between EtOAc (200 mL) and water (200 mL). The organic layer was separated, washed consecutively with 1 N HCl, water, saturated sodium bicarbonate solution, water, and brine, and dried over $MgSO_4$. Solvent was removed under reduced pressure and the crude product was purified by column chromatography using 10% EtOAc in hexane to give 450 mg (29% yield) of 4-Hydroxy-N-phenyl-benzamide. MS (ES) m/z: 214.08 (M+1).

Example 16

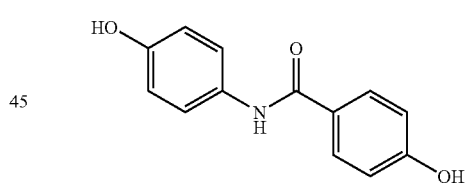

4-Hydroxy-N-(4-hydroxyphenyl)-benzamide

4-Hydroxybenzoic acid (1.01 g, 7.31 mmol) and 4-aminophenol (1.19 g, 10.9 mmol) were dissolved in 15 mL of dry DMF. To the above solution EDCI (1.40 g, 7.31 mmoL) was added in one portion and the resulting mixture was stirred at rt overnight under nitrogen. The reaction mixture was then partitioned between EtOAc (200 mL) and water (200 mL). The organic layer was separated, washed consecutively with 1 N HCl, water, saturated sodium bicarbonate solution, water, and brine, and dried over $MgSO_4$. Solvent was removed under reduced pressure and the crude product was purified by column chromatography using EtOAc in hexane as an eluent (10% to 20%) to give 580 mg (34% yield) of 4-hydroxy-N-(4-hydroxyphenyl)-benzamide. MS (ES) m/z: 230.04 (M+1).

Example 17

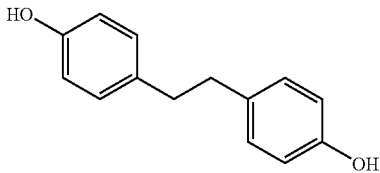

4-[4-Hydroxy-phenethyl]-phenol

A solution of 4,4'-dihydroxystilbene (250 mg, 1.178 mmol) in MeOH (10 mL) and EtOAc (2 mL) containing 5% Pd-C (120 mg) was stirred under an atmosphere of hydrogen for 2 h. The catalyst was removed by filtration and the filtrate was concentrated. Chromatography purification of the crude product on silica gel (hexane-EtOAc 3:1, 2;1) provided 245 mg of 4-[4-Hydroxy-phenethyl]-phenol (97%) as a white solid. MS (ES) m/z: 213.05 (M−1).

Example 18

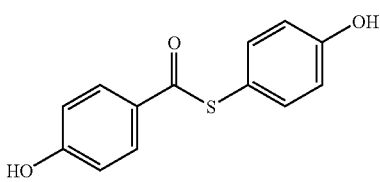

4-Hydroxy-thiobenzoic acid
S-(4-hydroxy-phenyl)ester

A PPE (polyphosphate ester) solution (7 mL) was added to a mixture of 4-hydroxybenzoic acid (552 mg, 4 mmol) and 4-mercaptophenol (554 mg, 4.4 mmol). After stirring for 16 h, the solvents were removed by evaporation and the residue was purified by column chromatography (hexane-EtOAc 7:1 to 1:1). 4-Hydroxy-thiobenzoic acid S-(4-hydroxy-phenyl) ester (240 mg, 24%) was obtained as a white solid. MS (ES) m/z: 247.04 (M+1), 167.03, and 122.55. $^{13}$C-NMR (DMSO-d$_6$): δ 188.24, 162.85, 158.82, 135.87, 129.59, 127.10, 116.33, 115.72, and 115.34.

Example 19

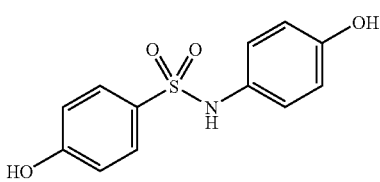

4-Hydroxy-N-(4-hydroxyphenyl)-benzenesulfonamide

A solution of thionyl chloride (15 g, 9.2 mL) and DMF (150 mg, 0.16 mL) was added to sodium 4-hydroxybenzenesulfonate (4.9 g, 25 mmol). The resulting mixture was stirred at 60° C. for 3.5 h. The solution was poured into ice and stirred for 5 min. The aqueous solution was extracted with dichloromethane, dried over sodium sulfate and evaporated to provide sulfonyl chloride (4.7 g, 97%) as an oil. The crude product (~1.9 mmol) and 4-hydroxybenzylamine (207 mg, 1.9 mmol) were stirred in pyridine (6 mL) for 2 h and evaporated. The residue was purified by two columns of silica gel (a. hexane-acetone 3:1 to 1:1, (b. MeOH in dichloromethane 2% to 7%) to afford 4-hydroxy-N-(4-hydroxyphenyl)-benzenesulfonamide (140 mg, 28%) as a brownish solid. MS (ES) m/z: 265.12 (M), 264.08 (M−1); C-NMR (CD$_3$OD): δ 161.0, 154.5, 129.5, 129.0, 128.8, 124.0, 115.5, 115.3.

Example 20

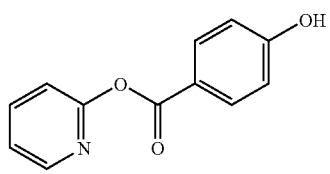

4-Hydroxy-benzoic acid pyridin-2-yl ester

To a solution of 4-hydroxybenzoic acid (2.05 g, 14.8 mmol) in dry DMF (20 mL) was added a solution of imidazole (4.04 g, 59.4 mmol) in 20 mL of DMF, followed by a solution of tert-butyldimethylsilyl chloride (4.69 g, 31.2 mmol). The mixture was stirred at 60° C. under nitrogen for 16 h and then poured over ice water (100 g). The aqueous phase was extracted with ether (3×100 mL). The combined extracts were washed with water and brine, and dried over magnesium sulfate. The solvent was removed in vacuo to afford quantitative yield of tert-butyldimethylsilyl 4-((tert-butyldimethylsilyl)oxy)benzoate (5.4 g).

Tert-butyldimethylsilyl 4-((tert-butyldimethylsilyl)oxy) benzoate (5.6 g, 15.3 mmol, crude) in 20 mL of dry dichloromethane containing a few drops of DMF was treated with oxalyl chloride (2.5 g, 19.9 mmol). The resulting mixture was stirred at rt for 2 days. The solvents were removed in vacuo and the crude acyl chloride was used in the next step. The solution of the crude acyl chloride (15.3 mmol) in dry dichloromethane (20 mL) was added dropwise to a cooled (0° C.) solution of 2-hydroxypyridine (1.21 g, 12.7 mmol), DMAP (156 mg, 1.3 mmol), and pyridine (3 mL) in dichloromethane (20 mL). After the addition was completed, the mixture was allowed to warm up to rt overnight. EtOAc (150 mL) was added to the mixture and the organic layer was washed with water, brine, and dried over magnesium sulfate. Concentration under reduced pressure gave the crude product which was purified by column chromatography. Elution with 10% EtOAc in hexane afforded 3.52 g (69%) of the silyl protected ester.

The silyl protected ester (1.02 g, 3.1 mmol) was dissolved in dry THF (20 mL) and the solution was cooled to 0° C. Tetrabutylammonium fluoride (3.7 mL, 1 M solution in THF) was added dropwise to the above solution and the resulting mixture was stirred at 0-5° C. for 45 minutes. The reaction was then quenched with saturated ammonium chloride and the product extracted with EtOAc (3×100 mL). The combined organic extracts were washed with water and brine, and dried over magnesium sulfate. Solvents were removed in vacuo and the crude product was purified by column chromatography using MeOH in dichloromethane (2-10%). Further purification by recrystallization from EtOAc/hexane afforded 546 mg (82%) of 4-hydroxy-benzoic acid pyridin-2-yl ester. MS (ES) m/z: 216.08 (M+1), and 121.00; $^{13}$C-NMR (CD$_3$OD): δ 164.85, 163.40, 158.57, 147.95, 140.46, 132.50, 122.37, 119.61, 117.24, and 115.37.

Example 21

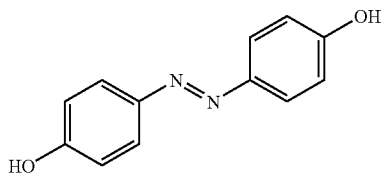

4-(4-Hydroxy-phenyl)-azophenol

In a 250 mL round-bottomed flask fitted with condenser and magnetic stirrer were placed 4-amino phenol (1.0 g, 9.16 mmol) and toluene (100 mL). Solid KO$_2$ was added (2.0 g, 28.1 mmol). Then the reaction mixture was stirred for 48 h at rt under nitrogen. The residual KO$_2$ was destroyed by cautious addition of water. The reaction mixture was acidified by 2 N HCl and extracted with EtOAc. The organic layer was washed with water, dried and concentrated to give a crude product, which was purified by column chromatography using 50% EtOAc in hexane to a give 160 mg of 4-(4-Hydroxy-phenyl)-azophenol (8%). MS (ES) m/z: 215.05 (M+1).

Example 22

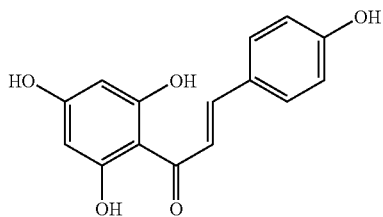

(E)-3-(4-Hydroxy-phenyl)-1-(2,4,6-trihydroxy-phenyl)-propenone

In a 50 mL three neck round bottom flask fitted with a condenser, naringenine (0.5 g, 1.83 mmol), NaOH (0.59 g, 14.68 mmol, 5% aqueous solution) and MeOH (20 mL) were taken. The reaction mixture was refluxed for 2 h. then poured into excess of 2N HCl solution. The product was extracted with EtOAc. The organic layer was washed with water, brine and dried over Na$_2$SO$_4$. The solvent was removed to give crude product, which was purified by column chromatography using 30% EtOAc in hexane to give 150 mg of (E)-3-(4-hydroxy-phenyl)-1-(2,4,6-trihydroxy-phenyl)-propenone (58%). MS (ES) m/z: 273.11 (M+1).

Example 23

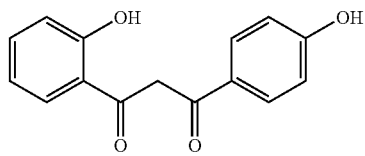

1-(4-Hydroxy-phenyl)-3-(2-hydroxy-phenyl)-propane-1,3-dione

In a 50 mL round-bottomed flask fitted with condenser and magnetic stirrer were placed 4-hydroxybenzoic acid (1.50 g, 10.86 mmol), Ac$_2$O (1.33 g, 13.03 mmol), Et$_3$N (1.318 g, 13.03 mmol) and catalytic amount of DMAP. The reaction mixture was stirred for 24 h at rt. The reaction mixture was poured into water and extracted with EtOAc. The organic layer was washed with water, dried and concentrated to give the 4-O-acetyl benzoic acid (1.66 g, 85%).

To a 100 mL round-bottomed flask fitted with condenser and magnetic stirrer were placed 2'-hydroxyacetophenone (1.25 g, 9.16 mmol), 4-O-acetylbenzoic acid (4.0 g, 9.16 mmol) and pyridine (25 mL). POCl$_3$ (1.4 g, 9.16 mmol) was added slowly on cooling. The reaction mixture was stirred for 24 h at rt under nitrogen. The reaction mixture was poured into ice water and extracted with EtOAc. The organic layer was washed with water, dried and concentrated to give product (1.7 g, 85%). To the product (1.7 g, 5.69 mmol) in THF (30 mL) was added a potassium t-butoxide (0.836 g, 6.83 mmol) and the reaction mixture was stirred for 24 h at rt under N$_2$. The reaction mixture was poured into saturated aqueous solution of NH$_4$Cl. The organic layer was separated, washed with water, dried and concentrated to give the crude product. Purification by column chromatography using 20% EtOAc in hexane to give 200 mg of product (14%).

MS (ES) m/z: 257.08 (M+1).

Example 24

ApoA-I Promoter Induction in Caco-2 Intestinal Cells

To examine the effects of compounds of the invention to increase ApoA-I expression, Caco-2 cells, an intestinal cell line derived from human epithelial intestinal cells were, grown under conditions recommended by the ATCC and summarized in United States Patent Application Publication 20040033480 ("Wong"), incorporated herein by reference. Wong demonstrated that resveratrol increases ApoA-I promoter activity by 2.5-times over untreated control. This study similarly demonstrated that compounds of the present invention induced ApoA-I promoter activity.

Briefly, the promoter region of the gene encoding human ApoA-I was isolated and ligated upstream of the firefly luciferase gene to construct the reporter plasmid pAI.474-Luc. This reporter plasmid and pRSV-β-galactosidase (as a control for transfection efficiency) were co-transfected to Caco-2 cells. The Caco-2 cells were then incubated in a MEM selection media containing 20% fetal calf serum supplemented with G418 (final concentration: 0.5 mg/mL, Gibco) to give established strains that stably express from the reporter gene. The strains were seeded in 6-well culture plates and incubated for 48 hours at 37° C. under 5% carbon dioxide. Cells were starved for 24 hrs in MEM selection media containing 0.5% FBS. Then, a solution of a compound of the inyention in DMSO or other appropriate solvent was added to the wells at a final concentration of 0 to 100 µM in MEM selection media containing 0.5% FBS.

After further incubation for 48 hours, the cells were harvested and lysed using Reporter Lysis Buffer (PROMEGA E3971) and 50 µL of luciferase assay reagent (PROMEGA E4550 Luciferase Reporter 1000 assay system) was added to measure luciferase activity with a luminometer (Fluoroskan Ascent FL from Thermo electron Corporation). Measures of luciferase activity were normalized to lysate protein concentrations, measured using Bradford Reagent (BioRad Protein Assay reagent Cat#500-0006). The luciferase activity of cells treated with various concentrations of test compounds was compared to that of control sample (i.e., solvent without any compound of the present invention added) and untreated samples. An increase in luciferase activity compared to untreated and or control samples indicates that the compound of the invention increases the expression of ApoA-I. cells. The results provided in Table 2 are based on average values at 15 µM concentrations.

TABLE 2

Induction of ApoA-I Promoter in Caco-2 Intestinal Cells

| Compound | ApoA-I Promoter Induction |
|---|---|
| Resveratrol (Example 1) | increased |
| 4,4'-dihydroxy-stilbene | increased |
| 4-(4-Hydroxy-phenyl)-azophenol (Example 21) | increased |
| 4-[4-Hydroxy-phenethyl]-phenol (Example 17) | increased |
| 5-[(E)-2-(4-Hydroxy-phenyl)-vinyl]-pyridin-2-ol (Example 2) | increased |
| 4-[(E)-2-(4-Hydroxy-phenyl)-vinyl]-3-methoxy-phenol (Example 3) | increased |
| 3-Hydroxymethyl-4-[(E)-2-(4-hydroxy-phenyl)-vinyl]-phenol (Example 4) | increased |
| 2-Hydroxy-5-[(E)-2-(4-hydroxyphenyl)vinyl]benzoic acid (Example 5) | no increase |
| 4-Hydroxy-N-(4-hydroxyphenyl)-benzenesulfonamide (Example 19) | increased |
| 3-Nitro-4-[(E)-2-(4-hydroxyphenyl)-vinyl]phenol (Example 6) | increased |
| (E)-Ethyl 2-hydroxy-5-(4-hydroxystyryl) benzoate (Example 7) | increased |
| 3-Amino-4-[(E)-2-(4-hydroxy-phenyl)vinyl]phenol (Example 10) | increased |
| (E)-2-Hydroxy-5-(4-hydroxystyryl)benzamide (Example 8) | increased |
| N-oxide 4'-hydroxystilbene hydrochloride (Example 13) | increased |
| 5-Hydroxy-2-[2-(4-hydroxyphenyl)vinyl]-N,N-dimethyl-benzamide (Example 12) | increased |
| 4-Hydroxy-chalcone | increased |
| 4-Methoxy-chalcone | increased |
| 4,2',4'-Trihydroxy-chalcone | increased |
| 2,4-Dihydroxy-4'-methoxy-chalcone | increased |
| 4,2',4',6'-Tetramethoxy-chalcone | increased |

Example 25

Kinetics of ApoA-I Promoter Induction

Whereas the preceding studies showed that the compounds of the invention stimulate ApoA-I promoter activity, the duration of action was unclear. Accordingly, the kinetics of induction of the ApoA-I promoter can be assessed as follows.

Caco-2 cells transfected with pAI.474-Luc are treated with compounds of the invention at selected time points varying from 4 to 72 hours. pAI.474-Luc contains the human ApoA-I promoter fused to the reporter gene, firefly luciferase (Luc). Wong demonstrated that when the test compound is resveratrol a significant stimulation of ApoA-I promoter activity in Caco-2 cells was observed at 4, 8, 16 and 24 hours following administration, but maximal stimulation was observed following 16 hours of exposure.

Example 26

Confirmation of ApoA-I Induction in Caco-2 Intestinal Cells

This experiment will measure the ability of a test compound to stimulate transcriptional activity of the endogenous Apo-A1 promoter in the Caco-2 cells. Such simulation will result in an increase in expression of ApoA-I protein, which is ultimately responsible for antiatherogenic activity. A test compound, which has demonstrated an increase in the activity of the ApoA-I promoter in the pAI.474-Luc construct may be tested in this assay to confirm its effect on the activity of the ApoA-I gene endogenous to the Caco-2 cells. The Caco-2 cells are cultured as described in Wong and exposed to media containing test compound at a concentration of 5, 7.5, 10, 15 or 20 µM for 24 or 48 hours. Longer exposure of the cells to the test compound is utilized to allow adequate time for the ApoA-I protein to be secreted into the media from the Caco-2 cells, and detected. Conditioned media exposed to the cells for 24 or 48 hours is assayed for its content of ApoA-I protein using Western blot analysis or enzyme-linked immunoassay (ELISA).

Results should show an increase in the amount of ApoA-I protein in the conditioned media from cells treated with test compound as compared to untreated cells. The results of these studies will demonstrate that a test compound augments expression of the ApoA-I gene, are therefore, antiatherogenic. Increased expression of the ApoA-I gene augments reverse cholesterol transport and thereby facilitates the removal of cholesterol from the body.

Example 27

ApoA-I Promoter Induction in HepG2 Liver Cells

This study determined whether compounds of the invention have an effect on ApoA-I promoter activity expression in HepG2 cells, a liver cell line. Cells were grown under conditions recommended by the ATCC and summarized by Wong.

The promoter region of the gene encoding human ApoA-I was isolated and ligated upstream the structure gene of firefly luciferase to construct a reporter plasmid (pAI.474-Luc). The reporter plasmid, along with pRSV-β-galactosidase (as a control for transfection efficiency) were co-transfected into HepG2 cells. The cells were then incubated in an MEM selection medium containing 20% fetal calf serum supplemented with G418 (final concentration: 0.5 mg/mL, Gibco) to give established strains that stably express from the reporter gene. The strains were seeded to a 6-well culture plates and incubated for 48 hours at 37° C. under 5% carbon dioxide. Cells were starved for 24 hrs in MEM selection media containing 0.5% FBS. Then, a solution of the compounds of the invention in DMSO (or other appropriate solvent) was added to the wells at a final concentration of 0 to 100 µM in MEM selection media containing 0.5% FBS.

After further incubation for 48 hours, the cells were harvested and lysed using Reporter Lysis Buffer (PROMEGA E3971), and 50 μL of luciferase assay reagent (PROMEGA E4550 Luciferase Reporter 1000 assay system) were added to measure luciferase activity with a luminometer (Fluoroskan Ascent FL from Thermo electron Corporation). Measures of luciferase activity were normalized to lysate protein concentrations, measured using Bradford Reagent (Biorad Protein Assay reagent Cat#500-0006). An increase in luciferase activity compared to untreated and or control samples indicates that the compound of the invention increased the expression of ApoA-I. The results provided in Table 3 are based on average values at 15 μM concentrations.

TABLE 3

Induction of ApoA-I Promoter in HepG2 liver cells

| Compound | ApoA-I Promoter Induction |
| --- | --- |
| Resveratrol (Example 1) | increased |
| 4-[4-Hydroxy-phenethyl]-phenol (Example 17) | increased |
| 4-[(E)-2-(4-Hydroxy-phenyl)-vinyl]-3-methoxy-phenol (Example 3) | increased |
| 3-Nitro-4-[(E)-2-(4-hydroxyphenyl)-vinyl]phenol (Example 6) | increased |
| 4,4'-dihydroxy-stilbene | increased |

Example 28

ApoA-I Protein Expression in HepG2 Cells

This study will confirm that compounds of the invention have an effect on ApoA-I protein secretion in HepG2 (liver) cells by measuring whether stimulation of transcriptional activity of the promoter in the HepG2 cells increased the abundance and secretion of ApoA-I protein.

The HepG2 cell line is obtained from the ATCC and cultured in MEM media supplemented with 10% FBS (Gibco), with 1 mM sodium pyruvate, 0.1 mM MEM non-essential amino acid, 2 mM L-glutamine, 100 U/ml penicillin, 100 μg/ml streptomycin and 5 μg/ml plasmocin. Cells are maintained at 37° C. in an atmosphere of 5% $CO_2$ Cells should be grown to 85% confluency prior to initiating the experiment.

Cells are plated and allowed to adhere overnight in a phenol red-free DMEM containing 10% of Charcoal/Dextran treated FBS (Hyclone), with 1 mM sodium pyruvate, 0.1 mM MEM non-essential amino acid, 2 mM L-glutamine, 100 U/ml penicillin, 100 μg/mi streptomycin and 5 μg/ml plasmocin. The medium is removed, and cells are washed in 1×PBS. Cells are then starved in phenol red-free DMEM (serum free) for a period of 24 hours. Cells are then mock treated (untreated, DMSO), or treated with compound of the invention diluted in phenol red-free DMEM (serum free) media at a concentration of 7.5 μM. Cells and media are harvested at 0, 6 and 24 hours following compound treatment.

Medium removed from cells may be applied to a solid phase capture sandwich in an ELISA assay according to manufacture's instructions such as Total human Apolipprotein ELISA Assay-Alercheck.

Compounds of the invention activate promoter activity for ApoA-I, leading to an increase in transcription, as demonstrated in Example 24 and 27 and increase in synthesis of ApoA-I, as may be demonstrated following the procedures set forth in this Example. Thus, the compounds of the invention and pharmaceutically acceptable salts or hydrates thereof, can be expected to elevate promoter activity and ApoA-I protein levels, in intestinal and liver cells and are useful for elevating plasma ApoA-I levels in a patient to whom the compound is administered.

Example 29

Solubility Analysis

To evaluate the solubility of compounds of the invention, 1 mg of compound is added to 1 mL of PBS and sonicated for 1 hour at room temperature using the Branson 3210 Sonicator in triplicate and incubated in a water bath at 25° C. for 3 hrs. Samples are then centrifuged at 14,000 rpm for 6 minutes at room temperature. The supernatant is diluted with acetonitrile and is removed for analysis. Analysis may be performed using HPLV-UV with 7 point standard curve to determine the concentration. The average concentration calculated is regarded as the solubility (μM). See e.g., Ng, et al., "Evaluation of the first-pass gluceronidation of select flavones in the gut by Caco-2 monolayer model," *J. Pharm. Pharmaceut. Sci.* 8(1):1-9 (2005).

These experiments are expected to indicate that the solubility of compounds of the invention are better than naturally occurring polyphenols, such as apigenin with a solubility of 3.27 μM. The poor bioavailability of naturally occurring polyphenols is partially attributed to poor solubility. As such, solubility is unlikely to affect the validity of any in vitro tests performed on the compounds of the invention, and formulation of these compounds for in vivo work should not be technically difficult to one skilled in the art. Accordingly, the compounds of the invention and pharmaceutically acceptable derivatives thereof, are suitable for human use due to the unexpected utility of improved solubility.

Example 30

Caco-2 Permeability

The Caco-2 cell drug transport model is widely used for screening compounds in drug discovery to assess intestinal transport and predict absorption rates. For example, the fraction of drug absorbed in human could be determined by in vivo human permeability or predicted by in vitro Caco-2 permeability; if compound permeability in Caco-2 cells reaches $13.3-18.1 \times 10^{-6}$ cm/s, its predicted in vivo permeability in humans would reach $2 \times 10^{-4}$ cm/s, and the predicted fraction of drug absorbed would be >90%, which is defined as highly permeable. Sun et al., "In vitro testing of drug absorption for drug 'developability' assessment: forming an interface between in vitro preclinical data and clinical outcome," *Curr. Opin. Drug Discov. Devel.* 7(1):75-85 (2004). Therefore, in vitro absorption testing is a highly valuable tool for comparison of structural analogues for improved intestinal absorption, and to identify compounds within the decision-making for clinical studies at early-stage drug discovery and development.

The method of Hai-Zhi et al., "High-throughput Caco-2 cell permeability screening by cassette dosing and sample pooling approaches using direct injection/on-line guard cartridge extraction/tandem mass spectrometry," *Rapid Communications in Mass Spectrometry* 14:523-528 (2000) may be used with obvious modifications to someone skilled in the art. Table 4 shows the results of permeability of representative compounds of the invention in an in vitro Caco-2 intestinal transport model over time as compared to resveratrol.

TABLE 4

| Compound | % Transported Paap (cm/s) |
| --- | --- |
| Propanol | $1.01 \times 10^{-5}$ |
| (E)-4,4'-(diazene-1,2-diyl)diphenol (Example 21) | $8.73 \times 10^{-6}$ |
| Resveratrol (Example 1) | $3.34 \times 10^{-6}$ |
| 4-Hydroxy-benzoic acid pyridin-2-yl ester (Example 20) | $2.00 \times 10^{-6}$ |
| 3-nitro-4-[(E)-2-(4-hydroxy-phenyl)-vinyl]-phenol (Example 6) | $1.95 \times 10^{-6}$ |
| 3-Hydroxymethyl-4-[(E)-2-(4-hydroxy-phenyl)-vinyl]-phenol (Example 4) | $1.79 \times 10^{-6}$ |

These experiments indicate that the permeability of representative compounds of the invention and particularly, (E)-4,4'-(diazene-1,2-diyl)diphenol (Exampel 21), are equivalent to or greater than naturally occurring polyphenols, such as or resveratrol with a permeability $3.34 \times 10^{-6}$. Accordingly, the compounds of the invention and pharmaceutically acceptable salts and hydrates thereof, are potentially suitable for human use due to the permeability of intestinal cells to these compounds.

Example 31

Transgenic Mice

To confirm that the efficacy of compounds of the invention observed in vitro extends to an in vivo model, transgenic mice carrying multiple copies of the human ApoA-I gene (C57BI/6-tgn(apoa1)1 rub, Jackson Laboratory, Bar Harbor, Me.) are exposed to compounds of the invention. The exogenous human ApoA-I gene in these mice enables them to express the human ApoA-I protein under the control of this promoter.

Seven to eight week old male mice, transgenic for human ApoA-I are individually identified by numbering on tail and weighed. Mice aare pre bleed via the retro-orbital plexus and 150 µl of blood was collected in 1.5 ml Eppendorf tube containing 1 µl of heparin and chilled on ice. Plasma is collected after centrifuging the whole blood at 14000 rpm (TOMY highspeed microrefrigerated centrifuge NTX-150) for 10 minutes at 4° C. and frozen at −80° C. Plasma is analyzed for: human ApoA1 by a human ApoAI enzyme-linked Immunoassay (Direct Sandwich ELISA Calbiochem Cat#178422, Calbiochem Cat#178452, lot #B9076, Calbiochem Cat #178470 conjugated to Horse Radish Peroxidase (Cedarlane Cat#80220)); total cholesterol (Ponte scientific reagents: #C7509-STD, #L7580-18, #C7510); triglyceride (Pointe Scientific Reagents: #7532-STD, #L7580-18, #7532). All samples are measured in triplicates and expressed as mg/dl. Mice are grouped based on plasma parameters and average body weight.

Two days following pre-bleed, mice are dosed by oral gavage daily for 14 days using a 20 gauge, 11/2" curved disposable feeding needle [Popper & Sons]; when BID, mice are gavaged morning and afternoon (8 am and 5 pm); when SID, mice are gavaged in morning (8 am). Compounds are prepared each day in vehicle. Test article(s), a positive control, such as, fenofibrate, and vehicle are dosed at volume of 5 mL/kg of body weight as a suspension (0.1 mL/20 g mouse). Fenofibrate may be obtained commercially (SIGMA F 6020). Mice weights will be recorded on day 1, 4, 7, 10, 12, and 15. On day 15, mice are weighed and fasted for 4 hours, sacrificed by inhalation of $CO_2$ and blood is obtained via cardiac puncture (0.7-1.0 ml). Plasma is collected and frozen at −80° C. Samples are assayed for ApoA-I, total cholesterol, triglyceride and HDL-C by HPLC [Polaris 200 with an auto sampler Prostar 410 from Varian on a Superose 6 10/30 column from Amersham]. Samples are sent for NMR analysis [Lipo-Science] to identify particle size and subclass for lipoproteins. During necropsy, liver, brown fat, and the whole of small and large intestines were collected, cleaned with cold PBS and frozen at −80° C. for further analysis of compound levels.

One adverse effect of fenofibrate treatment is liver weight gain, largely due to increased hepatic peroxisome proliferation. Compounds of the invention are expected to show reduced liver weight gain possibly because they do not act as peroxisomal proliferator activator receptor alpha ligands. This would indicate that the compounds of the invention are useful for increasing plasma ApoA-I and elevating circulating HDL, without the adverse side effect associated with liver weight gain in a patient to whom the compound is administered.

Example 32

Measurement of AGCCCCCGC Sequence Element Induction

Caco-2 or HepG2 cells are exposed to effective concentrations of compounds of the invention. The cells are first transfected using standard techniques with a reporter construct comprising one or more copies of the nine nucleotides, 5'-AGCCCCCGC-3' acting as an enhancer element (Kilbourne et al., J. Biol. Chem. 270:7004 (1995)), operably linked to a promoter (for example the thymidine kinase (TK) promoter), operably linked to a reporter gene (for example luciferase, CAT, or the ApoA-I gene) along with pRSV-β-galactosidase, which monitors transfection efficiency (as taught in Wong). Compounds of the invention are then dissolved in appropriate solvent (for example, DMSO) and then added to the culture media for 16 hours. At the end of the treatment, the cells are harvested, and the reporter gene activity is measured using standard assays. Increased or decreased reporter gene activity indicates that compounds of the invention have the ability to modulate transcription from promoters that contain the nine nucleotide sequence 5'-AGCCCCCGC-3', which is believed to comprise an egr-1 responsive element.

Example 33

Measurement of Antioxidant Effectiveness

The antioxidant performance of compounds of the invention is demonstrated by measuring the extent of low density lipoprotein hydroxyperoxide by copper catalyzed autoxidation using a published dye based color assay. FOX Assay, Zadeh, Methods in Enzymology, 300:58 (1999). Samples containing only LDL and copper sulfate without test materials, serve as a positive control for comparison with identical mixtures containing test materials.

Human Low Density Lipoprotein (Sigma Chemical Company L2139) in phosphate buffered saline pH 7.4 is mixed with copper sulfate. Incubation with effective a mounts of compounds of the invention at 25° C. or 37° C. open to air effects oxidation, and the mixture is sampled at time zero and between 3 and 20 hours of incubation for measurement of hydroperoxide in the FOX assay. Samples are read in a microtitre plate reader. Decreased hydroperoxide as measured by the FOX assay reveals the anti-oxidant activity of compounds of the invention and their usefulness for the treatment or prevention of disorders, diseases or conditions associated with oxidation or benefiting from the administration of anti-oxidants. An example of such a condition that would benefit from the treatment of anti-oxidants is cardiovascular disease.

Example 34

Measurement of Antioxidant Activity by LDL Oxidation Assay

The method of Esterbauer et al., *Free Radic. Res. Commun.* 6:67 (1989) may be used, with some modification as follows: the compound is dissolved with an appropriate solubilizing agent in a phosphate buffer solution (PBS, 0.15 M NaCl-0.05 M Na Phosphate Buffer-pH 7.4). The exact concentration is noted (approximately 30-60 µL/mL of extract to be measured). To 100 µL of this solution is added to 900 µL of an oxidizing buffer (made from human LDL, 120 µL of 5 mg/mL solution with d=1.019-1.063 g/mL, purchased from PerImmune, Rockville, Md.) and copper sulfate (20 µL of 10 mM aqueous solution) in 8 mL PBS). A blank sample made with 100 µL PBS and 900 µL oxidizing buffer is also prepared. Each solution is then transferred to a 1 cm quartz cuvette, and the cuvette is placed into thermostat (37° C.). An HP-8452A Diode Array Spectrophotometer measures optical density at 234 nm (OD sub 234), making a measurement every 5 minutes. The lag time for oxidation is calculated as the maximum of the first derivative of the optical density curve. A standard containing ascorbic acid is run with each assay.

Example 35

Effects on LDL-Cholesterol, HDL-Cholesterol and Triglyceride Levels in Male Sprague-Dawley Rats Compounds of the invention are administered daily at a dose of 100 mg/kg to chow fed male Sprague-Dawley rats for seven days in the morning by oral gavage in 1.5% carboxymethylcellulose/0.2% Tween-20 (dosing vehicle). Animals are weighed daily. Animals are allowed free access to rodent chow and water throughout the study. After the seventh dose, animals are sacrificed in the evening and blood serum is assayed for lipoprotein cholesterol profiles, serum triglycerides, total cholesterol VLDL, LDL, and HDL cholesterol, and the ratio of HDL cholesterol to that of VLDL plus LDL cholesterol, apolipoproteins AI, C-II, C-III, and E by immunoelectrophoresis, and percent weight gain.

Blood serum is assayed for total cholesterol and triglycerides, lipoprotein cholesterol profiles, VLDL plus LDL cholesterol combined (also referred to as Apo B containing lipoprotein cholesterol or non-HDL cholesterol), HDL cholesterol, and the ratio of HDL cholesterol to that of VLDL plus LDL cholesterol, serum glucose, and non-esterified fatty acids, and percent weight gain.

Example 36

Effects on LDL-Cholesterol, HDL-Cholesterol and Triglyceride Levels in Obese Female Zucker Rats Compounds of the invention and troglitazone are administered daily at various doses to 10-week old chow fed obese female Zucker rats for 14 days in the morning by oral gavage in 1.5% carboxymethylcellulose/0.2% Tween-20 (dosing vehicle). Animals are weighed daily. Animals are allowed free access to rodent chow and water throughout the study. Blood glucose is determined after a 6-hour fast in the afternoon without anesthesia from a tail vein. Serum is also prepared from a blood sample subsequently obtained from the orbital venous plexus (with $O_2/CO_2$ anesthesia) prior to and after one week treatment and used lipid and insulin determinations. At two weeks, blood glucose is again determined after a 6-hour fast without anesthesia from a tail vein. Soon thereafter, animals are sacrificed by $CO_2$ inhalation in the evening and cardiac blood serum is collected and assessed for various lipids and insulin. Body weight is determined daily prior to dosing and at the time of euthanasia.

Blood serum is assayed for serum non-HDL cholesterol, HDL-cholesterol, triglyceride and body weight (relative to pretreatment values) in fasted (6 hours) chow-fed obese female Zucker rats. Blood glucose and serum insulin levels are determined from fasted rats just prior to and following one and two weeks of treatment. Blood glucose is maintained at slightly elevated levels for 10-12 week old obese Zucker rats during treatment with all doses, with the exception of the doses, whereby the compounds show a tendency to lower blood glucose. Percent liver to body weight is determined after two weeks of treatment at the time of sacrifice.

Example 37

Effects on Lipoprotein Cholesterol Profile in LDL Receptor-Deficient Mice

Homozygous familial hypercholesterolemia is a rare human disease (affecting about $1/1,000,000$) characterized by absent or defective LDL receptors, markedly elevated serum LDL cholesterol levels and very early and severe onset of atherosclerosis. The more common form of this disease in humans, heterozygous familial hypercholesterolemia, occurs in about one in every 500 humans. Patients with the heterozygous form of this disease also present with elevated LDL levels and early onset of atherosclerosis.

The effect of the compounds of the invention on LDL levels in a murine model of homozygous familial hypercholesterolemia (Ishibashi et al., *J. Clin. Invest.* 92:883 (1993); Ishibashi et al., *J. Clin. Invest.* 93:1885 (1994)) is studied. LDL receptor-deficient mice have elevated LDL cholesterol relative to wild type mice when fed a chow diet. When fed cholesterol-enriched diets, these mice develop atherosclerosis.

Example 38

Effect on Synthesis of Non-Saponified and Saponified Lipids in Hepatocytes Isolated from Male Sprague-Dawley Rats A male Sprague-Dawley rat is anesthetized by administration of sodium pentobarbitol by intraparitoneal injection at 50 mg/kg. In situ perfusion of the liver is performed as follows. The abdomen of the animal was opened, the portal vein canulated, and the liver perfused with WOSH solution (149 mM NaCl, 9.2 mM Na HEPES, 1.7 mM fructose, 0.5 mM EGTA, 0.029 mM phenol red, 10 U/ml heparin, pH 7.5) at a flow rate of 30 ml/min for 6 minutes. To digest the liver, DSC solution (6.7 mM KCl, 143 mM NaCl, 9.2 mM Na HEPES, 5 mM $CaCl_2$—$2H_2O$, 1.7 mM fructose, 0.029 mM Phenol red, 0.2% BSA, 1.00 U/mi collagenase Type I, 93 U/ml hyaluronidase, 160 BAEE/ml trypsin inhibitor, pH 7.5) is perfused through the liver at a flow rate of 30 ml/min for 6 minutes at a temperature of 37° C. After digestion, cells are dispersed in a solution of DMEM containing 2 mM GlutMax-1, 0.2% BSA, 5% FBS, 12 nM insulin, 1.2 µM hydrocortisone to stop the digestion process. The crude cell suspension is filtered through three layers of stainless steel mesh with pore sizes of 250, 106, and 75 µm respectively. Filtered cells are centrifuged at 50×g for two minutes and the supernatant discarded. The resulting cell pellet is resuspended in DMEM and centrifuged again. This final cell pellet is resuspended in DMEM+HS solution (DMEM containing 2 mM GlutMax-1, 20 nM delta-aminolevulinic acid, 17.4 mM MEM non-essential amino acids, 20% FBS, 12 nM insulin, 1.2 µM hydrocortisone) and plated to form monolayer cultures at a density of $100 \times 10^3$ cells/cm$^2$ on collagen coated culture dishes. Four hours after initial plating, media is changed to DMEM+ (DMEM containing 2 mM GlutMax-1, 20 nM delta-aminolevulinic acid, 17.4 mM MEM non-essential amino acids, 10% FBS, 12 nM insulin, 1.2 µM hydrocortisone) and remained on cells overnight.

To test the effect of compounds of the invention on synthesis rates of non-saponified and saponified lipids, the monolayer cultures are exposed to 1 µM of lovastatin or 100 µM of test compound in DMEM+containing 1 µCi/ml $^{14}$C-acetate. Control cells are exposed to the same media lacking lovastatin or the test compounds. All are exposed to 0.1% DMSO. Metabolic labeling with $^{14}$C-acetate continued for 2 hr at 37° C. After labeling, cells are washed twice with 1 ml of PBS followed by lysing in 1 ml of deionized water. Cells are scraped from the dishes, transferred to glass tubes and sonicated. 2.5 ml of 2:1 chloroform/methanol mixture was added followed by 1.5 ml of Phosphate Buffered Saline (PBS). To correct for extraction efficiency in the upcoming extractions, 3000 dpm of $^3$H-cholesterol was added to each tube. Tubes are shaken for 30 min. to extract lipids into the organic phase followed by centrifugation for 10 minutes at 1000×g to separate the organic and aqueous phases. The lower organic phase containing total lipids is removed and placed in a new tube. The organic solution is evaporated under $N_2$. The dry lipid extract was resuspended in 1 ml of 93% ethanol containing 1 M KOH and placed at 70° C. for 2.5 hours. After the reaction and cooling, 2 ml of hexane and 2.5 ml of water is added to each tube followed by rigorous shaking for 10 min. Tubes are centrifuged for 10 min. at 1000×g and the organic (top) layer containing the non-saponified lipids is transferred to a new tube followed by evaporation of the organic solvent under $N_2$. The aqueous phase containing the saponified lipids is also transferred to a new tube. The non-saponified lipid extract, after drying, is resuspended in toluene and an aliquot of the suspension is added to a scintillation cocktail for radioactive counting. The number of $^{14}$C counts representing the incorporation of $^{14}$C-acetate into non-saponified lipids is corrected for extraction efficiency, based on the recovery of $^3$H counts extracted. To isolate saponified lipids, 1.5 ml of aqueous phase solution is mixed with 400 µl of 1 M HCl, and then lipids are extracted by the addition of 2.5 ml of 2:1 chloroform:methanol, 1.5 ml of PBS, and 1 ml of water followed by rigorous shaking and isolation of the organic phase. The organic phase from this extraction is evaporated under $N_2$ and resuspended in toluene. Its radioactivity is counted using scintillant to provide the rate of $^{14}$C-acetate incorporation into saponified lipid.

Example 39

Measurement and Comparison of HDL, LDL, VLDL and Triglyceride Levels in Humans

Compounds of the invention are administered daily to human subjects. Other dietary uptake is monitored and held constant between individuals. Blood samples are taken on the day 0, prior to commencing the administration of the compounds, and once weekly for 3 to 6 months. Blood serum is assayed for total cholesterol and triglycerides, lipoprotein cholesterol profiles, VLDL plus LDL cholesterol combined (also referred to as ApoB containing lipoprotein cholesterol or non-HDL cholesterol), HDL cholesterol, HDL$_2$ and HDL$_3$ cholesterol fractions, and the ratio of HDL cholesterol to that of VLDL plus LDL cholesterol, utilizing standard, commercially available cholesterol tests, such as the VAP test (Atherotech Inc, Birmingham, Ala.) which can reproducibly measure these parameters from a small sample of human blood. Alternatively, HDL$_2$ and HDL$_3$ can be measured from blood by the method of Kulkarni et al., *J. Lipid Res.* 38:2353 (1997) or by the method of Gidez et al., *J. Lipid Res.* 23:1206 (1982). Compounds of the invention which increase total HDL, increase HDL$_2$, decrease total LDL, decrease VLDL, decrease triglyceride, or increase the HDL/total cholesterol or HDL/LDL ratios as determined in such a blood test are useful for the treatment of cholesterol or lipid associated disorders.

Example 40

Measurement of Atherosclerotic Lesion Size Using Proteoglycan-Binding-Defective LDL A nucleic acid construct may be used to generate mice expressing a proteoglycan-binding-defective LDL. The transgenic mice are fed a diet containing 1.2% cholesterol, 0.5% bile salts, and 20% fat for 17 weeks. The mice are then sacrificed, and the aortas are perfusion fixed and analyzed with the en face procedure, in which the entire aorta is pinned out flat, stained with Sudan IV, and analyzed with a morphometric image-analysis system (Image-1/AT) to quantitate the extent of atherosclerosis.

Example 41

Determination of ACAT Inhibition

The activity of compounds of the invention as inhibitors of ACAT may be determined by known methods, for example, those taught in U.S. Pat. No. 6,165,984, incorporated herein by reference and summarized below.

First, rats are sacrificed by decapitation and the livers excised. 1 g of each of the livers is homogenized in 5 ml of homogenization medium (0.1 M KH$_2$PO$_4$, pH 7.4, 0.1 mM EDTA and 10 mM β-mercaptoethanol). The homogenate is centrifuged at 3,000×g for 10 min. at 4° C. and the supernatant thus obtained is centrifuged at 15,000×g for 15 min. at 4° C. to obtain a supernatant. The supernatant is put into an ultracentrifuge tube (Beckman) and centrifuged at 100,000×g for 1 hour at 4° C. to obtain microsomal pellets, which are then suspended in 3 ml of the homogenization medium and centrifuged at 100,000×g for 1 hour at 4° C. The pellets thus obtained are suspended in 1 ml of the homogenization medium. The concentration of proteins in the resulting suspension is determined by Lowry's method and then adjusted to 4 to 8 mg/ml. The resulting suspension is stored in a deep freezer (Biofreezer, Forma Scientific Inc.).

6.67 µl of 1 mg/ml cholesterol solution in acetone is mixed with 6 µl of 10% Triton WR-1339 (Sigma Co.) in acetone and, then, acetone is removed from the mixture by evaporation using nitrogen gas. Distilled water is added to the resulting mixture in an amount to adjust the concentration of cholesterol to 30 mg/ml. To 10 µl of the resulting aqueous cholesterol solution is added 10 µl of 1 M KH$_2$PO$_4$ (pH 7.4), 5 µl of 0.6 mM bovine serum albumin (BSA), 10 µl of microsome solution obtained in (Step 1) and 55 µl of distilled water (total 90 µl). The mixture is pre-incubated in a waterbath at 37° C. for 30 min.

10 µl of (1-$^{14}$C) oleoyl-CoA solution (0.05 µCi, final concentration: 10 µM) is added to the pre-incubated mixture and the resulting mixture is incubated in a waterbath at 37° C. for 30 min. To the mixture is added 500 µl of isopropanol:heptane mixture (4:1(v/v)) 300 µl of heptane and 200 µl of 0.1 M KH$_2$PO$_4$ (pH 7.4), and the mixture is mixed violently by using a vortex and then allowed to stand at a room temperature for 2 min. 200 µl of the resulting supernatant is put in a scintillation bottle and 4 ml of scintillation fluid (Lumac) is added thereto. The mixture is assayed for radioactivity with liquid scintillation counter. ACAT activity is calculated as picomoles of cholesteryl oleate synthesized per min. per mg protein (pmoles/min/mg protein).

Example 42

Determination of Inhibition of HMG-CoA Reductase

The potency of inhibition of HMG-CoA reductase by compounds of the invention may be determined using known methods, such as that taught in U.S. Pat. No. 5,877,208, incorporated herein by reference and summarized below.

Rats are sacrificed by decapitation and the livers are excised and immediately placed in an ice-cold homogenization medium (50 mM KH$_2$PO$_4$ (pH 7.0), 0.2M sucrose, 2 mM dithiothreitol (DTT). The livers are homogenized in the homogenization medium (2 ml medium/g of the liver) with a Waring blender for 15 sec. (three strokes with a motor-driven Teflon pestle in a Potter-Elvehjem type glass homogenizer). The homogenate is centrifuged at 15,000×g for 10 min. and the supernatant thus obtained is centrifuged at 100,000×g for 75 min. to obtain microsomal pellets, which are then resuspended in the homogenization medium containing 50 mM EDTA and centrifuged at 100,000×g for 60 min. The supernatant containing the microsome is used as an enzyme source.

The activity of HMG-CoA reductase is determined by employing radiolabeled $^{14}$C HMG-CoA, in accordance with the method of Shapiro et al. (Shapiro et al *Biochemica et Biophysica Acta* 370:369 (1974)) as follows. The enzyme in the supernatant containing the microsome obtained in (Step 1) is activated at 37° C. for 30 min. Added to a reaction tube is 20 µl of HMG-CoA reductase assay buffer (0.25M KH$_2$PO$_4$ (pH 7.0), 8.75 mM EDTA, 25 mM DTT, 0.45M KCl and 0.25 mg/ml BSA), 5 µl of 50 mM NADPH, 5 µl of radiolabeled $^{14}$C HMG-CoA (0.05 µCi/tube, final conc. 120 µM), and 10 µl of activated microsomal enzyme (0.03-0.04 mg), and the mixture is incubated at 37° C. for 30 min. The reaction is terminated by adding 10 µl of 6M HCl to the mixture, and the mixture is incubated at 37° C. for 15 min. to allow complete lactonization of the product. The precipitate is removed by centrifugation at 10,000×g for 1 min. and the supernatant is applied to a Silica gel 60G TLC plate (Altech, Inc., Newark, U.S.A.) and then developed with benzene:acetone (1:1, v/v). The appropriate region is removed by scraping with a disposable cover slips and assayed for radioactivity with 1450 Microbeta liquid scintillation counter (Wallacoy, Finland). Enzyme activities are calculated as picomoles mevalonic acid synthesized per min. per mg protein (pmoles/min/mg protein). Control rats show a relatively high HMG-CoA reductase activity, while the HMG-CoA activities observed with rats fed compounds of the invention are lower than that of the control group.

Example 43

Method of Determining the ABCA-1 Activating Ability

This test will demonstrate the effectiveness of compounds of the invention on ABCA-1 gene expression, using a known method, as taught in U.S. Pat. No. 6,548,548, incorporated herein by reference. Briefly, the pGL3 luciferase reporter vector system (Promega, Madison, Wis.) is used to create a recombinant plasmid to measure reporter gene expression under control of the ABCA-1 promoter.

Plasmid pGL3-Basic (Promega, Madison, Wis.; Cat. #E1751) is used as a control plasmid containing the promoterless luciferase gene. The reporter construct containing the ABCA-1 promoter and luciferase gene is made by cloning a genomic fragment from the 5' flanking region of the ABCA-1 gene (hAPR1 5' promoter, corresponding to nucleotides 1080-1643 of SEQ ID NO: 3 as disclosed in U.S. Pat. No. 6,548,548) into the SacI site of the GL3-Basic plasmid to generate plasmid GL-6a. Next, plasmid GL-6a is digested with SpeI and Acc651. A BsiWI-SpeI fragment excised from a lambda subclone, representing the ABCA-1 genomic sequence corresponding to nucleotides 1-1534 of SEQ ID NO: 3 is ligated into the remaining vector/ABCA-I promoter fragment produced by this digestion. The resultant plasmid, pAPR1, encodes the luciferase reporter gene under transcriptional control of 1.75 kb of the human ABCA-1 promoter sequence.

The control or pAPR1 plasmid wisas transfected into confluent cultures of RAW 264.7 cells maintained in DMEM containing 10% fetal bovine serum. Each well of a 12 well dish is transfected for 5 hours with either pGL3-Basic, pGL3-Promoter or pAPR1 DNA (1 µg), luciferase plasmid DNA (1 µg), and 12 µl of Geneporter reagent (Gene Therapy Systems, San Diego, Calif.; Cat. #T201007). In addition, 0.1 µg of pCMVβ plasmid DNA (Clontech, Palo Alto, Calif., Cat. #6177-1) is added as a control for transfection efficiency. After 5 hours, the culture medium is replaced with serum-free DMEM/BSA in the presence or absence of acetylated LDL (100 µg/ml) and incubated for 24 hours.

Following transfection, the cells in each well are lysed in 70 µl of 1×cell lysis reagent (Promega, Madison, Wis., Cat. #E3971), subjected to one freeze-thaw cycle, and the lysate cleared by centrifugation for 5 minutes at 12,000×g. After centrifugation, 100 µl of luciferase assay reagent (Promega, Madison, Wis.; Cat. #E1501) is added to 10 µl of lysate. The luciferase activity of each lysate is measured as light units using a luminometer. Additionally, the β-galactosidase activity of each lysate is measured using the chemiluminescent assay reagents supplied in the Galacto-light kit according to the manufacturer's instructions (Tropix Inc., Bedford, Mass.: Cat. #BL100G). The normalized luciferase activity for each lysate is determined by dividing the luciferase activity value by the determined β-galactosidase value and reported as relative light units.

Example 44

Measurement of Reduced Hypertension In Vivo

A pressure transducer is connected to the right carotid artery via a catheter containing heparinized saline. The mean arterial pressure and heart rate are recorded. The rats are anesthetized with nembutal at an initial dose of 35 mg/kg body weight with additional smaller injections as necessary. The compounds are dissolved in a pharmaceutical carrier (such as Abbott's 5% dextrose USP) and injected into the rats via a catheter in the right femoral vein. Positive controls that may be employed include sodium nitroprusside and $NaNO_2$, while $NaNO_3$ may be employed as a negative control. The results will show that the compounds provided for in the invention are potent anti-hypertensives, that decreases blood pressure significantly. The peak value of the blood pressure decrease should take a short time to reach, for example approximately one minute, after injection and the blood pressure should start to rise again soon thereafter and should have totally recovered within about approximately 10 to 15 minutes.

Example 45

Measurement of the Reduction of Degree of Restenosis After Arterial Injury in High Cholesteric Rabbits The procedure of Tomaru, as described in U.S. Pat. No. 5,595,974 and further described by Goodman in U.S. Pat. No. 6,022,901, both herein incorporated by reference, may be used to evaluate the utility of the compounds of the invention to preventing restenosis in high cholesteric rabbits.

Example 46

Use in Preventing Restenosis in Humans

The procedure of Tardif et al., *New England J. Med.* 337: 365 (1997))may be carried out as described by Goodman in U.S. Pat. No. 6,022,901, incorporated herein by reference, to examine the ability of compounds of the invention to prevent restenosis in humans.

Example 47

Measurement of Platelet Anti-Aggregating Activity

Platelet anti-aggregating activity may be evaluated in vitro on human platelets stimulated by thrombin in accordance with the method described by Bertele et al., *Science* 220:517 (1983).

Example 48

Measurement of the Influence on ADP-Induced Aggregation of Platelets in Rabbits

Aggregation of platelet testing: Rabbit blood is sampled by cardiac puncture from rabbit with silicon-coated syringe. The blood is mixed with 3.8% sodium citrate at 9:1 and spun at 1,000 rpm for 6 minutes. 1 ml of the platelet-rich plasma is transferred to a silicon-coated 2 ml cell, mixed and read for transmittance (Ti), with a spectrophotometer. 0.02 ml of ADP (10 mu.M) is added, stirred, and read for transmittance of the platelet-containing-plasma once per minute and the maximal transmittance (Tm) is obtained within 10 minutes. Spin the blood sample at 3000 rpm for 45 minutes and read for transmittance.

Example 49

Measurement of the Effect on Collagen Induced Thrombo-cytopenia In Vivo

Male rats (Charles River, CRL:CD(SD), 400-450×g) are anesthetized with Sodium pentabarbital (65 mg/kg, Vet Labs, Limited, Inc., Lenexa, Kans.). Two incisions are made to expose both jugular veins. Using an infusion pump (Harvard Apparatus, South Natick, Mass.) and a 5 cc syringe with a 19 gauge butterfly, the test compound or vehicle is infused into the left jugular vein at a rate of 0.39 ml/min for 3 minutes. After 2 minutes of compound/vehicle infusion, collagen (60 µg/kg) (Helena Laboratories, Beaumont, Tex.) is injected with a 1 ml syringe into the right jugular vein. The body cavity is opened and the vena cava is exposed for blood sampling. One minute after the collagen injection, compound infusion is stopped and blood is sampled from the vena cava (within 30 sec) with a 3 cc syringe containing 0.3 mg of 4.5% EDTA/Tris (0.1 M) (pH 7.35) plus 150 µM indomethacin. Platelet rich plasma (PRP) is prepared by centrifuging the blood at 126×g for 10 min. 5 µl of PRP is counted in 20 ml of Isoton.® III in a Coulter Counter. Percent inhibition of collagen induced aggregation is calculated by comparison of the number of platelets counted in treated animals with numbers for animals receiving no collagen and with counts from animals receiving vehicle and collagen. Estimation of potency is based on inhibition of collagen-induced thrombocytopenia.

Example 50

Measurement of In Vivo Anti-Psoriatic Effectiveness

A topical formulation comprising a compound of the invention is administered to the affected area of human patients suffering from psoriasis. A control formulation, containing none of the compound of the invention, is applied to a comparable area of the patient. The effectiveness of the compound is determined by analyzing the improvement in inflammation and decrease in proliferative cells at the site at which the compound is applied compared to the site at which control formulation is applied at 3 and 7 days following administration.

Example 51

Measurement of Protein Kinase Inhibition

A compound of the invention is mixed with radio-labeled ATP, an appropriate protein kinase and an appropriate substrate in an appropriate buffer. Following incubation the reaction is stopped by spotting onto filter paper and a scintillation counter employed to quantify the difference in ATP addition to the substrate, which measures the amount of protein kinase inhibition, when compared to control.

Example 52

Measurement of Inhibition of Neutrophil Activation

A compound of the invention is tested using the protocol of Tudan, *Biochem. Pharmacol.* 58:1869 (1999). This test demonstrates the ability of the test compound to inhibit the activation of neutrophils caused by crystals and by chemoattractants such as fMLP.

Example 53

Measurement of Inhibition of TPA-Induced Inflammation

A compound of the invention is tested by a modified method of Marks et al., *Cancer Res.* 36:2636 (1976) to demonstrate the compound's effectiveness against inflammation induced by application of 12-O-tetradecanoylphorbol-13-acetate (TPA). The compound is applied to an ear of a mouse, followed by application of TPA. Four hours later a biopsy punch of the mouse ear is weighed to measure edema, compared to a biopsy punch of the other ear which received no compound.

Example 54

Measurement of the Inhibition of Carrageenan-Induced Inflammation

A compound of the invention is tested by the method of Slowing et al., *J Wrhnoph Exol.* 43:9 (1994) in Wistar rats. Animals receive intradermal injections of Freund's adjuvant into the tail. Seven days later, the test compound is administered, followed one hour later by a suspension of carrageenan in saline solution into the left hind paw. Paw volume is measured by water plethysmography and compared to control.

Example 55

Measurement of Cancer Chemopreventative Activity

C3H/10T1/2 clone 8 cells (ATCC) are treated with a compound of the invention by the method of Mondal et al., *Cancer Res.* 36:2254 (1976). The cells in culture are treated with 3-methylcholanthrene for 24 hours, followed by washing a five days of incubation in fresh medium. TPA is subsequently added to the medium, with or without the test compound. Seven weeks after confluency is reached, fixation with methanol and staining with Giemsa reveals Type II and III transformed foci, which are scored to demonstrate effectiveness of inhibition of two-stage transformation by the test compound.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for increasing expression of ApoA-I in a mammal comprising administering a therapeutically effective amount of a compound of Formula I:

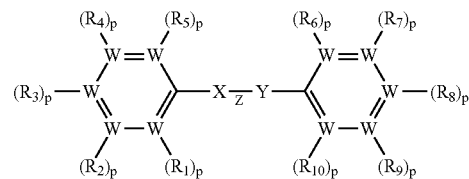

Formula I or a pharmaceutically acceptable salt thereof wherein:
X is selected from $CR_{11}$, and N;
Y is selected from $CR_{12}$, and N;
$R_3$ and $R_8$ are each hydroxyl;
$R_{11}$ and $R_{12}$ are each independently selected from alkoxy, aryloxy, alkenyl, amino, aryl, arylalkyl, carbamate, carboxy, cyano, cycloalkyl, ester, ether, formyl, haloalkyl, heteroaryl, heterocyclyl, hydroxyl, ketone, phosphate, sulfide, sulfinyl, sulfonyl, sulfonic acid, sulfonamide and thioketone;
$R_1$, $R_5$, $R_6$, and $R_{10}$ are each independently selected from alkoxy, aryloxy, alkyl, alkenyl, alkynyl, amide, amino, aryl, arylalkyl, carbamate, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone;
$R_2$, $R_4$, $R_7$, and $R_9$, are each independently selected from aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone, or
two adjacent substituents selected from $R_1$, $R_2$, $R_4$, $R_5$, $R_6$, $R_7$, $R_9$, $R_{10}$, $R_{11}$, and $R_{12}$ are connected in a 5 or 6-membered ring to form a bicyclic aryl or bicyclic heteroaryl;
each W is independently selected from C and N; and
Z is a double bond;
provided that:
$R_2$ and $R_4$ are not each hydroxyl;
at least one W is N;
when W is N, then p is 0; and
when W is C, then p is 1

2. The method of claim 1, wherein the therapeutically effective amount of the compound of Formula I is sufficient to establish a concentration ranging from about 0.001 μM to about 100 μM in the mammal.

3. The method of claim 2, wherein the concentration ranges from about 1 μM to about 20 μM.

4. The method of claim 1, wherein the therapeutically effective amount of the compound of Formula I is administered with a pharmaceutically acceptable carrier in a pharmaceutically acceptable composition.

5. The method of claim 1, further comprising treating or reducing the risk of developing a cardiovascular, cholesterol or lipid related disorder.

6. The method of claim 1, wherein the double bond is an E-double bond.

7. A method for increasing expression of ApoA-I in a mammal comprising administering a therapeutically effective amount of a compound selected from:
4,4'-dihydroxy-stilbene;
6-[(E)-2-(4-Hydroxy-phenyl)-vinyl]-pyridin-3-ol;
5-[(E)-2-(4-Hydroxy-phenyl)-vinyl]-pyrazin-2-ol;

5-{[1-(4-Hydroxy-phenyl)-meth-(E)-ylidene]-amino}-pyridin-2-ol;
5-(4-Hydroxy-phenylazo)-pyridin-2-ol;
3-Hydroxymethyl-4-[(E)-2-(4-hydroxy-phenyl)-vinyl]-phenol;
2-Hydroxy-5-[(E)-2-(4-hydroxyphenyl)vinyl]benzoic acid;
3-Nitro-4-[(E)-2-(4-hydroxyphenyl)-vinyl]phenol;
(E)-Ethyl 2-hydroxy-5-(4-hydroxystyryl) benzoate;
4-[(E)-2-(4-Hydroxyphenyl)vinyl]-3-methanesulfonylphenol;
3-Amino-4-[(E)-2-(4-hydroxy-phenyl)vinyl]phenol;
N-{5-Hydroxy-2-[(E)-2-(4-hydroxyphenyl)vinyl]phenyl}-acetamide;
5-Hydroxy-2-[2-(4-hydroxyphenyl)vinyl]-N,N-dimethylbenzamide;
4-[4-Hydroxy-phenethyl]-phenol;
4-Hydroxy-thiobenzoic acid S-(4-hydroxy-phenyl) ester;
4-Hydroxy-benzoic acid pyridin-2-yl ester;
4-(4-Hydroxy-phenyl)-azophenol,
and pharmaceutically acceptable salts thereof.

8. A method for increasing expression of ApoA-I in a mammal comprising administering a therapeutically effective amount of 5-[(E)-2-(4-Hydroxyphenyl)-vinyl]-pyridin-2-ol, or a pharmaceutically acceptable salt thereof.

9. The method according to claim 5, wherein the cardiovascular, cholesterol or lipid related disorder is selected from acute coronary syndrome, angina pectoris, arteriosclerosis, atherosclerosis, carotid atherosclerosis, cerebrovascular disease, cerebral infarction, congestive heart failure, congenital heart disease, coronary heart disease, coronary artery disease, coronary plaque stabilization, dyslipidemias, dyslipoproteinemias, endothelium dysfunctions, familial hypercholeasterolemia, familial combined hyperlipidemia, hypertension, hyperlipidemia, intermittent claudication, ischemia, ischemia reperfusion injury, ischemic heart diseases, multi-infarct dementia, myocardial infarction, peripheral vascular disease, restenosis, renal artery atherosclerosis, rheumatic heart disease, stroke, thrombotic disorder, transitory ischemic attacks, and lipoprotein abnormalities associated with Alzheimer's disease, obesity, diabetes mellitus, syndrome X and impotence.

10. The method according to claim 9, wherein the cardiovascular, cholesterol or lipid related disorder is selected from dyslipidemias, dyslipoproteinemias, hypertension, coronary artery disease, and atherosclerosis.

11. The method of claim 1, wherein $R_1$, $R_5$, $R_6$, and $R_{10}$ are each independently selected from alkoxy, aryloxy, alkyl, amide, amino, cyano, cycloalkyl, ester, ether, formyl, halogen, haloalkyl, hydrogen, hydroxyl, nitro, phosphate, sulfonyl, sulfonic acid, and sulfonamide.

12. The method of claim 1, wherein $R_2$, $R_4$, $R_7$, and $R_9$, are each independently selected from amide, amino, carboxy, cyano, ester, ether, formyl, halogen, hydrogen, hydroxyl, phosphate, sulfide, sulfonic acid, and sulfonamide.

13. The method of claim 1, wherein only one W is N.

* * * * *

UNITED STATES PATENT AND TRADEMARK OFFICE
CERTIFICATE OF CORRECTION

| | |
|---|---|
| PATENT NO. | : 7,846,915 B2 |
| APPLICATION NO. | : 11/254420 |
| DATED | : December 7, 2010 |
| INVENTOR(S) | : Norman C. W. Wong et al. |

It is certified that error appears in the above-identified patent and that said Letters Patent is hereby corrected as shown below:

Claim 1, col. 138, line 45, insert a -- . -- after "1".

Signed and Sealed this
Fourteenth Day of February, 2012

David J. Kappos
*Director of the United States Patent and Trademark Office*